(12) United States Patent
Jansen et al.

(10) Patent No.: US 8,394,293 B2
(45) Date of Patent: *Mar. 12, 2013

(54) THIOPHENE DERIVATIVES, AND LC MEDIA CONTAINING SAME

(75) Inventors: Axel Jansen, Darmstadt (DE); Detlef Pauluth, Ober-Ramstadt (DE); Harald Hirschmann, Darmstadt (DE); Markus Czanta, Darmstadt (DE)

(73) Assignee: Merck Patent Gesellschaft mit beschrankter Haftung, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/989,220

(22) PCT Filed: Mar. 30, 2009

(86) PCT No.: PCT/EP2009/002298
§ 371 (c)(1),
(2), (4) Date: Oct. 22, 2010

(87) PCT Pub. No.: WO2009/129915
PCT Pub. Date: Oct. 29, 2009

(65) Prior Publication Data
US 2011/0049427 A1    Mar. 3, 2011

(30) Foreign Application Priority Data
Apr. 24, 2008 (DE) .................. 10 2008 020 530

(51) Int. Cl.
C09K 19/34 (2006.01)
C09K 19/06 (2006.01)
C09K 19/52 (2006.01)
C09K 19/00 (2006.01)
C07D 333/02 (2006.01)

(52) U.S. Cl. ........... 252/299.61; 252/299.01; 252/299.6; 252/299.63; 252/299.64; 252/299.65; 428/1.1; 428/1.3; 548/136; 548/143; 548/146; 549/29; 549/429; 349/1; 349/56

(58) Field of Classification Search ............. 252/299.01, 252/299.6–299.67; 428/1.1, 1.3; 430/20; 349/1, 56; 548/136, 143, 146; 549/29, 429
See application file for complete search history.

(56) References Cited

U.S. PATENT DOCUMENTS

| 5,244,595 A | 9/1993 | Yamada et al. |
| 5,733,476 A * | 3/1998 | Takiguchi et al. ....... 252/299.62 |
| 6,696,110 B1 | 2/2004 | Tuffin et al. |
| 2010/0252777 A1 * | 10/2010 | Klasen-Memmer et al. ................ 252/299.61 |

FOREIGN PATENT DOCUMENTS

| DE | 19907063 A1 | 8/2000 |
| EP | 0467260 A2 | 1/1992 |
| EP | 0499252 A1 | 8/1992 |
| JP | 200784487 A | 4/2007 |

OTHER PUBLICATIONS

World Intellectual Property Organization. "International Search Report." PCT/EP2009/002298, Applicant: MERCK GMBH, Mailed Jun. 24, 2009.
Espacenet Database. "English Abstract—Thiophene Compound, Liquid Crystal Composition Comprising the Same Compound and Liquid Crystal Element." JP200784487A, Applicant: Adeka Corp, Apr. 5, 2007.
Espacenet Database. "English Abstract—New fluorinated thiophene derivatives useful as components of liquid crystal mixtures for use in switching and display devices." DE19907063A1, Applicant: Clariant GMBH, Aug. 24, 2000.

* cited by examiner

*Primary Examiner* — Geraldina Visconti
(74) *Attorney, Agent, or Firm* — Millen, White, Zelano & Branigan, P.C.

(57) ABSTRACT

The present invention relates to thiophene derivatives, to processes and intermediates for the preparation thereof, to the use thereof for optical, electro-optical and electronic purposes, in particular in liquid-crystal (LC) media and LC displays, and to LC media and LC displays comprising same.

20 Claims, No Drawings

THIOPHENE DERIVATIVES, AND LC MEDIA CONTAINING SAME

The present invention relates to thiophene derivatives, to processes and intermediates for the preparation thereof, to the use thereof for optical, electro-optical and electronic purposes, in particular in liquid-crystal (LC) media and LC displays, and to LC media and LC displays comprising same.

Liquid crystals are used principally as dielectrics in display devices, since the optical properties of such substances can be modified by an applied voltage. Electro-optical devices based on liquid crystals are extremely well known to the person skilled in the art and can be based on various effects. Examples of such devices are cells having dynamic scattering, DAP (deformation of aligned phases) cells, guest/host cells, TN cells having a twisted nematic structure, STN (supertwisted nematic) cells, SBE (super-birefringence effect) cells and OMI (optical mode interference) cells. The commonest display devices are based on the Schadt-Helfrich effect and have a twisted nematic structure. In addition, there are also cells which work with an electric field parallel to the substrate and liquid-crystal plane, such as, for example, IPS (in-plane switching) cells. In particular, TN, STN and IPS cells, especially TN, STN and IPS cells, are currently commercially interesting areas of application for the media according to the invention.

The liquid-crystal materials must have good chemical and thermal stability and good stability to electric fields and electromagnetic radiation. Furthermore, the liquid-crystal materials should have low viscosity and produce short addressing times, low threshold voltages and high contrast in the cells.

They should furthermore have a suitable mesophase, for example a nematic mesophase for the above-mentioned cells, at the usual operating temperatures, i.e. in the broadest possible range above and below room temperature. Since liquid crystals are generally used as mixtures of a plurality of components, it is important that the components are readily miscible with one another. Further properties, such as the electrical conductivity, the dielectric anisotropy and the optical anisotropy, have to satisfy various requirements depending on the cell type and area of application. For example, materials for cells having a twisted nematic structure should have positive dielectric anisotropy and low electrical conductivity.

For example, for matrix liquid-crystal displays with integrated non-linear elements for switching individual pixels (MLC displays), media having large positive dielectric anisotropy, broad nematic phases, relatively low birefringence, very high specific resistance, good UV and temperature stability and low vapour pressure are desired.

Matrix liquid-crystal displays of this type are known. Examples of nonlinear elements which can be used to individually switch the individual pixels are active elements (i.e. transistors). The term "active matrix" is then used, where a distinction can be made between two types:

1. MOS (metal oxide semiconductor) or other diodes on silicon wafers as substrate.
2. Thin-film transistors (TFTs) on a glass plate as substrate.

The use of single-crystal silicon as substrate material restricts the display size, since even modular assembly of various part-displays results in problems at the joints.

In the case of the more promising type 2, which is preferred, the electro-optical effect used is usually the TN effect. A distinction is made between two technologies: TFTs comprising compound semiconductors, such as, for example, CdSe, or TFTs based on polycrystalline or amorphous silicon. Intensive work is being carried out worldwide on the latter technology.

The TFT matrix is applied to the inside of one glass plate of the display, while the other glass plate carries the transparent counterelectrode on its inside. Compared with the size of the pixel electrode, the TFT is very small and has virtually no adverse effect on the image. This technology can also be extended to fully colour-capable displays, in which a mosaic of red, green and blue filters is arranged in such a way that a filter element is opposite each switchable pixel.

The TFT displays usually operate as TN cells with crossed polarisers in transmission and are backlit.

The term MLC displays here encompasses any matrix display with integrated non-linear elements, i.e., besides the active matrix, also displays with passive elements, such as varistors or diodes (MIM=metal-insulator-metal).

MLC displays of this type are particularly suitable for TV applications (for example pocket televisions) or for high-information displays for computer applications (laptops) and in automobile or aircraft construction. Besides problems regarding the angle dependence of the contrast and the response times, difficulties also arise in MLC displays due to insufficiently high specific resistance of the liquid-crystal mixtures [TOGASHI, S., SEKIGUCHI, K., TANABE, H., YAMAMOTO, E., SORIMACHI, K., TAJIMA, E., WATANABE, H., SHIMIZU, H., Proc. Eurodisplay 84, September 1984: A 210-288 Matrix LCD Controlled by Double Stage Diode Rings, pp. 141 ff, Paris; STROMER, M., Proc. Eurodisplay 84, September 1984: Design of Thin Film Transistors for Matrix Addressing of Television Liquid Crystal Displays, pp. 145 ff, Paris]. With decreasing resistance, the contrast of an MLC display deteriorates, and the problem of after-image elimination may occur. Since the specific resistance of the liquid-crystal mixture generally drops over the life of an MLC display owing to interaction with the interior surfaces of the display, a high (initial) resistance is very important in order to obtain acceptable lifetimes. In particular in the case of low-volt mixtures, it was hitherto impossible to achieve very high specific resistance values. It is furthermore important that the specific resistance exhibits the smallest possible increase with increasing temperature and after heating and/or UV exposure. The low-temperature properties of the mixtures from the prior art are also particularly disadvantageous. It is demanded that no crystallisation and/or smectic phases occur, even at low temperatures, and the temperature dependence of the viscosity is as low as possible. The MLC displays from the prior art thus do not satisfy today's requirements.

Besides liquid-crystal displays which use backlighting, i.e. are operated transmissively and if desired transflectively, reflective liquid-crystal displays are also particularly interesting. These reflective liquid-crystal displays use the ambient light for information display. They thus consume significantly less energy than backlit liquid-crystal displays having a corresponding size and resolution. Since the TN effect is characterised by very good contrast, reflective displays of this type can even be read well in bright ambient conditions. This is already known of simple reflective TN displays, as used, for example, in watches and pocket calculators. However, the principle can also be applied to high-quality, higher-resolution active matrix-addressed displays, such as, for example, TFT displays. Here, as already in the transmissive TFT-TN displays which are generally conventional, the use of liquid crystals of low birefringence ($\Delta n$) is necessary in order to achieve low optical retardation ($d \cdot \Delta n$). This low optical retardation results in usually acceptably low viewing-angle dependence of the contrast (cf. DE 30 22 818). In reflective displays, the use of liquid crystals of low birefringence is even more important than in transmissive displays since the effective layer thickness through which the light passes is approximately twice as large in reflective displays as in transmissive displays having the same layer thickness.

For TV and video applications, MLC displays having short response times are required. Such short response times can be achieved, in particular, if liquid-crystal media having low values for the viscosity, in particular the rotational viscosity $\gamma_1$, are used. However, diluting additives generally lower the clearing point and thus reduce the working-temperature range of the medium.

Thus, there continues to be a great demand for MLC displays having very high specific resistance at the same time as a large working-temperature range, short response times, even at low temperatures, and a low threshold voltage which do not exhibit these disadvantages or only do so to a lesser extent.

In the case of TN (Schadt-Helfrich) cells, media are desired which facilitate the following advantages in the cells:
    extended nematic phase range (in particular down to low temperatures)
    ability to switch at extremely low temperatures (outdoor use, automobiles, avionics)
    increased resistance to UV radiation (longer life)
    low threshold voltage.

The media available from the prior art do not enable these advantages to be achieved while simultaneously retaining the other parameters.

In the case of supertwisted (STN) cells, media are desired which facilitate greater multiplexability and/or lower threshold voltages and/or broader nematic phase ranges (in particular at low temperatures). To this end, a further widening of the available parameter latitude (clearing point, smectic-nematic transition or melting point, viscosity, dielectric parameters, elastic parameters) is urgently desired.

In the case of LC displays for TV and video applications (for example LCD TVs, monitors, PDAs, notebooks, games consoles), a significant reduction in the response times is desired. There is therefore a demand for compounds for LC media which facilitate a reduction in the response times without simultaneously impairing the other properties of the LC medium, such as, for example, the clearing point, the dielectric anisotropy $\Delta\epsilon$ or the birefringence $\Delta n$. Low rotational viscosities, in particular, are desirable for this purpose.

In the case of applications of LC media having positive dielectric anisotropy, fast response times are generally demanded. It is known that a reduction in the layer thickness d of the LC medium in the LC cell theoretically results in a reduction in the response times. LC media having relatively high birefringence values $\Delta n$ are therefore required for this purpose in order to ensure an adequate optical retardation $d \cdot \Delta n$. On the other hand, however, LC media having relatively high birefringence values typically also have relatively high values of the rotational viscosity, which in turn results in longer response times. The shortening of the response time achieved by reducing the layer thickness is thus at least partly compensated again by the relatively high rotational viscosity of the LC medium used. There is therefore an urgent demand for LC media which simultaneously have high birefringence values and low rotational viscosities.

The invention is based on the object of providing media, in particular for MLC, TN, STN or IPS displays of this type, which have the desired properties indicated above and do not exhibit the disadvantages indicated above or only do so to a lesser extent. In particular, the LC media should have fast response times and low rotational viscosities at the same time as high dielectric anisotropy and high birefringence. In addition, the LC media should have a high clearing point, a broad nematic phase range and a low threshold voltage.

It has now been found that this object can be achieved if thiophene derivatives according to the invention are used in LC media, in particular in LC media having positive dielectric anisotropy, and in MLC, TN, STN and IPS displays. These thiophene derivatives result in LC media having the desired properties indicated above.

JP 2007-084487 discloses thiophene derivatives in which a thiophene-2,5-diyl unit is linked directly or via bridges to a 2,3-difluorophenylene-1,4-diyl unit. However, these compounds have negative dielectric anisotropy and are thus unsuitable for applications in dielectrically positive LC media. Furthermore, a 2,3-difluorophenylene-1,4-diyl unit generally results in comparatively high rotational viscosities than less-fluorinated phenylene units.

EP 0 467 260 B1 discloses compounds containing a thiophene-2,5-diyl unit which is linked directly to a 2- and/or 3-substituted phenylene-1,4-diyl unit. However, the object on which EP 0 467 260 B1 was based was the development of novel materials for use in ferroelectric LC displays. EP 0 467 260 B1 therefore also relates, in particular, to ferroelectric LC media and ferroelectric LC substances and to compounds in general which have properties which are particularly suitable for use in ferroelectric LC displays.

In particular, LC media having a chiral smectic C phase (SmC*) are suitable for use in ferroelectric LC displays. In general, mesogenic compounds having smectic phases are required for the preparation of such LC media. Smectic phases are preferably formed if the skeleton of the liquid-crystal structure is provided with particularly long alkyl or alkoxy side chains, as disclosed in the particularly preferred embodiments in EP 0 467 260 B1. Smectic phases are also stabilised if polar carbonyl functions, such as —C(O)—, are present in the side chain, as disclosed in some preferred embodiments in EP 0 467 260 B1. Chiral mesogenic compounds are required for the induction of an SmC* phase. The compounds in EP 0 467 260 B1 therefore preferably have branched alkyl chains having a centre of chirality, which can also be combined with an ester function, as, for example, in example compound I-40 on page [lacuna] of EP 0 467 260 B1:

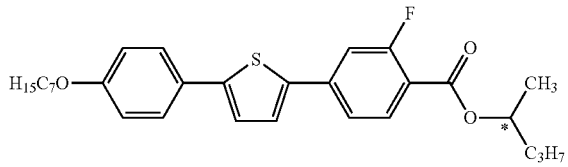

However, ferroelectric LC displays are of only minor importance today. Virtually exclusively nematic liquid-crystal media are used for modern display applications. However, the compounds described in EP 0 467 260 B1 are unsuitable for modern display applications of this type since virtually exclusively smectic liquid crystals are described.

As shown in the comparative examples below, the other compounds from EP 0 467 260 B1, which have no centres of chirality, carbonyl or carboxyl functions in the side chains, and have directly linked rings, likewise do not have the favourable properties which are necessary for use in LC displays according to the invention.

Thus, example compound I-1 on page 12 of EP 0 467 260 B1 is only nematic in a very limited temperature range (C 115 N 119 I):

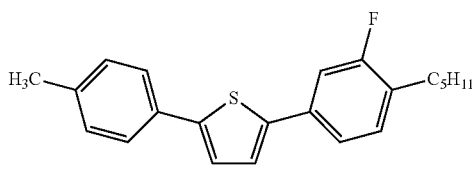

In addition, this compound exhibits poor values for the clearing point (145° C.) and the rotational viscosity (196 mPa·s), which can be explained by the molecular structure, which is angled overall owing to the central thiophene unit.

The subsequent example compound "(I-4)" on page 38 of EP 0 467 260 B1

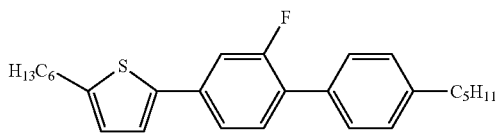

has a broad range of smectic phases (C 44 Sm (6) SmB (38) SmC 68 SmA 75 N 93.5 I).

The subsequent example compound "(I-5)" on page 39 of EP 0 467 260 B1

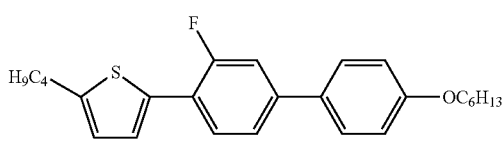

likewise has a broad range of smectic phases (C 66 SmE 89 SmC 131 SmA 144 N 146.4 I) and an unfavourable rotational viscosity to clearing point ratio (cl.p.: 179° C., $\gamma_1$: 262 mPa·s).

Further example compounds in EP 0 467 260 B1 are unsuitable for use in modern MLC displays, for example owing to the presence of keto and/or ester functions, since these functional groups result in poor reliability, in particular a poor voltage holding ratio (VHR). In addition, branches, for example within an alkyl side chain, as are necessary for chiral smectic liquid crystals, are generally undesired for nematic liquid crystals since this results in higher rotational viscosity and thus poor response times.

It was therefore unexpected to the person skilled in the art on the basis of the prior art that the use of thiophene derivatives according to the invention in achiral nematic LC media having an inherently untwisted phase, in particular in LC media having positive dielectric anisotropy, and in MLC, TN, STN and IPS displays can result in an improvement in the properties, in particular in fast response times and low rotational viscosities at the same time as high dielectric anisotropy, high birefringence and high specific resistance.

The present invention thus relates to an LC medium, preferably an LC medium which has a preferably achiral, nematic phase at room temperature, comprising one or more compounds of the formula I

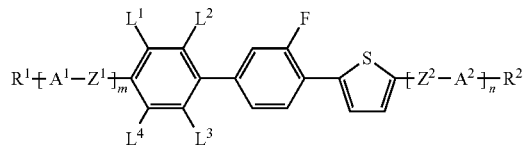

in which the individual radicals have the following meaning:
$R^1$ and $R^2$ denote H, F, Cl, Br, —CN, —SCN, $SF_5$ or straight-chain or branched alkyl having 1 to 12 C atoms, in which, in addition, one or more non-adjacent $CH_2$ groups may each be replaced, independently of one another, by —CH=CH—, —C≡C—, —CO—, —CO—O—, —O—CO—, —O—CO—O— in such a way that O atoms are not linked directly to one another, and in which, in addition, one or more H atoms may be replaced by F, Cl or Br, or P-Sp-,
P denotes a polymerisable group,
Sp denotes a spacer group or a single bond,
$A^1$ and $A^2$ each, independently of one another, denote phenylene-1,4-diyl, in which, in addition, one or two CH groups may be replaced by N and one or more H atoms may be replaced by halogen, CN, $CH_3$, $CHF_2$, $CH_2F$, $OCH_3$, $OCHF_2$ or $OCF_3$, cyclohexane-1,4-diyl, in which, in addition, one or two non-adjacent $CH_2$ groups may be replaced, independently of one another, by O and/or S and one or more H atoms may be replaced by F, or denote cyclohexene-1,4-diyl, bicyclo[1.1.1]-pentane-1,3-diyl, bicyclo[2.2.2]octane-1,4-diyl, spiro[3.3]-heptane-2,6-diyl, tetrahydropyran-2,5-diyl or 1,3-dioxane-2,5-diyl,
$Z^1$ and $Z^2$ each, independently of one another, denote —$CF_2O$—, —$OCF_2$—, —$CH_2O$—, —$OCH_2$—, —CO—O—, —O—CO—, —$C_2H_4$—, —$C_2F_4$—, —$CF_2CH_2$—, —$CH_2CF_2$—, —CFHCFH—, —CFHCH_2$—, —$CH_2CFH$—, —$CF_2CFH$—, —$CFHCF_2$—, —CH=CH—, —CF=CH—, —CH=CF—, —CF=CF—, —C≡C— or a single bond,
$L^{1-4}$ each, independently of one another, denote H, halogen, $CF_3$ or CN,
m and n each, independently of one another, denote 0, 1 or 2.

The invention furthermore relates to novel compounds of the formula I, in particular those in which n denotes 0 and m denotes 0 or 1, and those in which $R^1$ and $R^2$ each, independently of one another, denote H, F, Cl, Br, —CN, —SCN, $SF_5$, P-Sp-, halogen, or alkyl, alkenyl or alkynyl having 1 to 8, preferably 1 to 5, C atoms, each of which is optionally substituted by halogen, in particular by F.

The invention furthermore relates to novel processes for the preparation of compounds of the formula I, and to intermediates obtained or used therein.

The invention furthermore relates to the use of compounds of the formula I and LC media according to the invention in electro-optical displays, in particular LC displays.

The invention furthermore relates to an LC display containing one or more compounds of the formula I or an LC medium according to the invention, in particular an MLC, TN, STN or IPS display.

In the compounds of the formula I, m and n preferably denote 0 or 1, particularly preferably n=0, particularly preferably m=0 or 1 if n simultaneously denotes 0, very particularly preferably m=n=0.

L$^1$-L$^4$ preferably each, independently of one another, denote H, halogen, CF$_3$ or CN, preferably H or halogen, particularly preferably H or F, very particularly preferably H.

A$^1$ and A$^2$ particularly preferably denote phenylene-1,4-diyl, which may also be mono- or polysubstituted by F. Z$^1$ and Z$^2$ particularly preferably denote a single bond.

In the compounds of the formula I, A$^1$ and A$^2$ and the ring

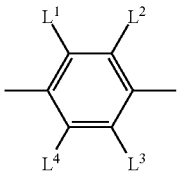

preferably denote

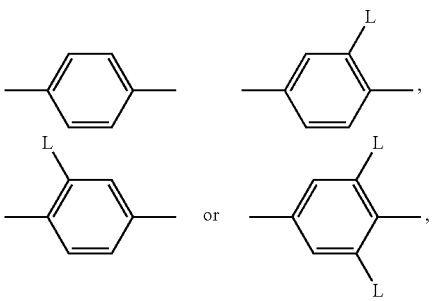

in which L has one of the meanings indicated for L$^1$ and preferably denotes F.

LC media which have an achiral LC phase without the presence of chiral dopants, and compounds of the formula I in which the radicals Z$^{1,2}$, A$^{1,2}$, R$^{1,2}$ do not have a centre of chirality, are generally preferred.

Preferred radicals R$^1$ and R$^2$ preferably denote H, halogen, or alkyl, alkenyl, alkynyl or alkoxy having 1 to 12, preferably 1 to 8, C atoms, each of which is optionally substituted by halogen, in particular by F, particularly preferably H, F, alkyl, alkenyl or alkynyl having 1 to 8 C atoms. R$^1$ is very particularly preferably equal to alkyl. R$^2$ is furthermore preferably H, alkyl or fluorine. Very particularly preferably, R$^1$ is alkyl and R$^2$ is H or alkyl. R$^1$, R$^2$ each, independently of one another, very particularly preferably denote H or unbranched alkyl having 1-5 C atoms. If R$^1$ and R$^2$ denote substituted alkyl, alkoxy, alkenyl or alkynyl, the total number of C atoms in the two groups R$^1$ and R$^2$ is preferably less than 10.

Preferred alkyl groups are, for example, methyl, ethyl, n-propyl, n-butyl, n-pentyl, n-hexyl, n-heptyl and n-octyl.

Preferred alkenyl groups are, for example, ethenyl, propenyl, butenyl and pentenyl.

Preferred alkynyl groups are, for example, ethynyl, propynyl, butynyl, pentynyl, hexynyl, heptynyl and octynyl.

Preferred alkoxy groups are, for example, methoxy, ethoxy, n-propoxy, n-butoxy, n-pentoxy, n-hexoxy, n-heptoxy, n-octoxy.

Halogen preferably denotes F or Cl.

The polymerisable group P is a group which is suitable for a polymerisation reaction, such as, for example, free-radical or ionic chain polymerisation, polyaddition or polycondensation, or for a polymer-analogous reaction, for example addition or condensation onto a main polymer chain. Particular preference is given to groups for chain polymerisation, in particular those containing a C=C double bond or C≡C triple bond, and groups which are suitable for polymerisation with ring opening, such as, for example, oxetane or epoxide groups.

Preferred groups P are selected from CH$_2$=CW$^1$—COO—, CH$_2$=CW$^1$—CO—,

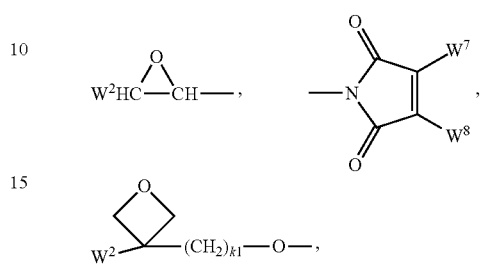

CH$_2$=CW$^2$—(O)$_{k3}$—, CH$_3$—CH=CH—O—, (CH$_2$=CH)$_2$CH—OCO—, (CH$_2$=CH—CH$_2$)$_2$CH—OCO—, (CH$_2$=CH)$_2$CH—O—, (CH$_2$=CH—CH$_2$)$_2$N—, (CH$_2$=CH—CH$_2$)$_2$N—CO—, HO—CW$^2$W$^3$—, HS—CW$^2$W$^3$—, HW$^2$N—, HO—CW$^2$W$^3$—NH—, CH$_2$=CW$^1$—CO—NH—, CH$_2$=CH—(COO)$_{k1}$-Phe-(O)$_{k2}$—, CH$_2$=CH—(CO)$_{k1}$-Phe-(O)$_{k2}$—, Phe-CH=CH—, HOOC—, OCN— and W$^4$W$^5$W$^6$Si—, in which W$^1$ denotes H, F, Cl, CN, CF$_3$, phenyl or alkyl having 1 to 5 C atoms, in particular H, F, Cl or CH$_3$, W$^2$ and W$^3$ each, independently of one another, denote H or alkyl having 1 to 5 C atoms, in particular H, methyl, ethyl or n-propyl, W$^4$, W$^5$ and W$^6$ each, independently of one another, denote Cl, oxaalkyl or oxacarbonylalkyl having 1 to 5 C atoms, W$^7$ and W$^8$ each, independently of one another, denote H, Cl or alkyl having 1 to 5 C atoms, Phe denotes 1,4-phenylene, which is optionally substituted by one or more radicals L as defined above, k$_1$, k$_2$ and k$_3$ each, independently of one another, denote 0 or 1, and k$_3$ preferably denotes 1.

Particularly preferred groups P are CH$_2$=CW$^1$—COO—, in particular CH$_2$=CH—COO—, CH$_2$=C(CH$_3$)—COO— and CH$_2$=CF—COO—, furthermore CH$_2$=CH—O—, (CH$_2$=CH)$_2$CH—OCO—, (CH$_2$=CH)$_2$CH—O—,

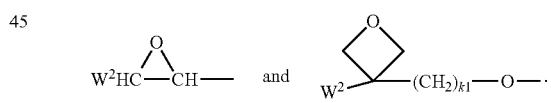

Very particularly preferred groups P are vinyloxy, acrylate, methacrylate, fluoroacrylate, chloroacrylate, oxetane and epoxide.

The term "spacer group", also referred to as "Sp" above and below, is known to the person skilled in the art and is described in the literature, see, for example, Pure Appl. Chem. 73(5), 888 (2001) and C. Tschierske, G. Pelzl, S. Diele, Angew. Chem. 2004, 116, 6340-6368. Unless indicated otherwise, the term "spacer group" or "spacer" above and below denotes a flexible group which connects the mesogenic group and the polymerisable group(s) to one another in a polymerisable liquid-crystalline or mesogenic compound.

Preferred spacer groups Sp are selected from the formula Sp'-X', so that the radical P-Sp- corresponds to the formula P-Sp'-X'—, where Sp' denotes alkylene having 1 to 20, preferably 1 to 12, C atoms, which is optionally mono- or polysubstituted by F, Cl, Br, I or CN, and in which, in addition, one or more non-adjacent CH$_2$ groups may each be replaced, independently of one another, by —O—, —S—, —NH—, —NR$^0$—, —SiR$^{00}$R$^{000}$—, —CO—, —COO—, —OCO—, —OCO—O—, —S—CO—, —CO—S—, —NR$^{00}$—CO—O—, —O—CO—NR$^{00}$—, —NR$^{00}$—CO—NR$^{00}$—, —CH=CH— or —C≡C— in such a way that O and/or S atoms are not linked directly to one another, X' denotes —O—, —S—, —CO—, —COO—, —OCO—, —O—COO—, —CO—NR$^{00}$—, —NR$^{00}$—CO—, —NR$^{00}$—CO—NR$^{00}$—, —OCH$_2$—, —CH$_2$O—, —SCH$_2$—, —CH$_2$S—, —CF$_2$O—, —OCF$_2$—, —CF$_2$S—, —SCF$_2$—, —CF$_2$CH$_2$—, —CH$_2$CF$_2$—, —CF$_2$CF$_2$—, —CH=N—, —N=CH—, —N=N—, —CH=CR$^0$—, —CY$^2$=CY$^3$—, —C≡C—, —CH=CH—COO—, —OCO—CH=CH— or a single bond, R$^{00}$ and R$^{000}$ each, independently of one another, denote H or alkyl having 1 to 12 C atoms, and Y$^2$ and Y$^3$ each, independently of one another, denote H, F, Cl or CN.

X' is preferably —O—, —S—, —CO—, —COO—, —OCO—, —O—COO—, —CO—NR$^0$—, —NR$^0$—CO—, —NR$^0$—CO—NR$^0$— or a single bond.

Typical spacer groups Sp' are, for example, —(CH$_2$)$_{p1}$—, —(CH$_2$CH$_2$O)$_{q1}$—CH$_2$CH$_2$—, —CH$_2$CH$_2$—S—CH$_2$CH$_2$—, —CH$_2$CH$_2$—NH—CH$_2$CH$_2$— or —(SiR$^{00}$R$^{000}$—O)$_{p1}$—, in which p1 is an integer from 1 to 12, q1 is an integer from 1 to 3, and R$^{00}$ and R$^{000}$ have the meanings indicated above.

Particularly preferred groups —X'-Sp'- are —(CH$_2$)$_{p1}$—, —O—(CH$_2$)$_{p1}$—, —OCO—(CH$_2$)$_{p1}$—, —OCOO—(CH$_2$)$_{p1}$—.

Particularly preferred groups Sp' are, for example, in each case straight-chain ethylene, propylene, butylene, pentylene, hexylene, heptylene, octylene, nonylene, decylene, undecylene, dodecylene, octadecylene, ethyleneoxyethylene, methyleneoxybutylene, ethylenethioethylene, ethylene-N-methyliminoethylene, 1-methylalkylene, ethenylene, propenylene and butenylene.

Particularly preferred compounds of the formula I are those selected from the following sub-formulae:

Ia

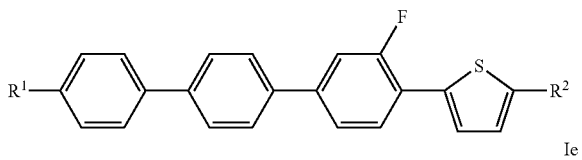

Ib

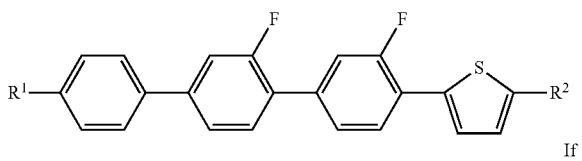

Ic

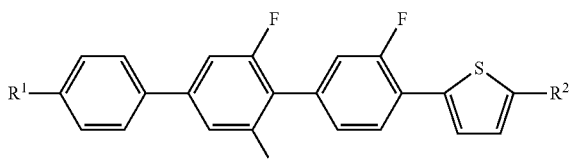

Id

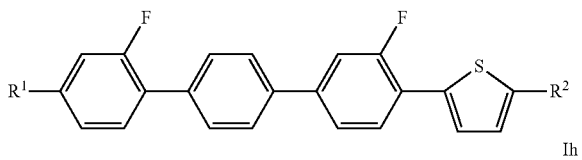

Ie

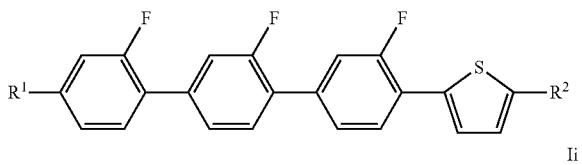

If

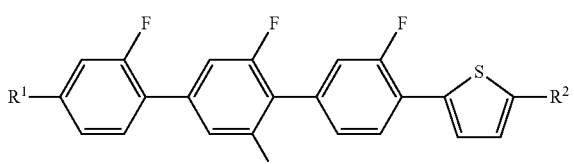

Ig

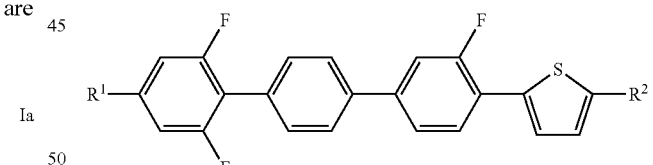

Ih

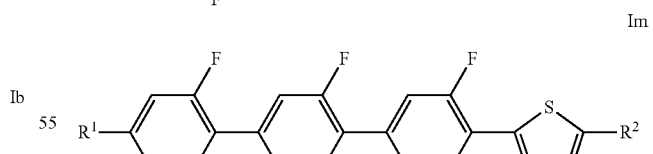

Ii

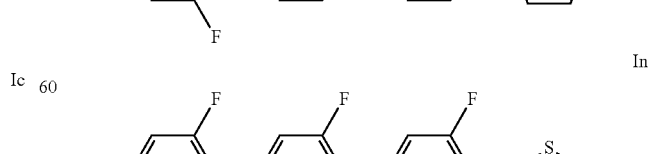

Ik

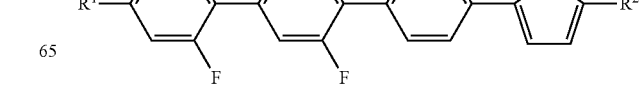

Im

In

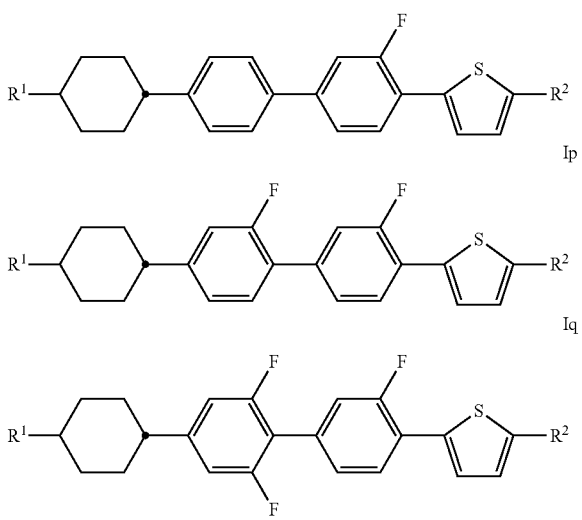

in which R¹ and R² have the meanings indicated above and below. R¹ and R² therein preferably denote optionally fluorinated alkyl, alkenyl, alkynyl or alkoxy having 1 to 12 C atoms, particularly preferably optionally fluorinated alkyl, alkenyl or alkynyl having 1 to 5 C atoms.

The compounds of the formula I can be prepared analogously to processes known to the person skilled in the art and described in standard works of organic chemistry, such as, for example, in Houben-Weyl, Methoden der organischen Chemie [Methods of Organic Chemistry], Thieme-Verlag, Stuttgart.

The compounds of the formula I are preferably synthesised, as shown by way of example in Scheme 1 below, starting from correspondingly substituted bromothiophenes 2. These are reacted with corresponding boronic acids 1 or boronic acid esters in a palladium-promoted Suzuki cross-coupling to give the compounds of the formula I.

Scheme 1: Suzuki coupling to 2-bromothiophenes 2

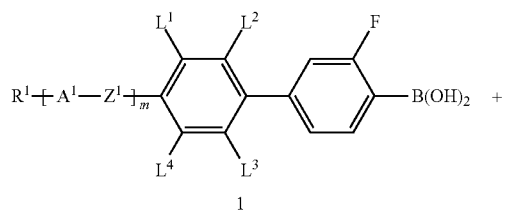

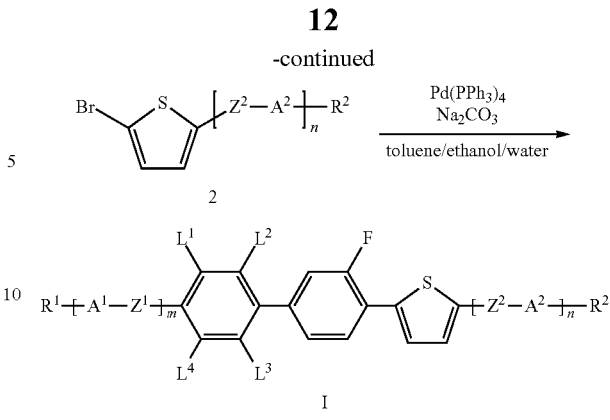

The bromothiophenes 2 are synthesised by bromination of thiophenes 3. This can be carried out by direct bromination using bromine or NBS (for example methods A and B in Scheme 2) or by bromination of a lithiothiophene intermediate (method C).

Scheme 2: Synthesis of 2-bromothiophenes 2

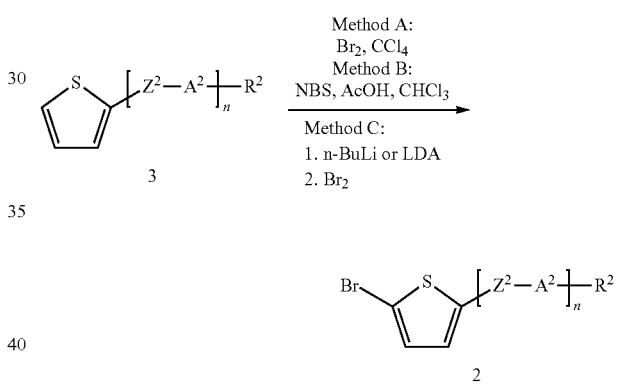

If bromothiophene 2a (2 where n=0 and R²=H) is used for the above Suzuki coupling, compounds Ia (I where n=0 and R²=H) are obtained, which can be further functionalised, as shown by way of example in Scheme 3. This functionalisation can be carried out, for example, via a lithiated intermediate. This can be reacted with numerous electrophiles. Reaction with bromine or iodine gives compounds Ib (1 where n=0 and R²=Br or I), which can be further functionalised by cross-coupling reactions (for example Suzuki, Kumada or Sonogashira couplings).

Scheme 3: Synthesis and reaction of halothiophenes Ib
(I where n = 0 and R² = Br, I)

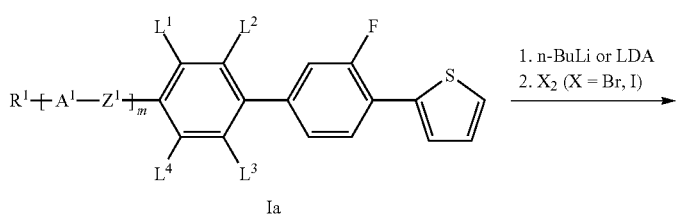

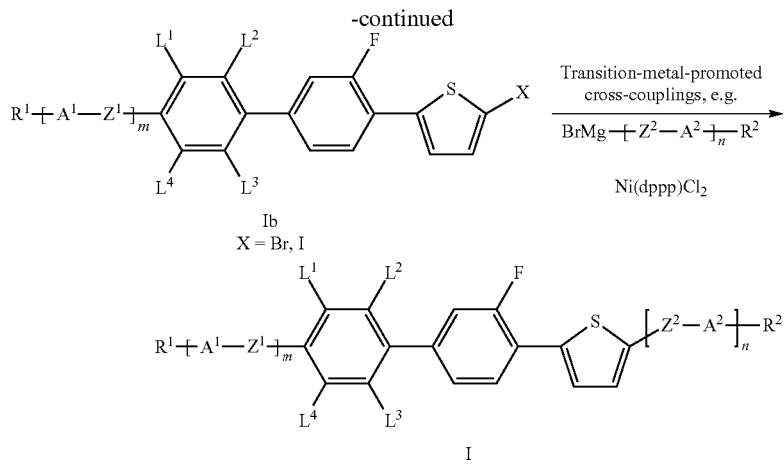

Access to the particularly preferred compounds I in which n=0 and $R^2$ denotes an alkyl radical consists in the alkylation of the lithiated compound obtained from Ia using, for example, alkyl halides or alkyl sulfates, as shown by way of example in Scheme 4.

preferred materials for obtaining the preferred compounds of the formula I containing alkenyl and alkyl substituents. The thiophenecarbaldehydes 6 are, as shown by way of example in Scheme 5, obtained by reaction of compounds 4 with DMF or N-formylmorpholine. The aldehydes can then be converted

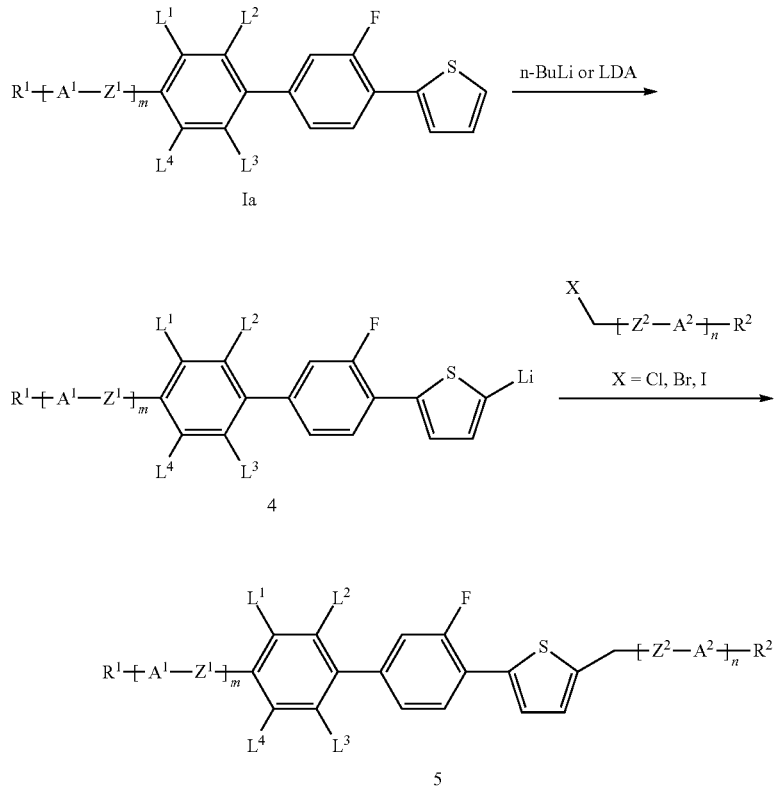

In some cases, however, these alkylations proceed with unreacted starting material Ia remaining, the separation of which may be difficult. The intermediates 6 are therefore into alkenyl-substituted thiophenes 7 in a Wittig reaction. The latter compounds can be hydrogenated to alkylthiophene derivatives 8.

Scheme 5: Formylation of lithiothiophenes 4 and reaction of thiophene-carbaldehydes 6

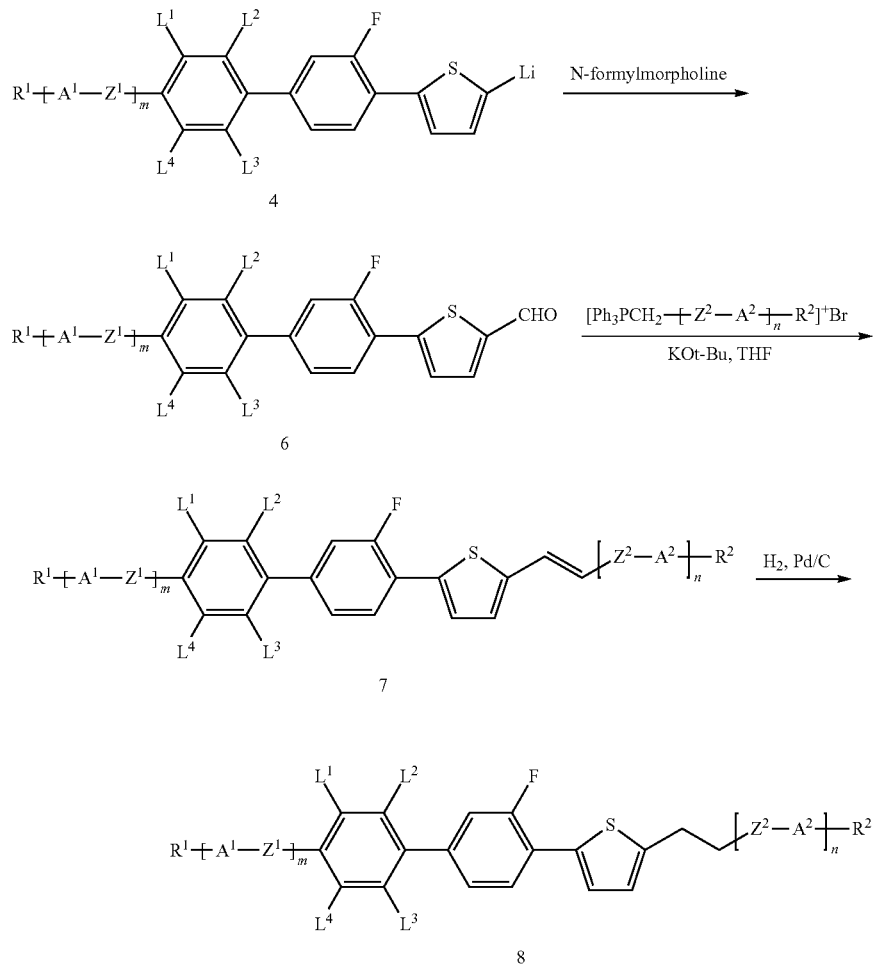

For the synthesis of compounds II in which $R^2[A^2Z^2]$— is equal to alkyl or alkenyl, 5-bromothiophene-2-carbaldehyde 9 is also a preferred starting material, as shown by way of example in Scheme 6.

Scheme 6: Synthesis of thiophenecarbaldehydes 6 from 5-bromothiophene-2-carbaldehyde (9)

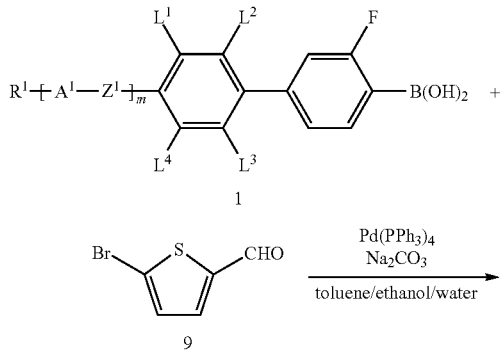

-continued

Furthermore, the roles of electrophile and nucleophile can be exchanged in the cross-couplings from Scheme 1 by reacting bromobiphenyls 10 with thiopheneboronic acids or thiophenehydroxyboronic acid salts 11, as shown by way of example in Scheme 7. The latter can be synthesised and isolated particularly simply [A. N. Cammidge, V. H. M. Goddard, H. Gopee, N. L. Harrison, D. L. Hughes, C. J. Schubert, B. M. Sutton, G. L. Watts, A. J. Whitehead, *Org. Lett.* 2006, 8, 4071-4074].

Scheme 7: Suzuki coupling to thiopheneboronic acid salts 10

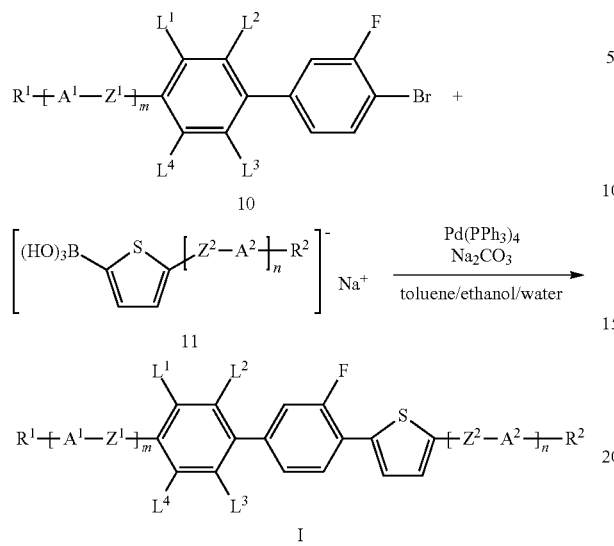

Preference is furthermore given to compounds in which n=0 and $R^2$ preferably represents an alkoxy substituent. Their synthesis requires 5-bromothiophen-2-yl ethers 2c (2 where n=0 and $R^2$=$OR^{22}$, where $R^{22}$ may adopt the same meanings and the same preferred meanings as defined under formula I, where O atoms should not be linked directly to one another, and $R^{22}$ preferably denotes alkyl). These are prepared starting from bromothiophene 2a (2 where n=0 and $R^2$=Br), as shown by way of example in Scheme 8. Firstly, the alkoxy group is introduced by reaction with an alkoxide in the presence of copper(I) bromide [M. A. Keegstra, T. H. A. Peters, L. Brandsma, *Tetrahedron* 1992, 48, 3633-3652]. The thiophenes 12 obtained in this way are then brominated to give the compounds 2c (2 where n=0 and $R^2$=$OR^{22}$, where $R^{22}$ may adopt the same meanings and the same preferred meanings as defined under formula I, where O atoms should not be linked directly to one another, and $R^{22}$ preferably denotes alkyl) and reacted further as shown in Scheme 1.

Scheme 8: Synthesis of 5-bromothiophen-2-yl ethers 2c
(2 where n = 0 and $R^2$ = $OR^{22}$, where $R^{22}$ may adopt the same meanings and the same preferred meanings as defined under formula I, where O atoms should not be linked directly to one another, and $R^{22}$ preferably denotes alkyl)

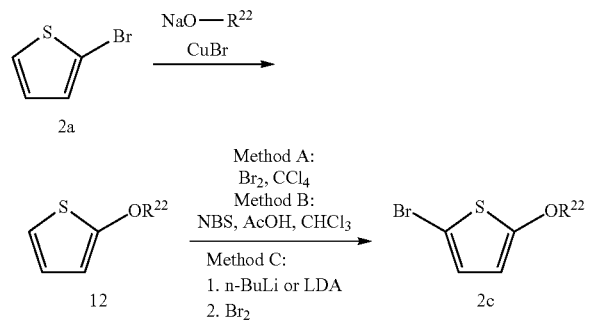

Preference is furthermore given to compounds of type I in which —[$Z_2$-$A_2$]$_n$-$R_2$ denotes fluorine (=Id). These are advantageously prepared from compounds Ia (I where n=0 and $R^2$=H), as shown by way of example in Scheme 9. To this end, the lithiated intermediate 4 formed initially is scavenged using N-fluorobenzenesulfonamide.

Scheme 9: Fluorination of compounds Ia
(I where n = 0 and $R^2$ = H)

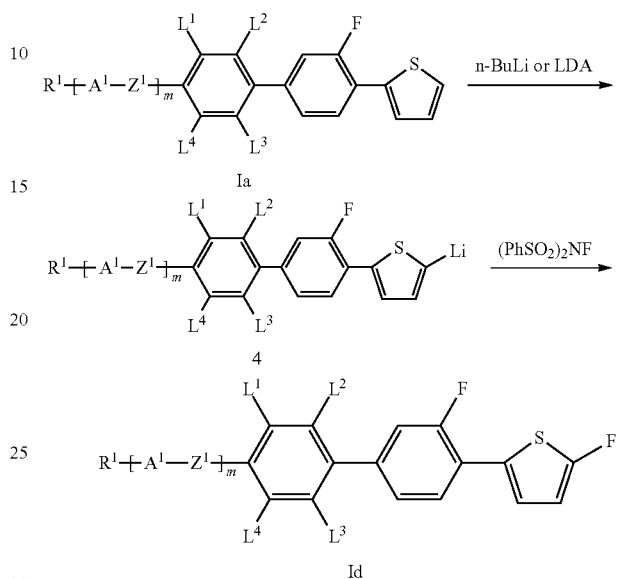

The present invention furthermore relates to the processes described above and below and to the novel intermediates produced or used therein, and to the use thereof for the preparation of compounds of the formula I according to the invention.

Particularly preferred LC media according to the invention are mentioned below:

LC medium which additionally comprises one or more compounds of the formulae II and/or III:

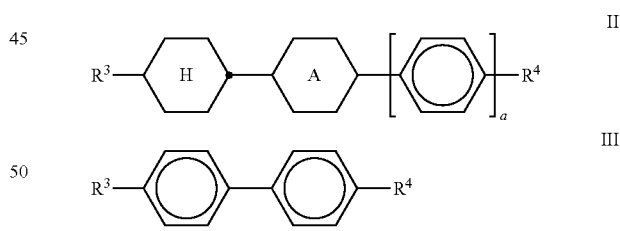

in which

A denotes 1,4-phenylene or trans-1,4-cyclohexylene, a is 0 or 1, $R^3$ denotes alkenyl having 2 to 9 C atoms, and $R^4$ denotes alkyl having 1 to 12 C atoms, where, in addition, one or two non-adjacent $CH_2$ groups may be replaced by —O—, —CH=CH—, —CO—, —OCO— or —COO— in such a way that O atoms are not linked directly to one another, and preferably denotes alkyl having 1 to 12 C atoms or alkenyl having 2 to 9 C atoms.

The compounds of the formula II are preferably selected from the group consisting of the following formulae:

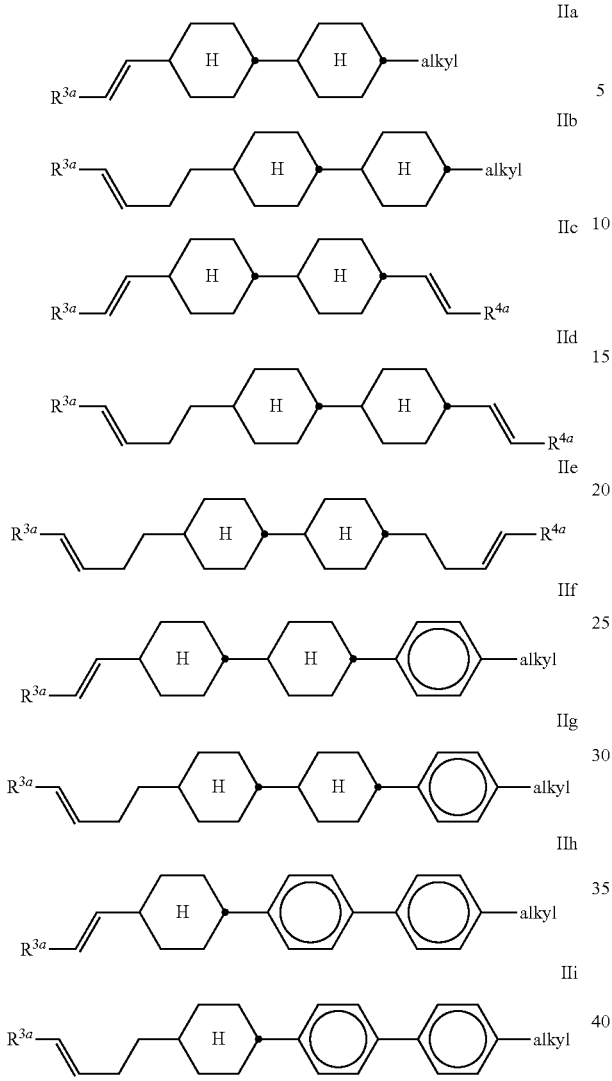

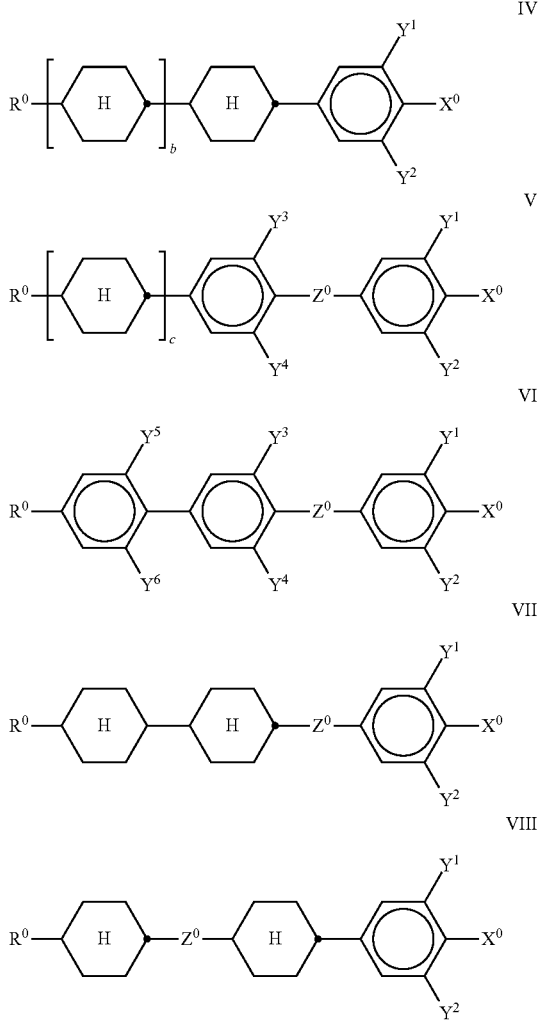

in which $R^{3a}$ and $R^{4a}$ each, independently of one another, denote H, $CH_3$, $C_2H_5$ or $C_3H_7$, and "alkyl" denotes a straight-chain alkyl group having 1 to 8, preferably 1, 2, 3, 4 or 5, C atoms. Particular preference is given to compounds of the formulae IIa and IIf, in particular in which $R^{3a}$ denotes H or $CH_3$, preferably H, and compounds of the formula IIc, in particular in which $R^{3a}$ and $R^{4a}$ denote H, $CH_3$ or $C_2H_5$.

The compounds of the formula III are preferably selected from the group consisting of the following formulae:

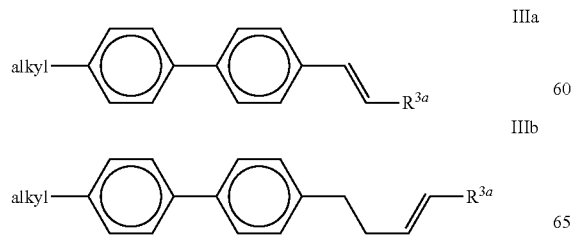

in which "alkyl" and $R^{3a}$ have the meanings indicated above, and $R^{3a}$ preferably denotes H or $CH_3$. Particular preference is given to compounds of the formula IIIb;

LC medium which additionally comprises one or more compounds selected from the group consisting of the following formulae:

in which
$R^0$ denotes an alkyl or alkoxy radical having 1 to 15 C atoms, where, in addition, one or more $CH_2$ groups in these radicals may each be replaced, independently of one another, by —C≡C—, —$CF_2O$—, —CH=CH—,

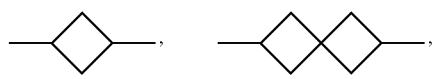

—O—, —CO—O— or —O—CO— in such a way that O atoms are not linked directly to one another, and in which, in addition, one or more H atoms may be replaced by halogen, $X^0$ denotes F, Cl, CN, $SF_5$, SCN, NCS, a halogenated alkyl radical, halogenated alkenyl radical, halogenated alkoxy radical or halogenated alkenyloxy radical, each having up to 6 C atoms, $Y^{1-6}$ each, independently of one another, denote H or F, $Z^0$ denotes —$C_2H_4$—, —$(CH_2)_4$—, —CH=CH—, —CF=CF—, —$C_2F_4$—, —$CH_2CF_2$—, —$CF_2CH_2$—, —$CH_2O$—, —$OCH_2$—, —COO—, —$CF_2O$— or —$OCF_2$—, in the formulae V and VI also a single bond, and b and c each, independently of one another, denote 0 or 1.

In the compounds of the formulae IV to VIII, $X^0$ preferably denotes F or $OCF_3$, furthermore $OCHF_2$, $CF_3$, $CF_2H$, Cl, OCH=$CF_2$. $R^0$ is preferably straight-chain alkyl or alkenyl, each having up to 6 C atoms.

The compounds of the formula IV are preferably selected from the group consisting of the following formulae:

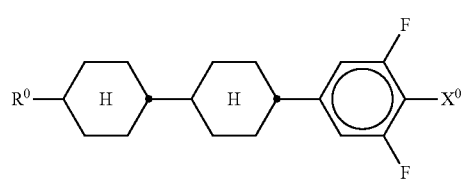

IVa

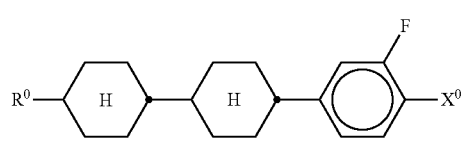

IVb

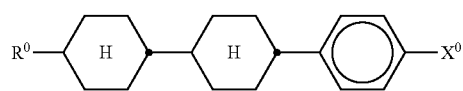

IVc

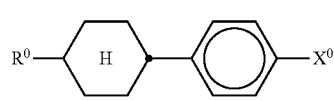

IVd

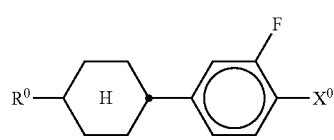

IVe

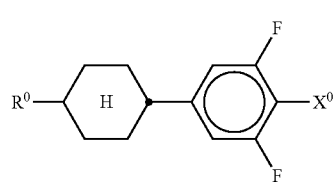

IVf in which $R^0$ and $X^0$ have the meanings indicated above.

Preferably, $R^0$ in formula IV denotes alkyl having 1 to 8 C atoms and $X^0$ denotes F, Cl, $OCHF_2$ or $OCF_3$, furthermore OCH=$CF_2$. In the compound of the formula IVb, $R^0$ preferably denotes alkyl or alkenyl. In the compound of the formula IVd, $X^0$ preferably denotes Cl, furthermore F.

The compounds of the formula V are preferably selected from the group consisting of the following formulae:

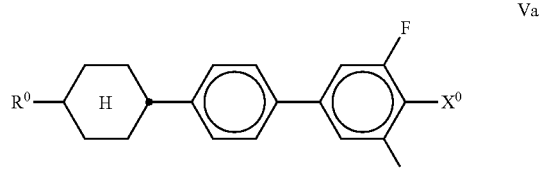

Va

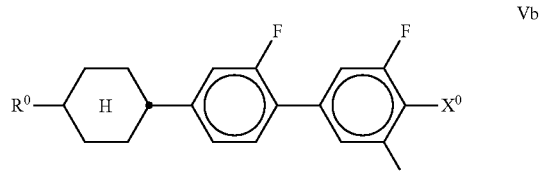

Vb

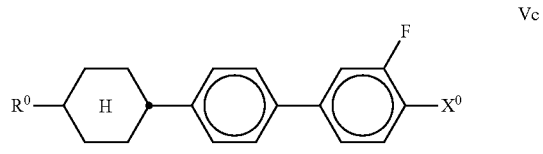

Vc

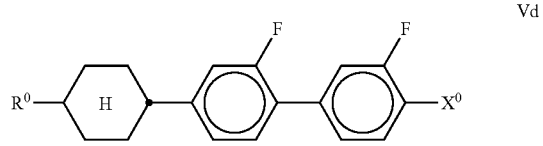

Vd

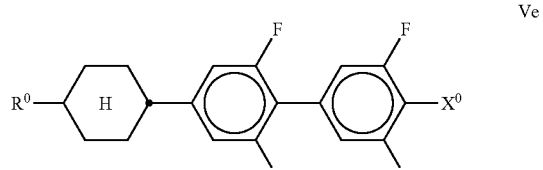

Ve

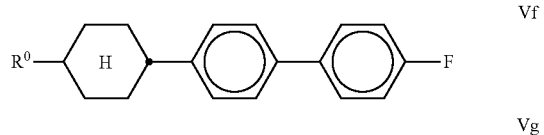

Vf

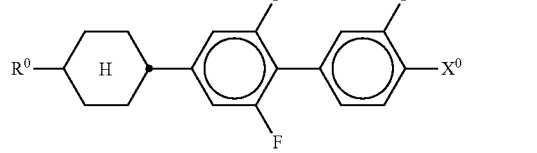

Vg in which $R^0$ and $X^0$ have the meanings indicated above. Preferably, $R^0$ in formula V denotes alkyl having 1 to 8 C atoms and $X^0$ denotes F;

LC medium which comprises one or more compounds of the formula VI-1:

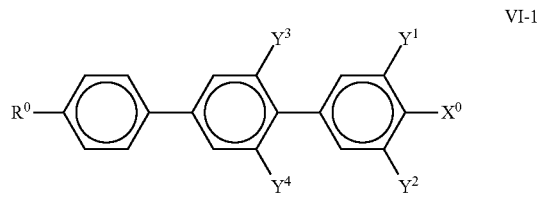

VI-1 particularly preferably those selected from the group consisting of the following formulae:

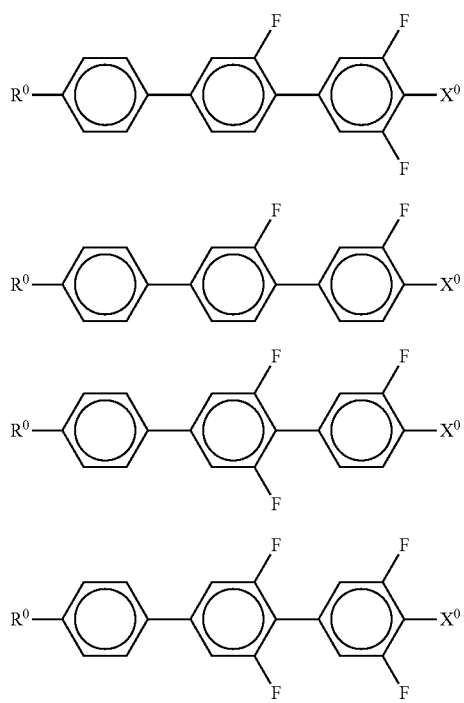

in which $R^0$ and $X^0$ have the meanings indicated above. Preferably, $R^0$ in formula VI denotes alkyl having 1 to 8 C atoms and $X^0$ denotes F, furthermore $OCF_3$.

LC medium which comprises one or more compounds of the formula VI-2:

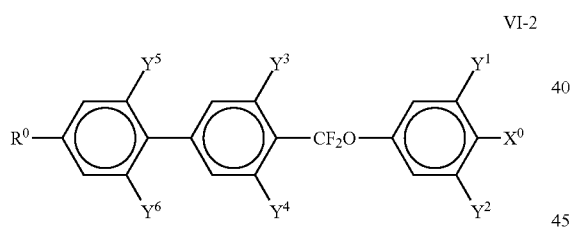

particularly preferably those selected from the group consisting of the following formulae:

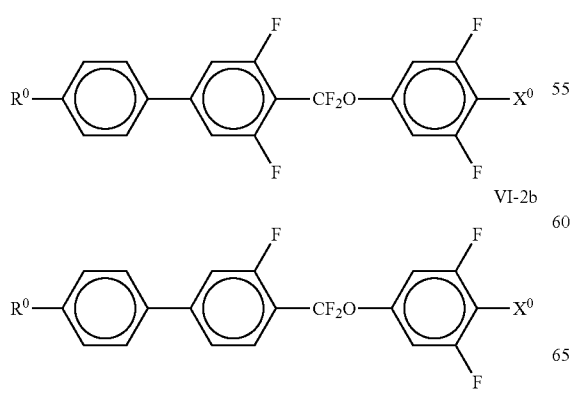

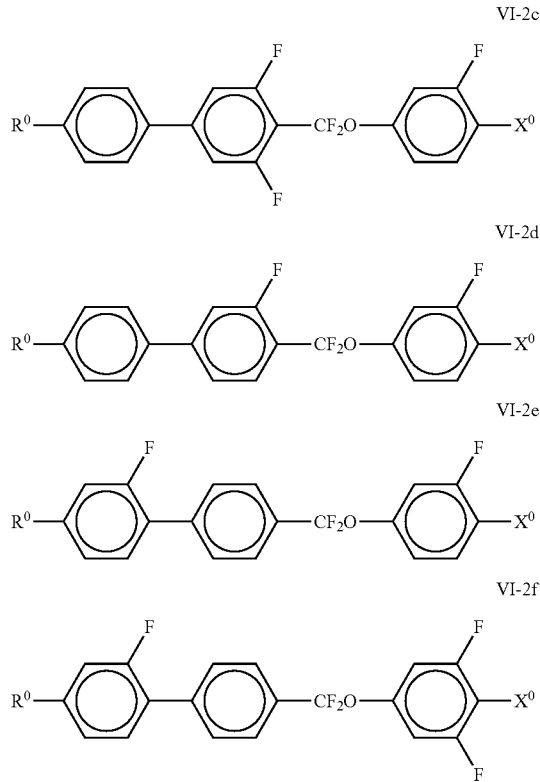

in which $R^0$ and $X^0$ have the meanings indicated above.

Preferably, $R^0$ in formula VI denotes alkyl having 1 to 8 C atoms and $X^0$ denotes F;

LC medium which preferably comprises one or more compounds of the formula VII in which $Z^0$ denotes —$CF_2O$—, —$CH_2CH_2$— or —COO—, particularly preferably those selected from the group consisting of the following formulae:

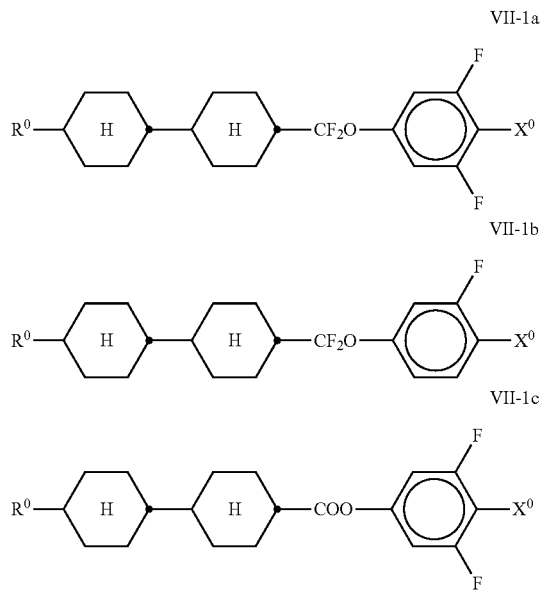

-continued

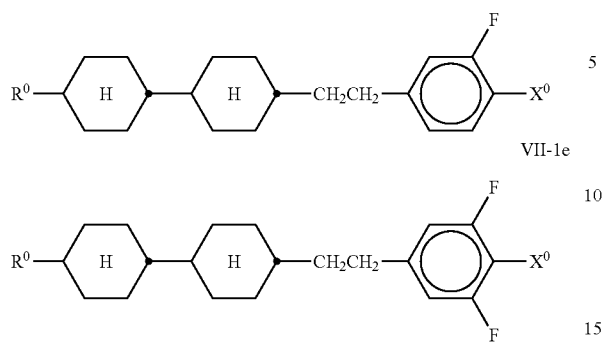

in which $R^0$ and $X^0$ have the meanings indicated above. Preferably, $R^0$ in formula VII denotes alkyl having 1 to 8 C atoms and $X^0$ denotes F, furthermore $OCF_3$.

The compounds of the formula VIII are preferably selected from the group consisting of the following formulae:

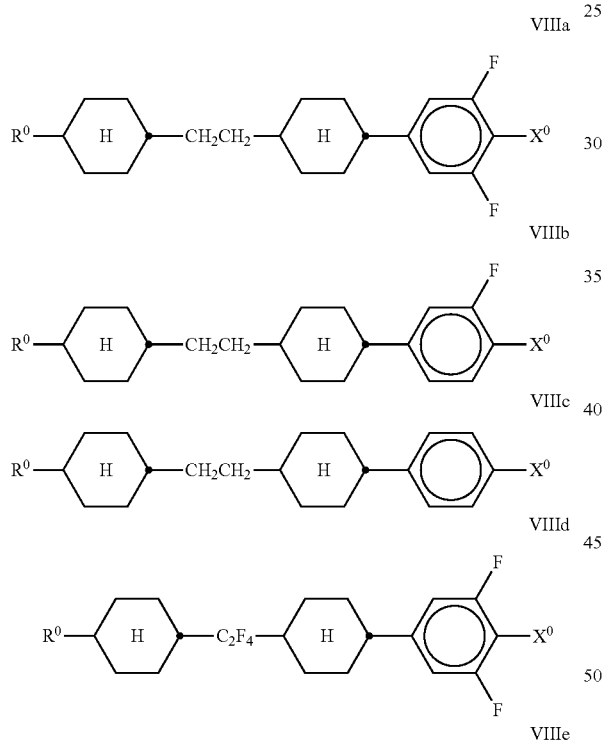

in which $R^0$ and $X^0$ have the meanings indicated above. $R^0$ preferably denotes a straight-chain alkyl radical having 1 to 8 C atoms. $X^0$ preferably denotes F.

LC medium which additionally comprises one or more compounds of the following formula:

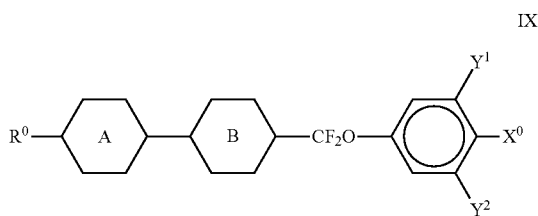

in which $R^0$, $X^0$, $Y^1$ and $Y^2$ have the meaning indicated above, and

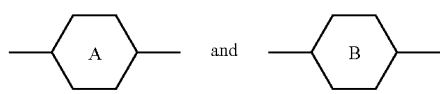

each, independently of one another, denote

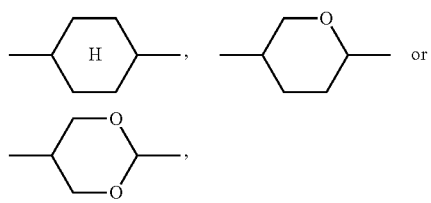

where the rings A and B do not both simultaneously denote cyclohexylene.

The compounds of the formula IX are preferably selected from the group consisting of the following formulae:

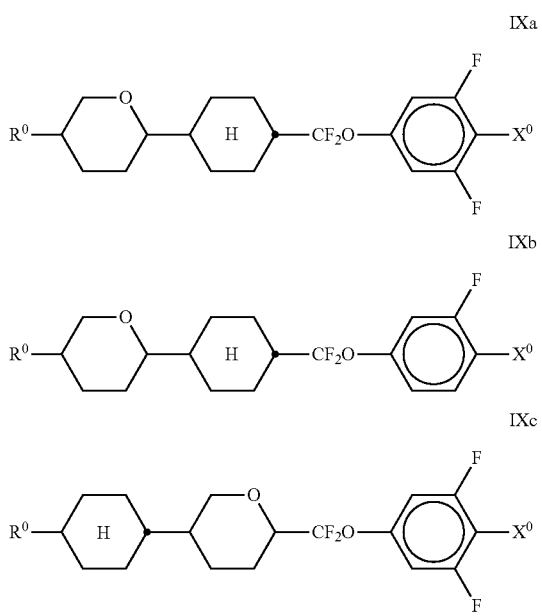

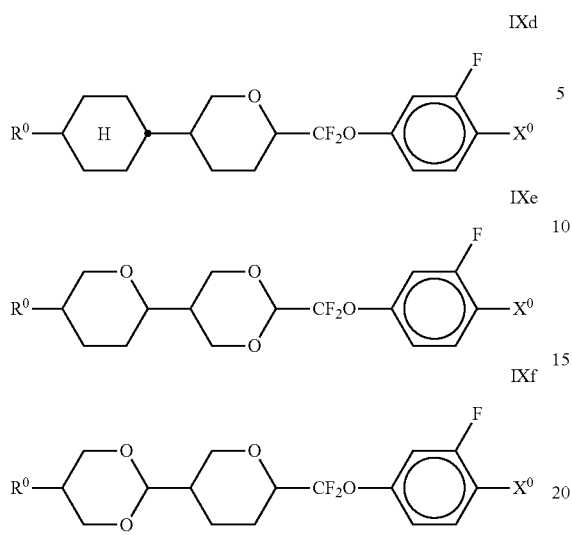

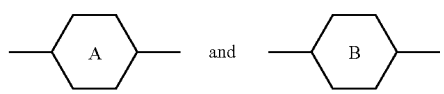

each, independently of one another, denote

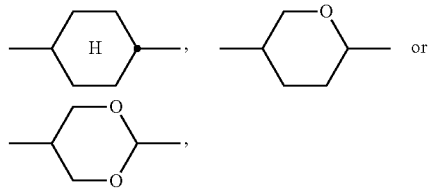

The compounds of the formulae X and XI are preferably selected from the group consisting of the following formulae:

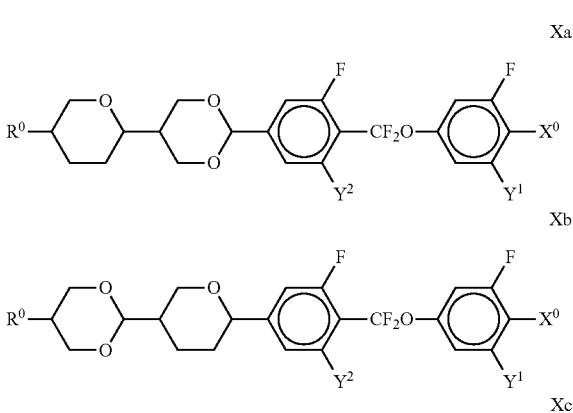

in which $R^0$ and $X^0$ have the meanings indicated above. Preferably, $R^0$ denotes alkyl having 1 to 8 C atoms and $X^0$ denotes F. Particular preference is given to compounds of the formula IXa;

LC medium which additionally comprises one or more compounds selected from the group consisting of the following formulae:

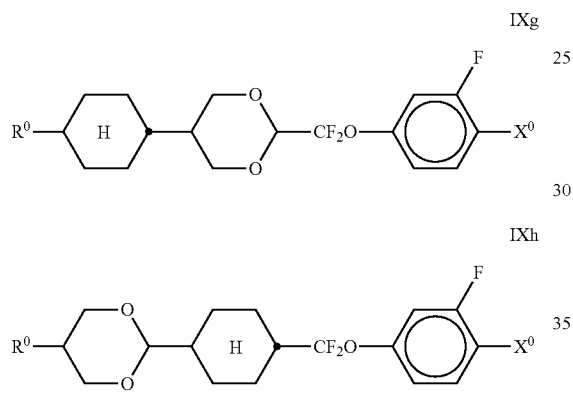

in which $R^0$, $X^0$ and $Y^{1-4}$ have the meanings indicated above, and

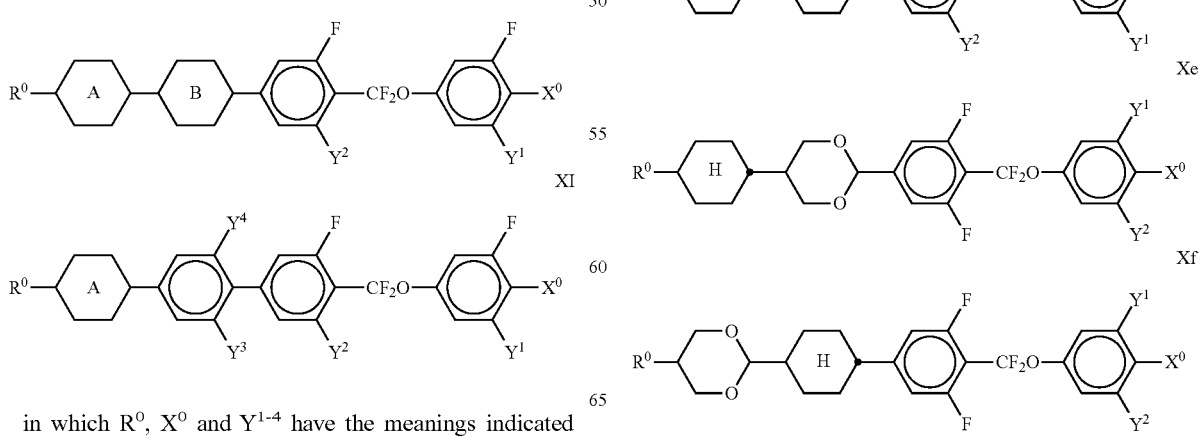

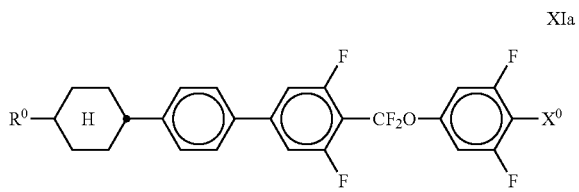
XIa

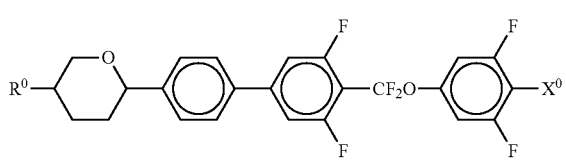
XIb in which $R^0$ and $X^0$ have the meanings indicated above. Preferably, $R^0$ denotes alkyl having 1 to 8 C atoms and $X^0$ denotes F. Particularly preferred compounds are those in which $Y^1$ denotes F and $Y^2$ denotes H or F, preferably F;

LC medium which additionally comprises one or more compounds of the following formula:

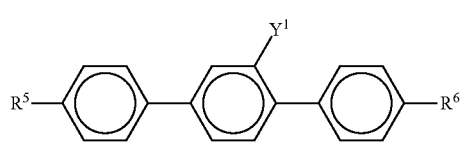
XII in which $R^5$ and $R^6$ each, independently of one another, denote n-alkyl, alkoxy, oxaalkyl, fluoroalkyl or alkenyl, each having up to 9 C atoms, and preferably each, independently of one another, denote alkyl having 1 to 8 C atoms. $Y^1$ denotes H or F.

Preferred compounds of the formula XII are those selected from the group consisting of the following formulae:

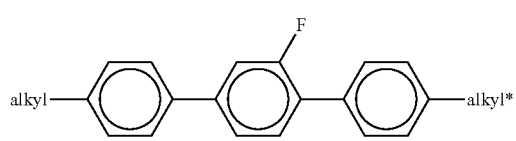
XIIa

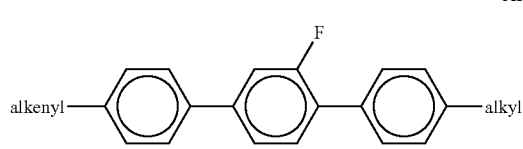
XIIb

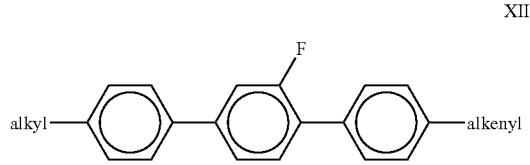
XIIc

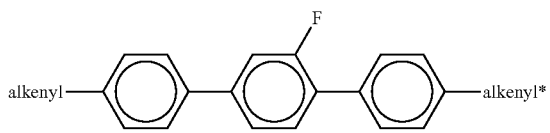
XIId in which alkyl and alkyl* each, independently of one another, denote a straight-chain alkyl radical having 1 to 6 C atoms, and alkenyl and alkenyl* each, independently of one another, denote a straight-chain alkenyl radical having 2 to 6 C atoms.

LC medium which additionally comprises one or more compounds selected from the group consisting of the following formulae:

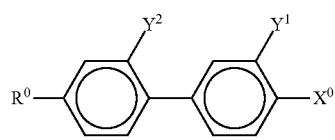
XIII

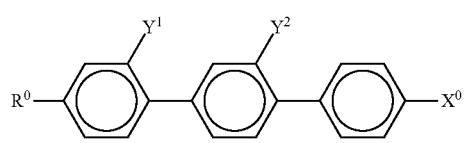
XIV

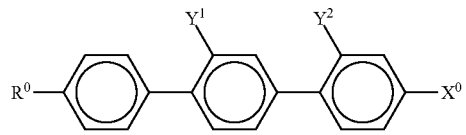
XV

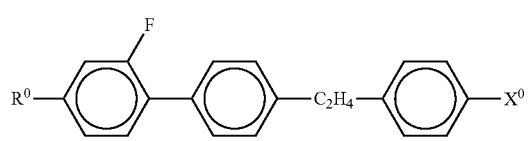
XVI in which $R^0$, $X^0$, $Y^1$ and $Y^2$ have the meanings indicated above. Preferably, $R^0$ denotes alkyl having 1 to 8 C atoms and $X^0$ denotes F or Cl;

the compounds of the formulae XIII and XIV are preferably selected from the group consisting of the following formulae:

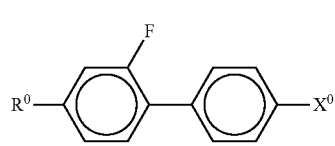
XIIIa

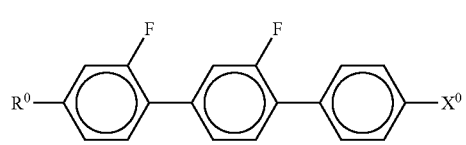
XIVa

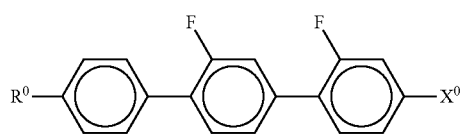

XVa in which R⁰ and X⁰ have the meanings indicated above. R⁰ preferably denotes alkyl having 1 to 8 C atoms. In the compounds of the formula XIII, X⁰ preferably denotes F or Cl.

LC medium which additionally comprises one or more compound of the formulae D1 and/or D2:

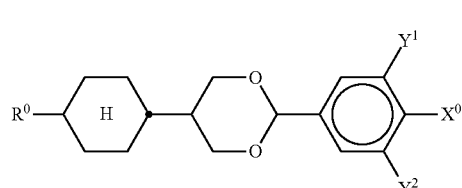

D1

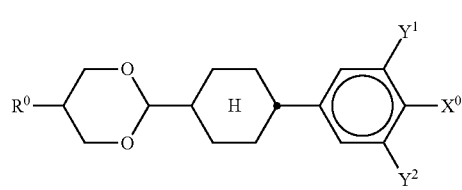

D2 in which $Y^1$, $Y^2$, $R^0$ and $X^0$ have the meaning indicated above. Preferably, $R^0$ denotes alkyl having 1 to 8 C atoms and $X^0$ denotes F. Particular preference is given to compounds of the following formulae:

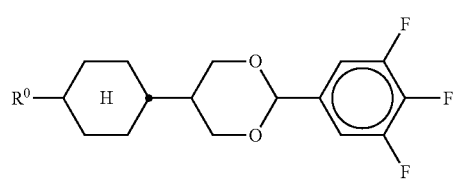

D1-1

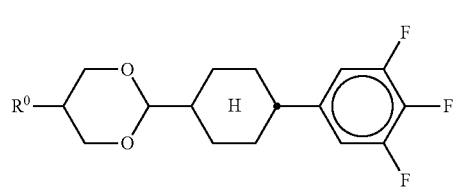

D2-1 in which $R^0$ has the meanings indicated above and preferably denotes straight-chain alkyl having 1 to 6 C atoms, in particular $C_2H_5$, $n\text{-}C_3H_7$ or $n\text{-}C_5H_{11}$.

LC medium which additionally comprises one or more compounds of the following formula:

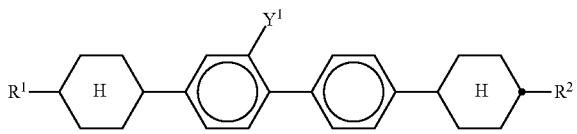

XVII in which $Y^1$, $R^1$ and $R^2$ have the meaning indicated above. $R^1$ and $R^2$ preferably each, independently of one another, denote alkyl having 1 to 8 C atoms;

LC medium which additionally comprises one or more compounds of the following formula:

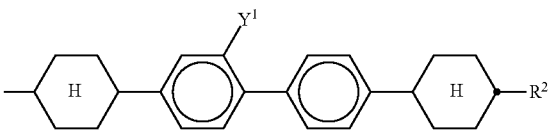

XVIII in which $X^0$, $Y^1$ and $Y^2$ have the meanings indicated above, and "alkenyl" denotes $C_{2-7}$-alkenyl. Particular preference is given to compounds of the following formula:

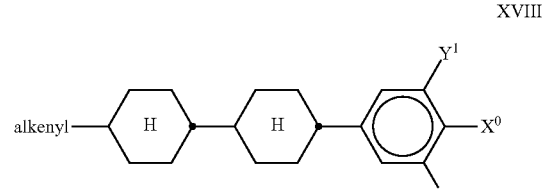

XVIIIa in which $R^{3a}$ has the meaning indicated above and preferably denotes H;

LC medium which additionally comprises one or more tetracyclic compounds selected from the group consisting of the formulae XIX to XXV:

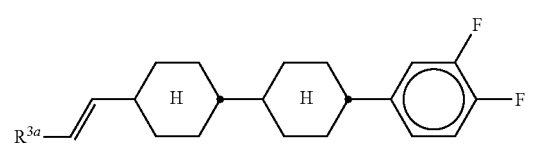

XIX

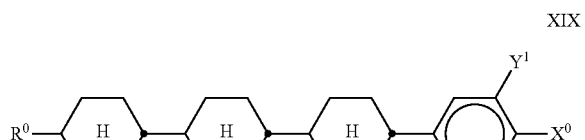

XX

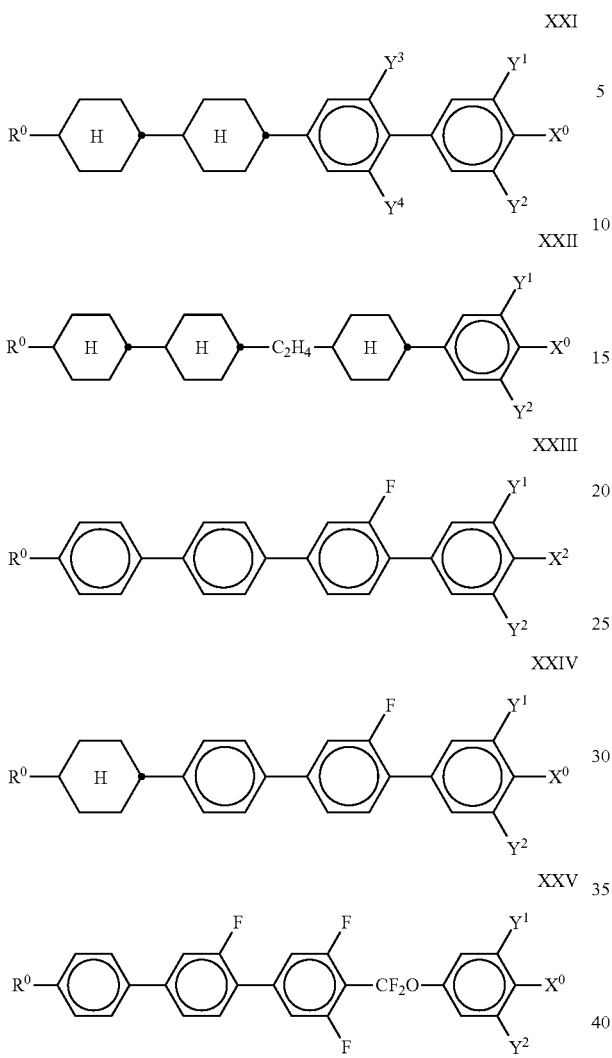

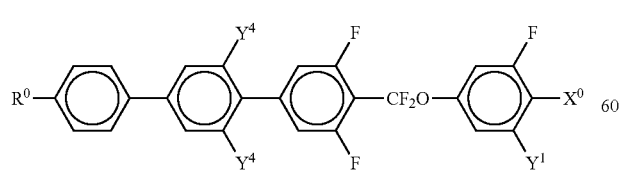

in which $Y^{1-4}$, $R^0$ and $X^0$ each, independently of one another, have one of the meanings indicated above. $X^0$ is preferably F, Cl, $CF_3$, $OCF_3$ or $OCHF_2$. $R^0$ preferably denotes alkyl, alkoxy, oxaalkyl, fluoroalkyl or alkenyl, each having up to 8 C atoms.

LC medium which additionally comprises one or more compounds of the following formula:

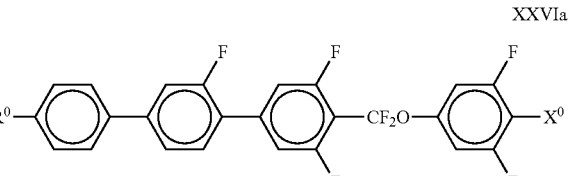

in which $R^0$, $X^0$ and $Y^{1-4}$ have the meanings indicated above. Particular preference is given to compounds of the following formula:

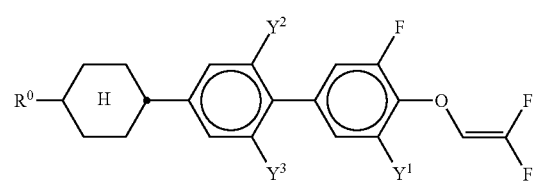

in which $X^0$ particularly preferably denotes F.

LC medium which additionally comprises one or more compounds of the following formula:

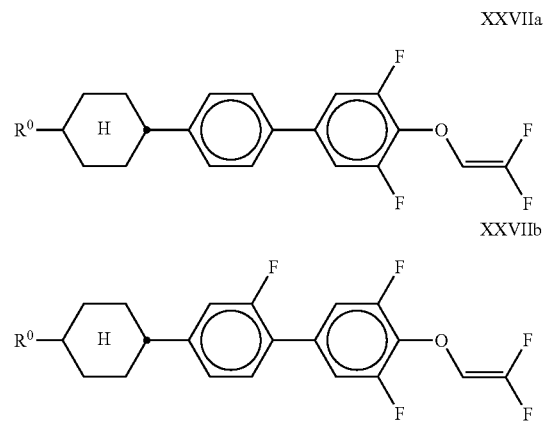

in which $R^0$ and $Y^{1-3}$ have the meanings indicated above. Particular preference is given to compounds of the following formulae:

in which $R^0$ has the meaning indicated above and preferably denotes alkyl, alkoxy, oxaalkyl, fluoroalkyl or alkenyl, each having up to 8 C atoms.

LC medium which additionally comprises one or more compounds of the following formula:

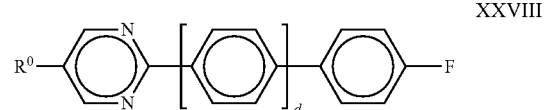

in which $R^0$ has the meaning indicated above and is preferably straight-chain alkyl having 2-5 C atoms, and d denotes 0 or 1, preferably 1, Preferred mixtures comprise 3-30% by weight, in particular 5-20% by weight, of this (these) compound(s).

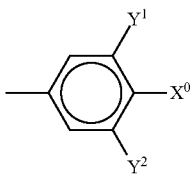

is preferably

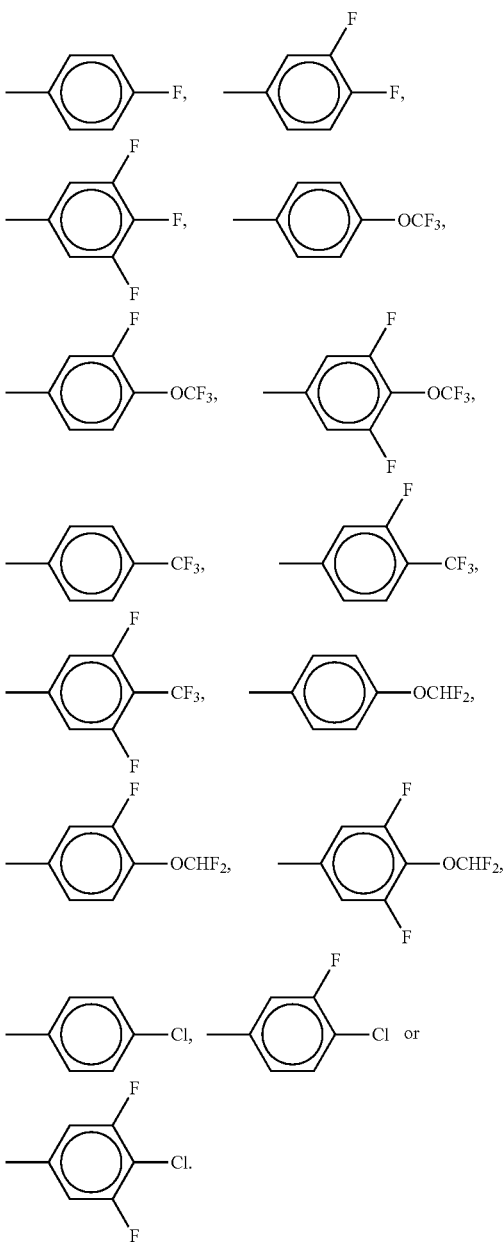

$R^0$ is preferably straight-chain alkyl or alkenyl having 2 to 7 C atoms;

$X^0$ is preferably F, furthermore $OCF_3$, Cl or $CF_3$;

the medium preferably comprises one, two or three compounds of the formula I;

the medium preferably comprises one or more compounds selected from the group of the compounds of the formulae I, II, III, VI-2, XI, XII, XIII, XIV, XXIV, XXV, XXVI, XXVII;

the medium preferably comprises in each case one or more compounds of the formulae VI-2, XI and XXVI;

the medium preferably comprises 1-25% by weight, preferably 1-20% by weight, of compounds of the formula I;

the proportion of compounds of the formulae II-XXVIII in the mixture as a whole is preferably 20 to 99% by weight;

the medium preferably comprises 25-80% by weight, particularly preferably 30-70% by weight, of compounds of the formulae II and/or III;

the medium preferably comprises 20-70% by weight, particularly preferably 25-60% by weight, of compounds of the formula IIa, in particular in which $R^{3a}$ denotes H;

the medium preferably comprises 2-20% by weight, particularly preferably 3-15% by weight, of compounds of the formula VI-2;

the medium comprises 2-20% by weight, particularly preferably 3-15% by weight, of compounds of the formula XI;

the medium preferably comprises 1-20% by weight, particularly preferably 2-15% by weight, of compounds of the formula XXIV;

the medium preferably comprises 1-25% by weight, particularly preferably 2-20% by weight, of compounds of the formula XXVI;

the medium preferably comprises 1-35% by weight, particularly preferably 5-30% by weight, of compounds of the formula XXVII.

It has been found that even a relatively small proportion of compounds of the formula I mixed with conventional liquid-crystal materials, but in particular with one or more compounds of the formulae II to XXVIII, results in a significant increase in the light stability and in low birefringence values, with broad nematic phases having low smectic-nematic transition temperatures being observed at the same time, improving the storage stability. The mixtures simultaneously exhibit very low threshold voltages and very good values for the VHR on exposure to UV.

The term "alkyl" or "alkyl*" in this application encompasses straight-chain and branched alkyl groups having 1-7 carbon atoms, in particular the straight-chain groups methyl, ethyl, propyl, butyl, pentyl, hexyl and heptyl. Groups having 1-6 carbon atoms are generally preferred.

The term "alkenyl" or "alkenyl*" in this application encompasses straight-chain and branched alkenyl groups having 2-7 carbon atoms, in particular the straight-chain groups. Preferred alkenyl groups are $C_2$-$C_7$-1E-alkenyl, $C_4$-$C_7$-3E-alkenyl, $C_5$-$C_7$-4-alkenyl, $C_6$-$C_7$-5-alkenyl and $C_7$-6-alkenyl, in particular $C_2$-$C_7$-1E-alkenyl, $C_4$-$C_7$-3E-alkenyl and $C_5$-$C_7$-4-alkenyl. Examples of particularly preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 carbon atoms are generally preferred.

The term "fluoroalkyl" in this application encompasses straight-chain groups containing at least one fluorine atom, preferably a terminal fluorine, i.e., fluoromethyl, 2-fluoroethyl, 3-fluoropropyl, 4-fluorobutyl, 5-fluoropentyl, 6-fluorohexyl and 7-fluoroheptyl. However, other positions of the fluorine are not excluded.

The term "oxaalkyl" or "alkoxy" in this application encompasses straight-chain radicals of the formula $C_nH_{2n+1}$—O—

(CH$_2$)$_m$, in which n and m each, independently of one another, denote 1 to 6. m may also denote 0. Preferably, n=1 and m=1-6 or m=0 and n=1-3.

If R$^0$ in the formulae above and below denotes an alkyl radical and/or an alkoxy radical, this may be straight-chain or branched. It is preferably straight-chain, has 2, 3, 4, 5, 6 or 7 C atoms and accordingly preferably denotes ethyl, propyl, butyl, pentyl, hexyl, heptyl, ethoxy, propoxy, butoxy, pentoxy, hexyloxy or heptyloxy, furthermore methyl, octyl, nonyl, decyl, undecyl, dodecyl, tridecyl, tetradecyl, pentadecyl, methoxy, octoxy, non-oxy, decoxy, undecoxy, dodecoxy, tridecoxy or tetradecoxy.

Oxaalkyl preferably denotes straight-chain 2-oxapropyl (=methoxymethyl), 2-(=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, 2-, 3-, 4-, 5-, 6-, 7-, 8- or 9-oxadecyl.

If R$^0$ denotes an alkyl radical in which a CH$_2$ group has been replaced by —CH═CH—, this may be straight-chain or branched. It is preferably straight-chain and has 2 to 10 C atoms. Accordingly, it denotes, in particular, vinyl, prop-1- or -2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl, oct-1-, -2-, -3-, -4-, -5-, -6- or -7-enyl, non-1-, -2-, -3-, -4-, -5-, -6-, -7- or -8-enyl, dec-1-, -2-, -3-, -4-, -5-, -6-, -7-, -8- or -9-enyl. These radicals may also be mono- or polyhalogenated.

If R$^0$ denotes an alkyl or alkenyl radical which is at least monosubstituted by halogen, this radical is preferably straight-chain and halogen is preferably F or Cl. In the case of polysubstitution, halogen is preferably F. The resultant radicals also include perfluorinated radicals. In the case of monosubstitution, the fluorine or chlorine substituent may be in any desired position, but is preferably in the ω-position.

In the formulae above and below, X$^0$ is preferably F, Cl or a mono- or polyfluorinated alkyl or alkoxy radical having 1, 2 or 3 C atoms or a mono- or polyfluorinated alkenyl radical having 2 or 3 C atoms. X$^0$ is particularly preferably F, Cl, CF$_3$, CHF$_2$, OCF$_3$, OCHF$_2$, OCFHCF$_3$, OCFHCHF$_2$, OCFHCHF$_2$, OCF$_2$CH$_3$, OCF$_2$CHF$_2$, OCF$_2$CHF$_2$, OCF$_2$CF$_2$CHF$_2$, OCF$_2$CF$_2$CH$_2$F, OCFHCF$_2$CF$_3$, OCFHCF$_2$CHF$_2$, OCH═CF$_2$, OCF═CF$_2$, OCF$_2$CHFCF$_3$, OCF$_2$CF$_2$CF$_3$, OCF$_2$CF$_2$CClF$_2$, OCClFCF$_2$CF$_3$, CF═CF$_2$, CF═CHF or CH═CF$_2$, very particularly preferably F or OCF$_3$.

Through a suitable choice of the meanings of R$^0$ and X$^0$, the addressing times, the threshold voltage, the steepness of the transmission characteristic lines, etc., can be modified in the desired manner. For example, 1E-alkenyl radicals, 3E-alkenyl radicals, 2E-alkenyloxy radicals and the like generally result in shorter addressing times, improved nematic tendencies and a higher ratio between the elastic constants k$_{33}$ (bend) and k$_{11}$ (splay) compared with alkyl and alkoxy radicals. 4-Alkenyl radicals, 3-alkenyl radicals and the like generally give lower threshold voltages and lower values of k$_{33}$/k$_{11}$ compared with alkyl and alkoxy radicals. The mixtures according to the invention are distinguished, in particular, by high K$_1$ values and thus have significantly faster response times than the mixtures from the prior art.

The optimum mixing ratio of the compounds of the above-mentioned formulae depends substantially on the desired properties, on the choice of the components of the above-mentioned formulae and on the choice of any further components that may be present.

Suitable mixing ratios within the range indicated above can easily be determined from case to case.

The total amount of compounds of the above-mentioned formulae in the mixtures according to the invention is not crucial. The mixtures can therefore comprise one or more further components for the purposes of optimisation of various properties. However, the observed effect on the desired improvement in the properties of the mixture is generally greater, the higher the total concentration of compounds of the above-mentioned formulae.

In a particularly preferred embodiment, the media according to the invention comprise compounds of the formulae IV to VIII in which X$^0$ denotes F, OCF$_3$, OCHF$_2$, OCH═CF$_2$, OCF═CF$_2$ or OCF$_2$—CF$_2$H. A favourable synergistic action with the compounds of the formula I results in particularly advantageous properties. In particular, mixtures comprising compounds of the formulae I, VI and XI are distinguished by their low threshold voltages.

The individual compounds of the above-mentioned formulae and the sub-formulae thereof which can be used in the media according to the invention are either known or can be prepared analogously to the known compounds.

The invention also relates to electro-optical displays, such as, for example, TN, STN, TFT, OCB, IPS, FFS or MLC displays, having two plane-parallel outer plates, which, together with a frame, form a cell, integrated non-linear elements for switching individual pixels on the outer plates, and a nematic liquid-crystal mixture having positive dielectric anisotropy and high specific resistance located in the cell, which contain media of this type, and to the use of these media for electro-optical purposes.

The liquid-crystal mixtures according to the invention enable a significant broadening of the available parameter latitude. The achievable combinations of clearing point, viscosity at low temperature, thermal and UV stability and high optical anisotropy are far superior to previous materials from the prior art.

The mixtures according to the invention are particularly suitable for mobile applications and high-Δn TFT applications, such as, for example, PDAs, notebooks, LCD TVs and monitors.

The liquid-crystal mixtures according to the invention, with retention of the nematic phase down to −20° C. and preferably down to −30° C., particularly preferably down to −40° C., and of the clearing point ≧70° C., preferably ≧75° C., simultaneously enable rotational viscosities γ$_1$ of ≦100 mPa·s, particularly preferably ≦70 mPa·s, to be achieved, enabling excellent MLC displays having fast response times to be obtained.

The dielectric anisotropy Δ∈ of the liquid-crystal mixtures according to the invention is preferably ≧+5, particularly preferably ≧+10. In addition, the mixtures are characterised by low operating voltages. The threshold voltage of the liquid-crystal mixtures according to the invention is preferably ≦1.5 V, in particular ≦1.2 V.

The birefringence Δn of the liquid-crystal mixtures according to the invention is preferably ≧0.10, particularly preferably ≧0.11.

The nematic phase range of the liquid-crystal mixtures according to the invention preferably has a width of at least 90°, in particular at least 100°. This range preferably extends at least from −25° C. to +70° C.

It goes without saying that, through a suitable choice of the components of the mixtures according to the invention, it is also possible for higher clearing points (for example above 100° C.) to be achieved at higher threshold voltages or lower clearing points to be achieved at lower threshold voltages with retention of the other advantageous properties. At viscosities correspondingly increased only slightly, it is likewise possible to obtain mixtures having a higher Δ∈ and thus low thresholds. The MLC displays according to the invention preferably operate at the first Gooch and Tarry transmission minimum [C. H. Gooch and H. A. Tarry, Electron. Lett. 10, 2-4, 1974; C. H. Gooch and H. A. Tarry, Appl. Phys., Vol. 8, 1575-1584, 1975], where, besides particularly favourable electro-optical properties, such as, for example, high steepness of the characteristic line and low angle dependence of the contrast (German patent 30 22 818), lower dielectric anisotropy is sufficient at the same threshold voltage as in an analogous display at the second minimum. This enables significantly higher specific resistance values to be achieved using the mixtures according to the invention at the first minimum than in the case of mixtures comprising cyano compounds. Through a suitable choice of the individual components and their proportions by weight, the person skilled in the art is able to set the birefringence necessary for a pre-specified layer thickness of the MLC display using simple routine methods.

Measurements of the voltage holding ratio (HR) [S. Matsumoto et al., Liquid Crystals 5, 1320 (1989); K. Niwa et al., Proc. SID Conference, San Francisco, June 1984, p. 304 (1984); G. Weber et al., Liquid Crystals 5, 1381 (1989)] have shown that mixtures according to the invention comprising compounds of the formula I exhibit a significantly smaller decrease in the HR on UV exposure than analogous mixtures comprising cyano-phenylcyclohexanes of the formula

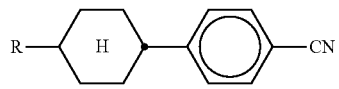

or esters of the formula

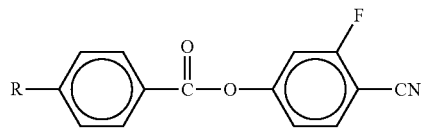

instead of the compounds of the formula I.

The light stability and UV stability of the mixtures according to the invention are considerably better, i.e. they exhibit a significantly smaller decrease in the HR on exposure to light or UV. Even low concentrations of the compounds (<10% by weight) of the formula I in the mixtures increase the HR by 6% or more compared with mixtures from the prior art.

The LC media may also comprise further additives known to the person skilled in the art and described in the literature, such as, for example, UV stabilisers, such as Tinuvin® from Ciba, antioxidants, free-radical scavengers, nanoparticles, etc. For example, 0-15% of pleochroic dyes or chiral dopants can be added. Suitable stabilisers and dopants are mentioned below in Tables C and D.

The individual components of the above-mentioned preferred embodiments of the LC media according to the invention are either known or their preparation methods can readily be derived from the prior art by the person skilled in the relevant art since they are based on standard methods described in the literature.

It goes without saying to the person skilled in the art that the LC media according to the invention may also comprise compounds in which, for example, H, N, O, Cl, F have been replaced by the corresponding isotopes.

The liquid-crystal mixtures which can be used in accordance with the invention are prepared in a manner conventional per se, for example by mixing one or more compounds of the formula I with one or more compounds of the formulae II-XXVIII or with further liquid-crystalline compounds and/or additives. In general, the desired amount of the components used in lesser amount is dissolved in the components making up the principal constituent, advantageously at elevated temperature. It is also possible to mix solutions of the components in an organic solvent, for example in acetone, chloroform or methanol, and to remove the solvent again, for example by distillation, after thorough mixing. The invention furthermore relates to the process for the preparation of the LC media according to the invention.

The construction of the MLC display according to the invention from polarisers, electrode base plates and surface-treated electrodes corresponds to the usual design for displays of this type. The term usual design is broadly drawn here and also encompasses all derivatives and modifications of the MLC display, in particular including matrix display elements based on poly-Si TFTs or MIM.

A significant difference between the displays according to the invention and the hitherto conventional displays based on the twisted nematic cell consists, however, in the choice of the liquid-crystal parameters of the liquid-crystal layer.

The following examples explain the present invention without limiting it. However, they show the person skilled in the art preferred mixture concepts with compounds preferably to be employed and the respective concentrations thereof and combinations thereof with one another. In addition, the examples illustrate which properties and property combinations are accessible.

In the present application and in the examples below, the structures of the liquid-crystal compounds are indicated by means of acronyms, with the transformation into chemical formulae taking place in accordance with Tables A and B below. All radicals $C_nH_{2n+1}$ and $C_mH_{2m+1}$ are straight-chain alkyl radicals having n and m C atoms respectively; n, m and k are integers and preferably denote 0, 1, 2, 3, 4, 5, 6, 7, 8, 9, 10, 11 or 12. The coding in Table B is self-evident. In Table A, only the acronym for the parent structure is indicated. In individual cases, the acronym for the parent structure is followed, separated by a dash, by a code for the substituents $R^{1*}$, $R^{2*}$, $L^{1*}$ and $L^{2*}$:

| Code for $R^{1*}$, $R^{2*}$, $L^{1*}$, $L^{2*}$, $L^{3*}$ | $R^{1*}$ | $R^{2*}$ | $L^{1*}$ | $L^{2*}$ |
|---|---|---|---|---|
| nm | $C_nH_{2n+1}$ | $C_mH_{2m+1}$ | H | H |
| nOm | $C_nH_{2n+1}$ | $OC_mH_{2m+1}$ | H | H |
| nO•m | $OC_nH_{2n+1}$ | $C_mH_{2m+1}$ | H | H |
| n | $C_nH_{2n+1}$ | CN | H | H |
| nN•F | $C_nH_{2n+1}$ | CN | F | H |
| nN•F•F | $C_nH_{2n+1}$ | CN | F | F |
| nF | $C_nH_{2n+1}$ | F | H | H |
| nCl | $C_nH_{2n+1}$ | Cl | H | H |
| nOF | $OC_nH_{2n+1}$ | F | H | H |
| nF•F | $C_nH_{2n+1}$ | F | F | H |
| nF•F•F | $C_nH_{2n+1}$ | F | F | F |
| nOCF$_3$ | $C_nH_{2n+1}$ | OCF$_3$ | H | H |
| nOCF$_3$•F | $C_nH_{2n+1}$ | OCF$_3$ | F | H |
| n-Vm | $C_nH_{2n+1}$ | —CH=CH—$C_mH_{2m+1}$ | H | H |
| nV—Vm | $C_nH_{2n+1}$—CH=CH— | —CH=CH—$C_mH_{2m+1}$ | H | H |

Preferred mixture components are found in Tables A and B.
TABLE A
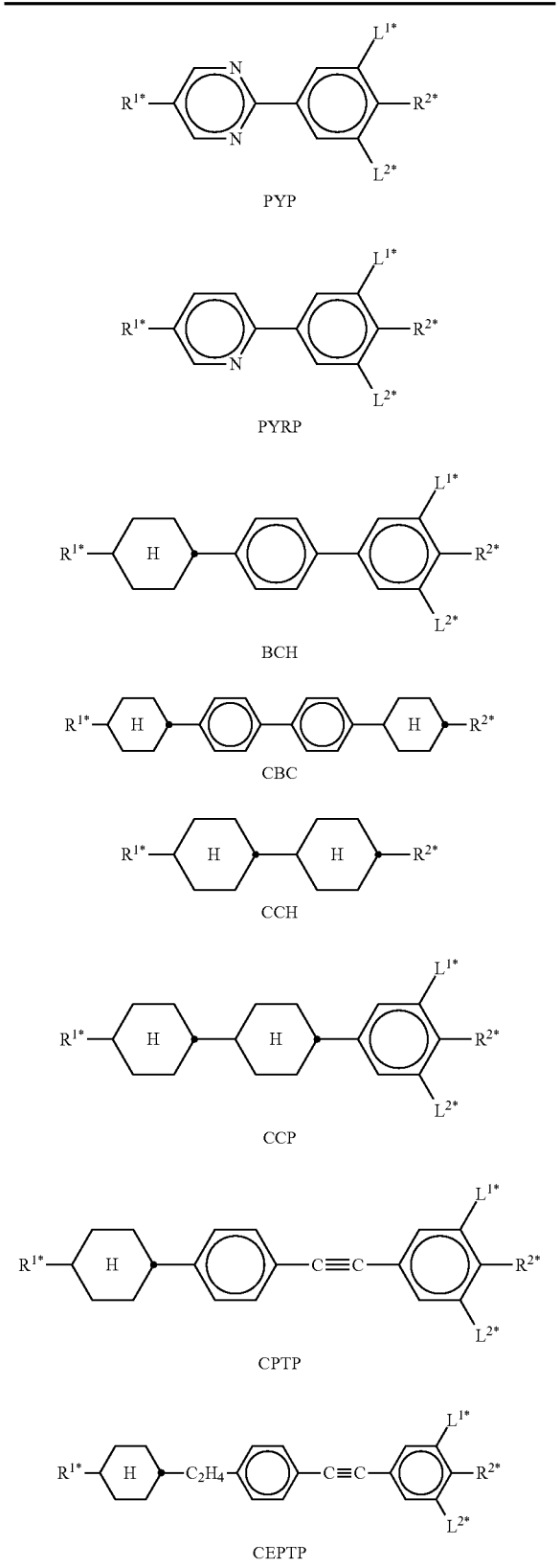
TABLE A-continued
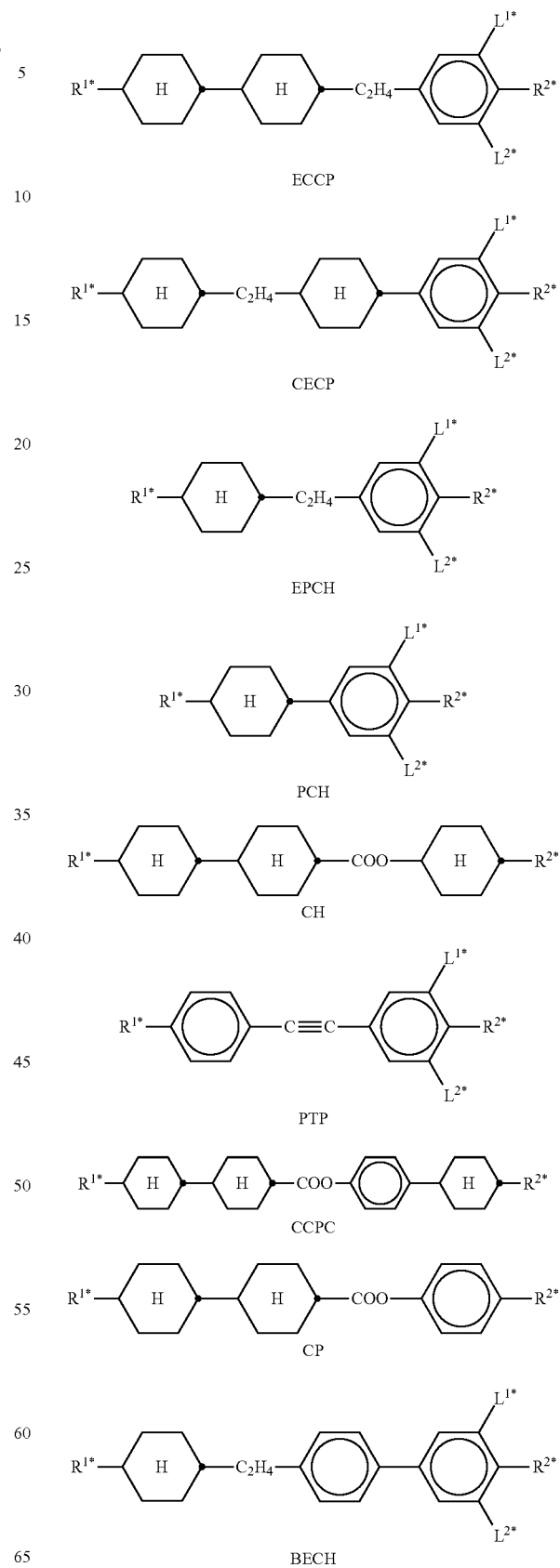

TABLE A-continued
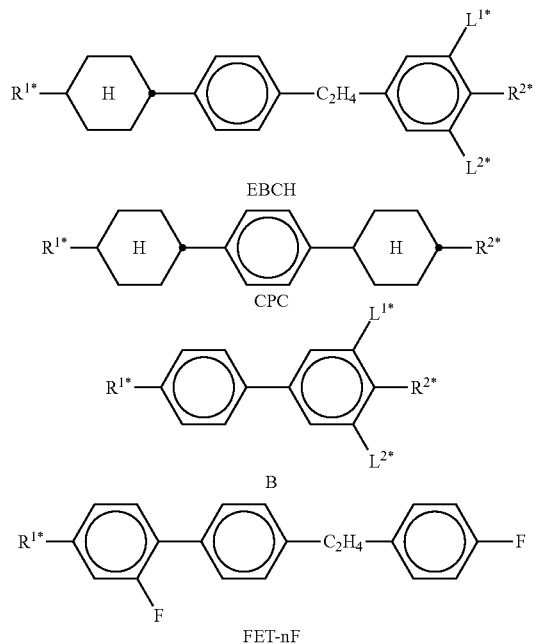
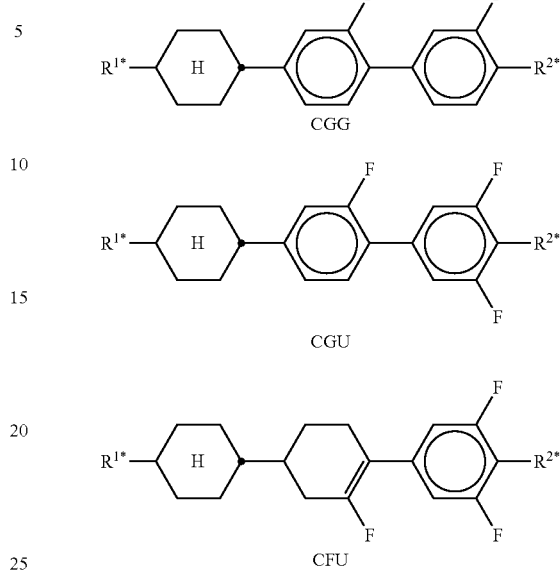
TABLE B
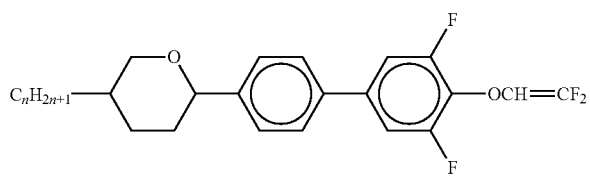
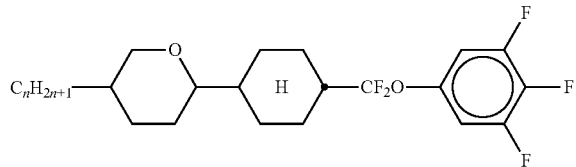
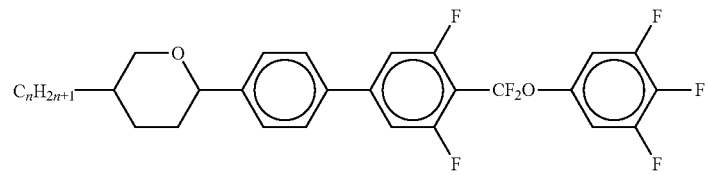
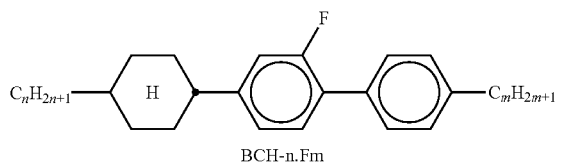

TABLE B-continued
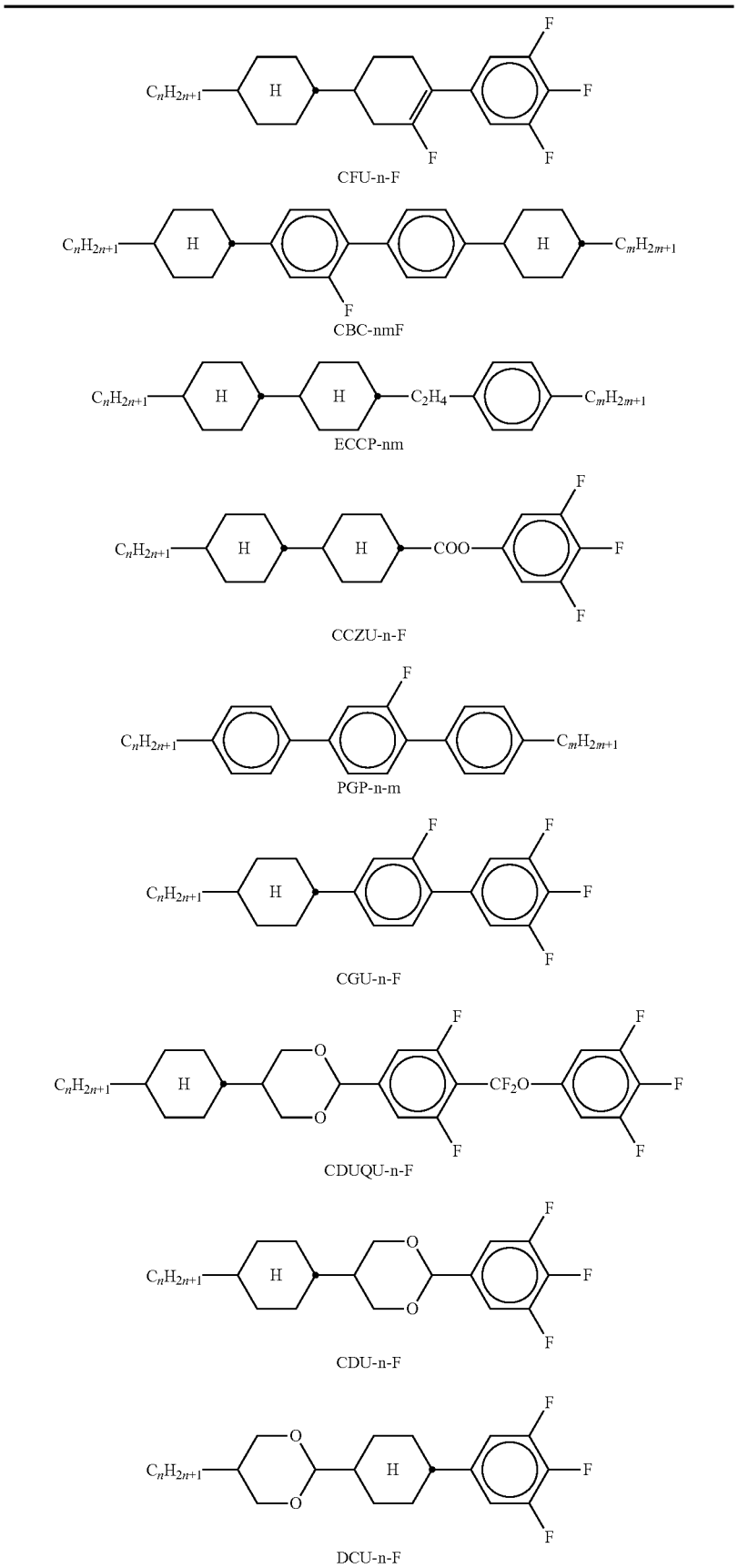

TABLE B-continued
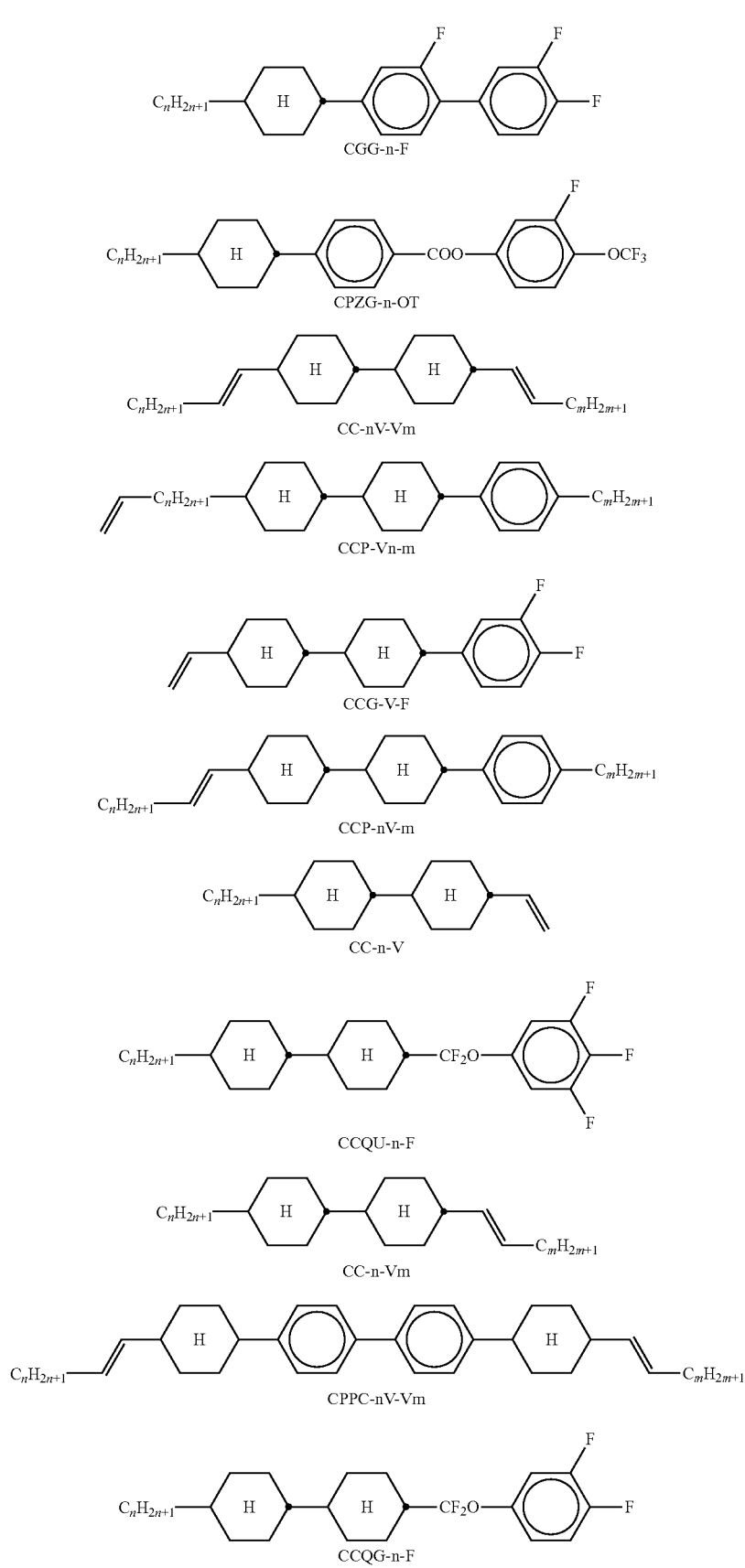

TABLE B-continued
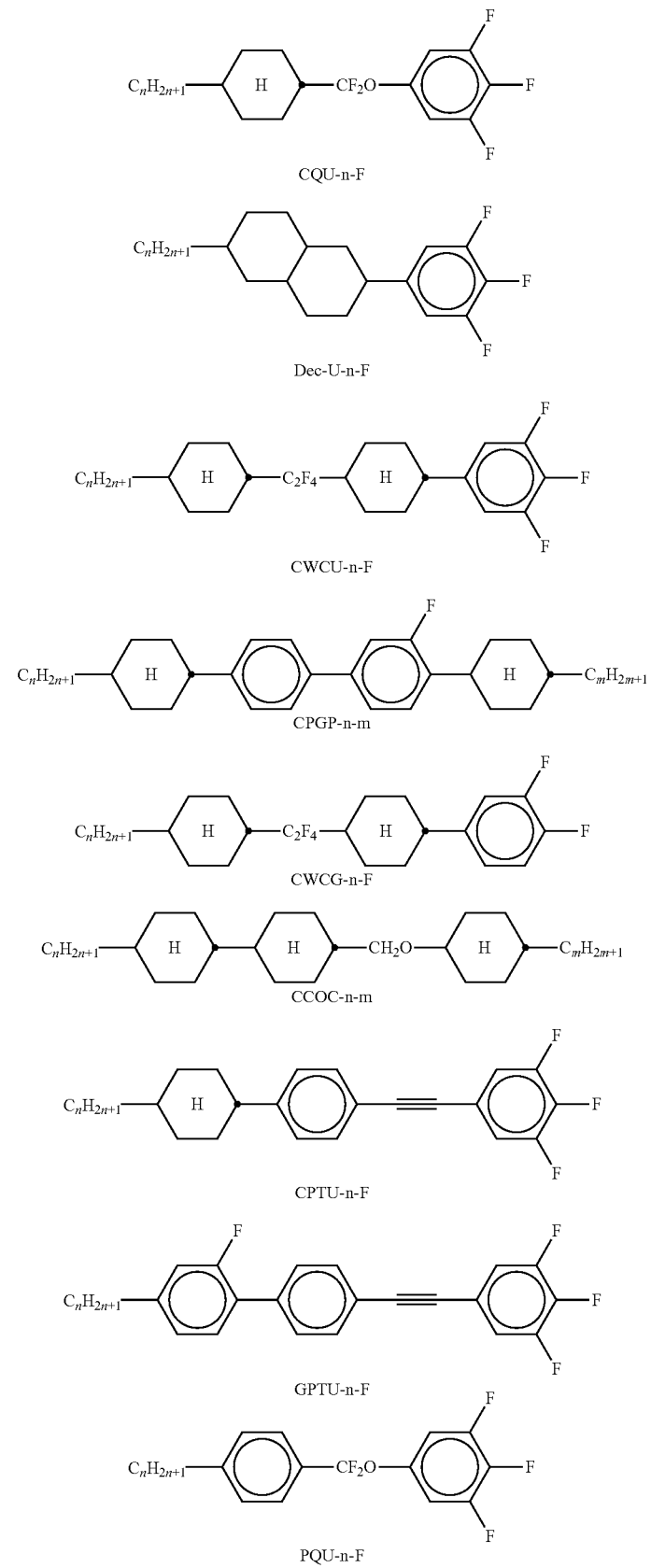

TABLE B-continued
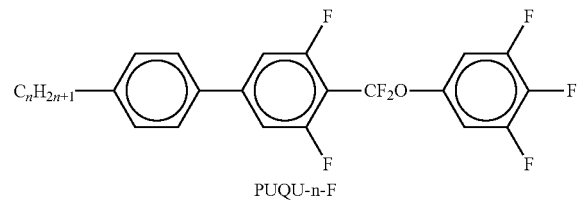
PUQU-n-F
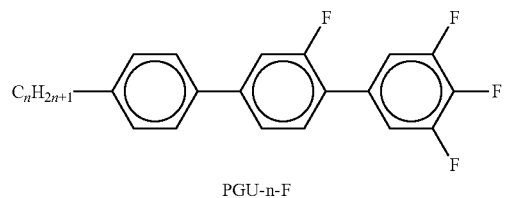
PGU-n-F
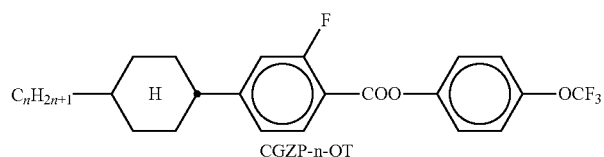
CGZP-n-OT
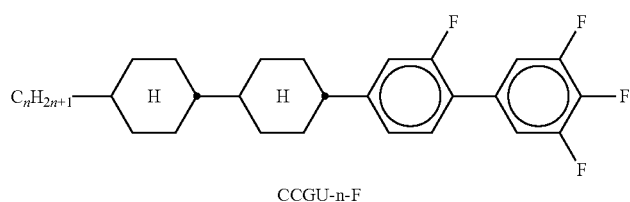
CCGU-n-F
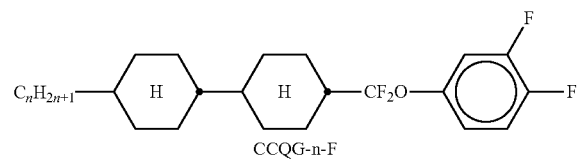
CCQG-n-F
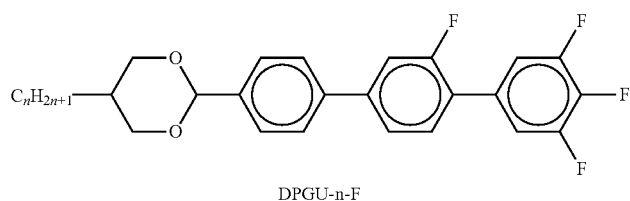
DPGU-n-F
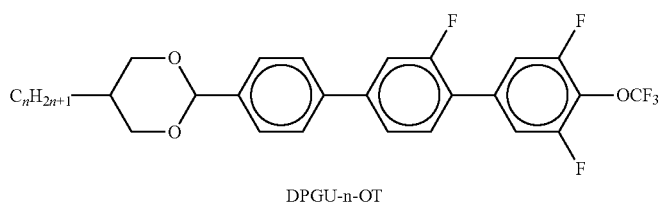
DPGU-n-OT
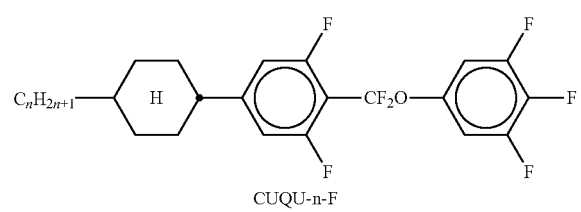
CUQU-n-F TABLE B-continued
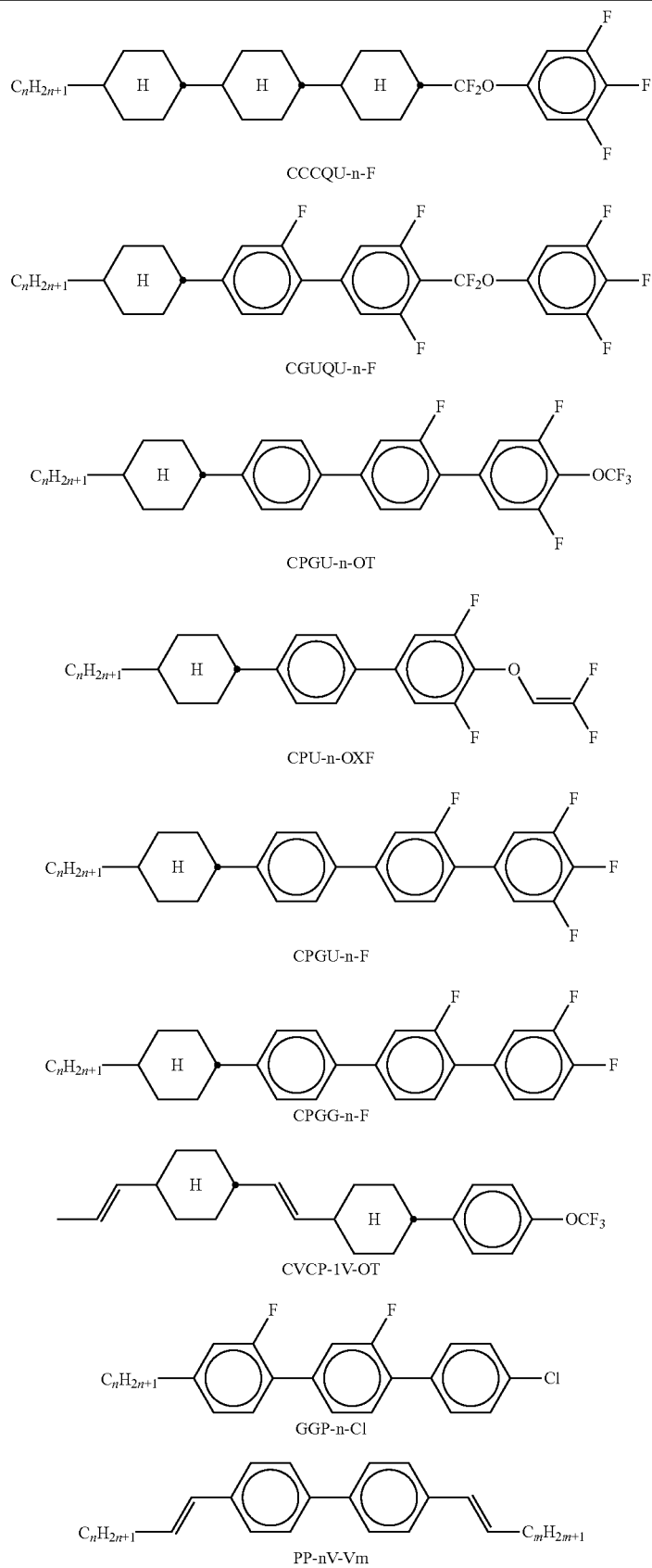

TABLE B-continued
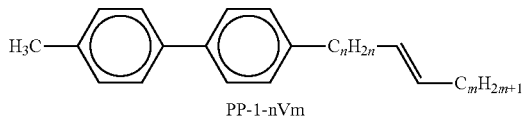
PP-1-nVm
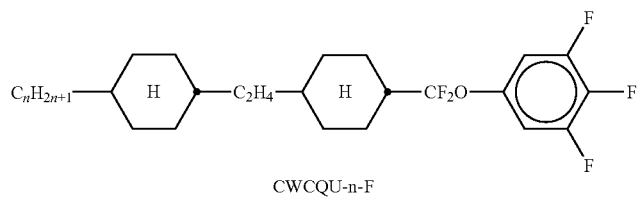
CWCQU-n-F
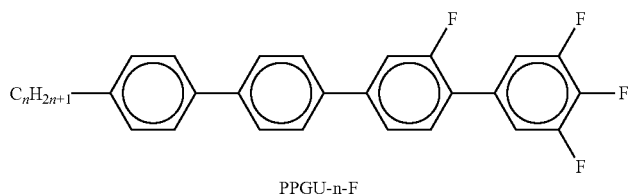
PPGU-n-F
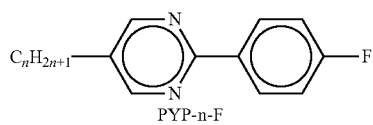
PYP-n-F
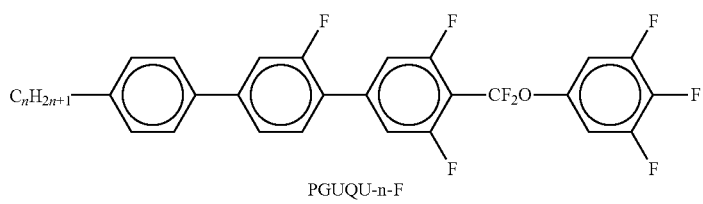
PGUQU-n-F
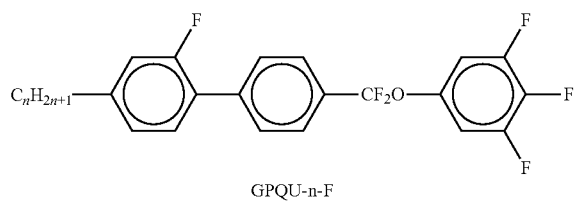
GPQU-n-F
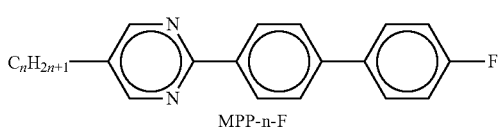
MPP-n-F
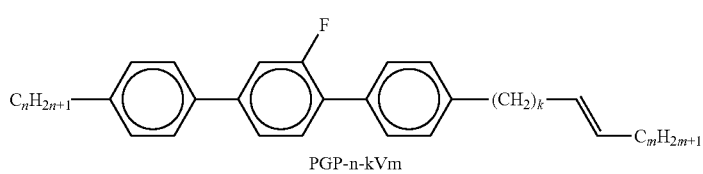
PGP-n-kVm
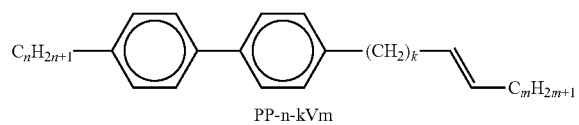
PP-n-kVm
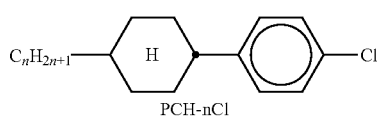
PCH-nCl TABLE B-continued
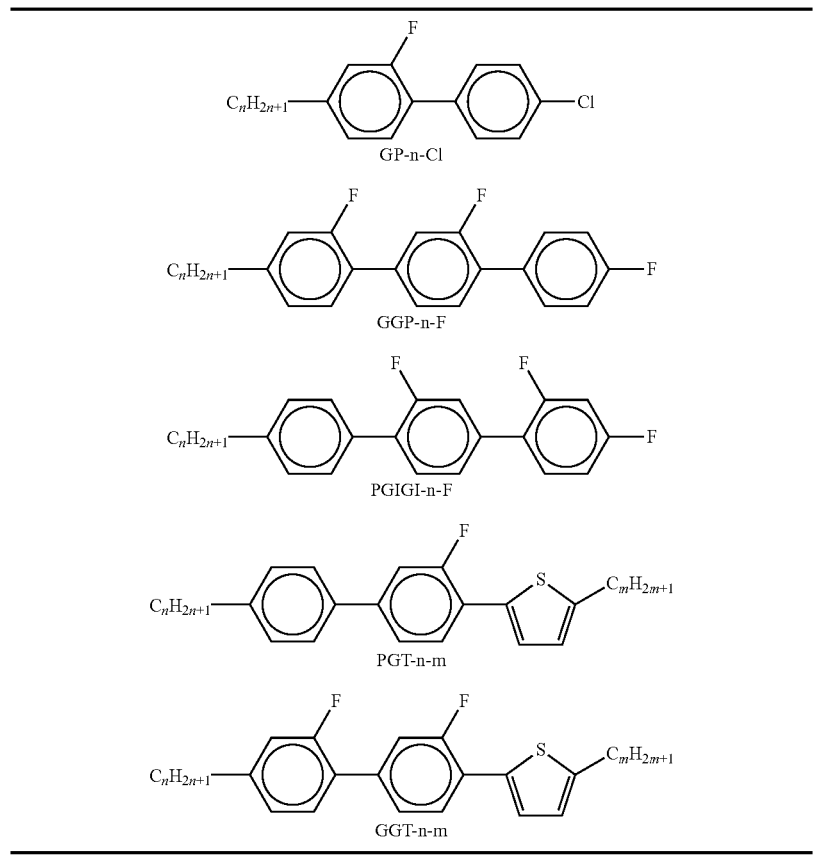
In a preferred embodiment of the present invention, the LC media according to the invention comprise one or more compounds selected from the group consisting of compounds from Tables A and B.
TABLE C
Table C indicates possible dopants which can be added to the LC media according to the invention.
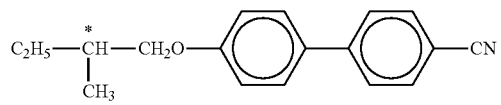
C 15
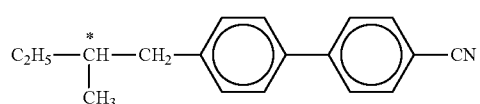
CB 15
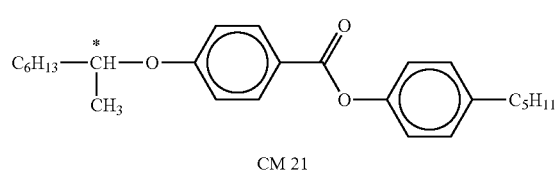
CM 21

TABLE C-continued
Table C indicates possible dopants which can be added to the LC media according to the invention.
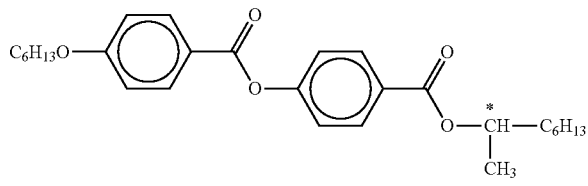
R/S-811
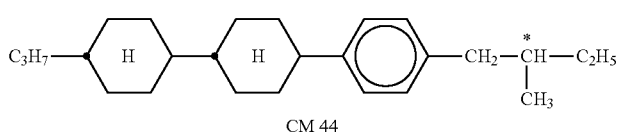
CM 44
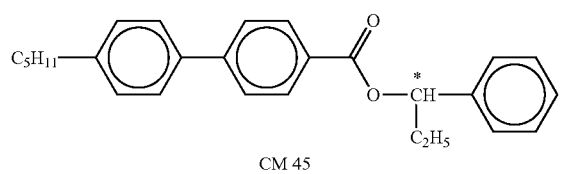
CM 45
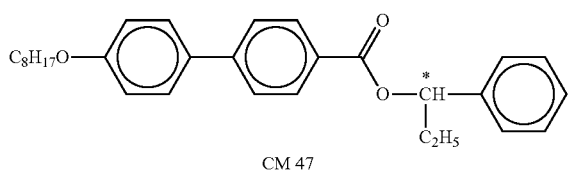
CM 47
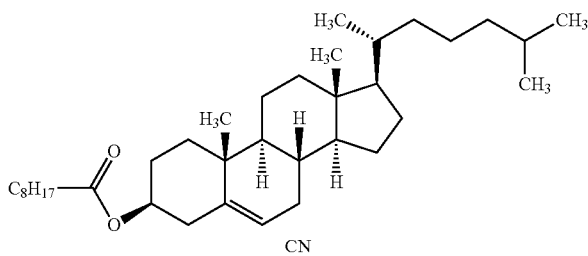
CN
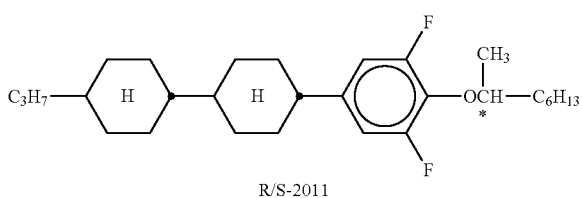
R/S-2011
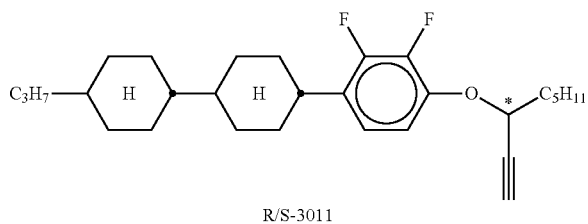
R/S-3011
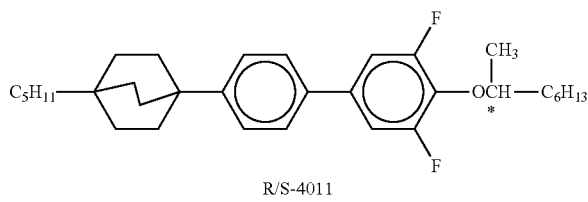
R/S-4011

TABLE C-continued

Table C indicates possible dopants which can be added to the LC media according to the invention.

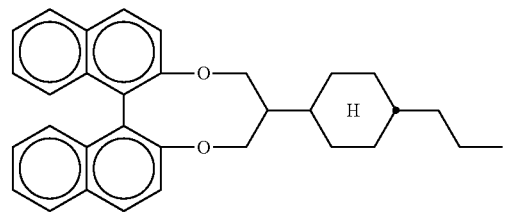

R/S-5011

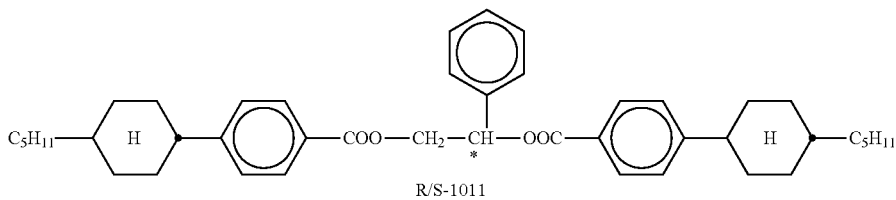

R/S-1011

The LC media preferably comprise 0 to 10% by weight, in particular 0.01 to 5% by weight and particularly preferably 0.1 to 3% by weight, of dopants. The LC media preferably comprise one or more dopants selected from the group consisting of compounds from Table C.

TABLE D

Table D indicates possible stabilisers which can be added to the LC media according to the invention.
(n here denotes an integer from 1 to 12)

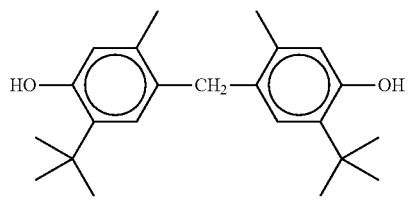

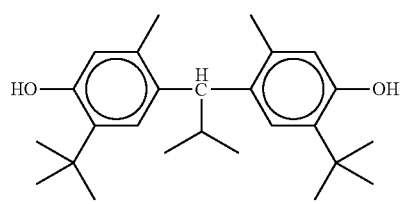

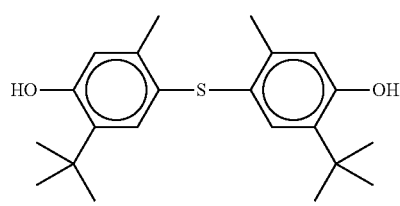

TABLE D-continued
Table D indicates possible stabilisers which can be added to the LC media according to the invention.
(n here denotes an integer from 1 to 12)
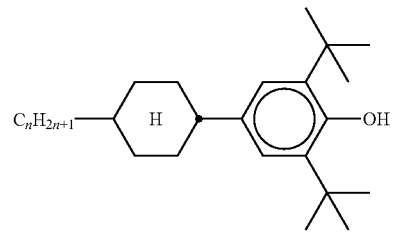
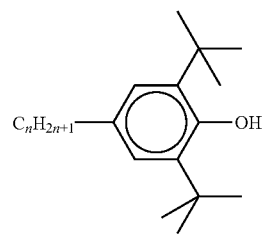
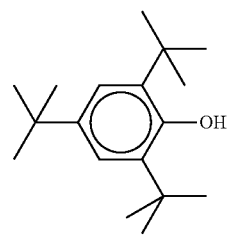
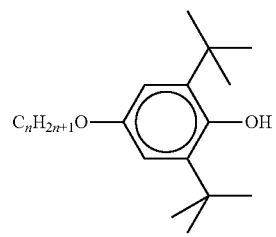
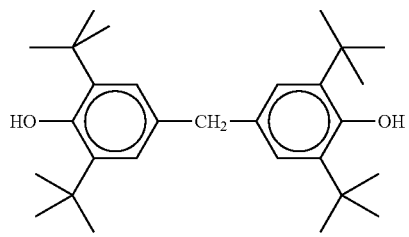
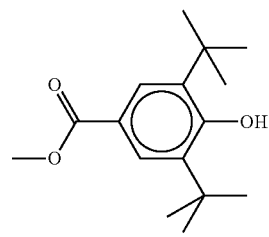

TABLE D-continued
Table D indicates possible stabilisers which can be added to the LC media according to the invention.
(n here denotes an integer from 1 to 12)
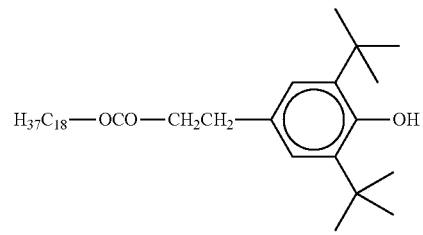
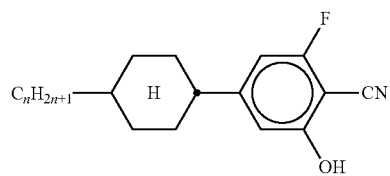
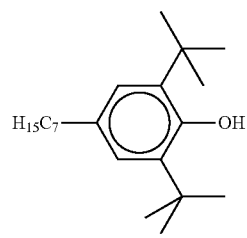
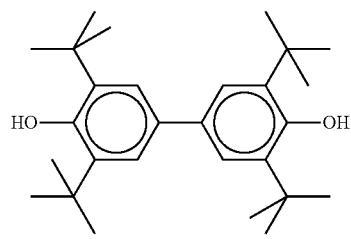
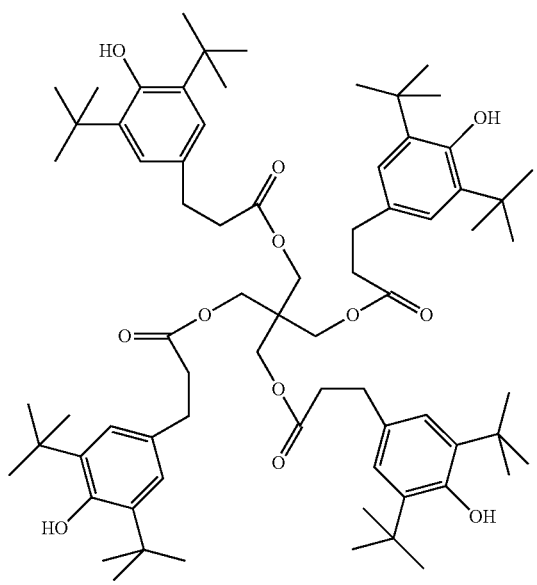 [SMILES: CC(C)(C)c1cc(CCC(=O)OCC(COC(=O)CCc2cc(C(C)(C)C)c(O)c(C(C)(C)C)c2)(COC(=O)CCc2cc(C(C)(C)C)c(O)c(C(C)(C)C)c2)COC(=O)CCc2cc(C(C)(C)C)c(O)c(C(C)(C)C)c2)cc(C(C)(C)C)c1O]

TABLE D-continued
Table D indicates possible stabilisers which can be added to the LC media according to the invention.
(n here denotes an integer from 1 to 12)
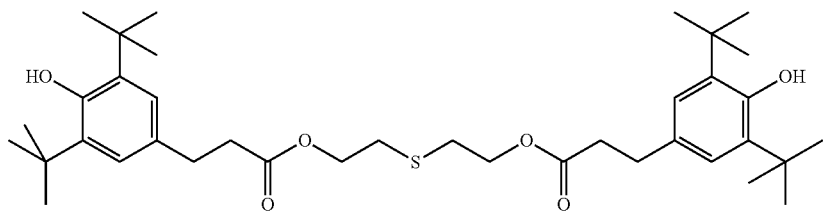 [SMILES: CC(C)(C)c1cc(CCC(=O)OCCSCCOC(=O)CCc2cc(C(C)(C)C)c(O)c(C(C)(C)C)c2)cc(C(C)(C)C)c1O]
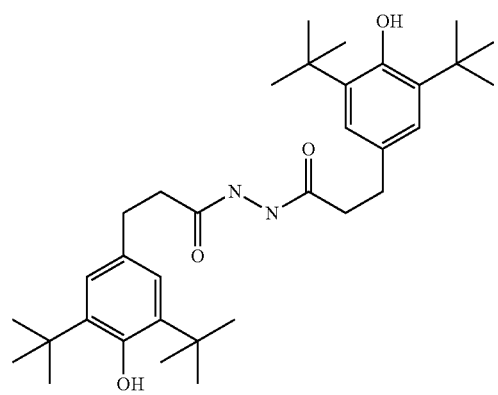 [SMILES: CC(C)(C)c1cc(CCC(=O)NNC(=O)CCc2cc(C(C)(C)C)c(O)c(C(C)(C)C)c2)cc(C(C)(C)C)c1O]
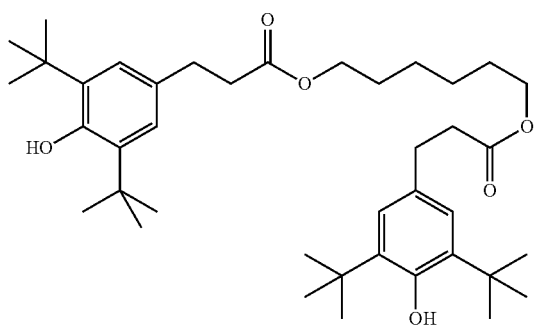 [SMILES: CC(C)(C)c1cc(CCC(=O)OCCCCCCOC(=O)CCc2cc(C(C)(C)C)c(O)c(C(C)(C)C)c2)cc(C(C)(C)C)c1O]
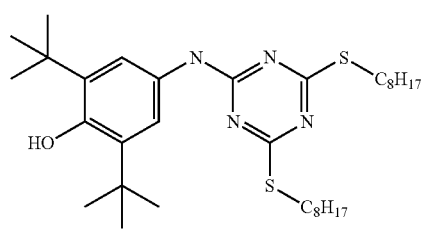

TABLE D-continued
Table D indicates possible stabilisers which can be added to the LC media according to the invention.
(n here denotes an integer from 1 to 12)
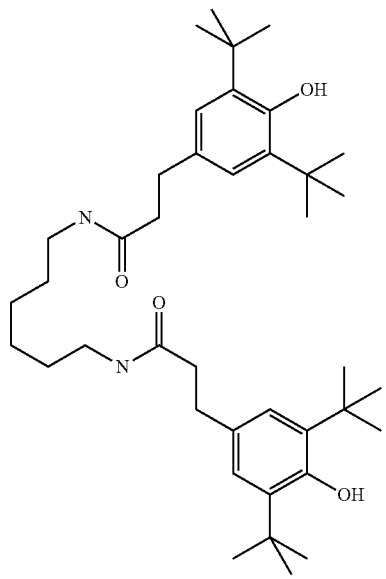 [SMILES: CC(C)(C)c1cc(CCC(=O)NCCCCCCNC(=O)CCc2cc(C(C)(C)C)c(O)c(C(C)(C)C)c2)cc(C(C)(C)C)c1O]
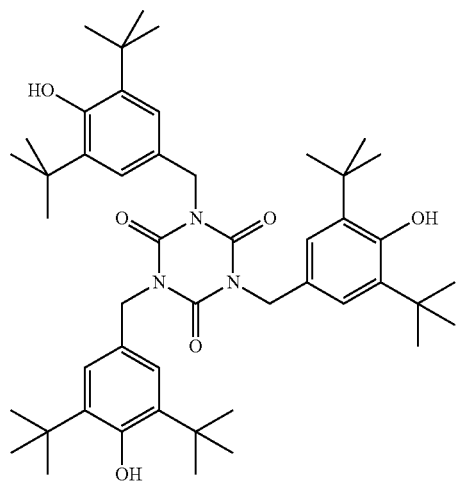 [SMILES: CC(C)(C)c1cc(Cn2c(=O)n(Cc3cc(C(C)(C)C)c(O)c(C(C)(C)C)c3)c(=O)n(Cc3cc(C(C)(C)C)c(O)c(C(C)(C)C)c3)c2=O)cc(C(C)(C)C)c1O]
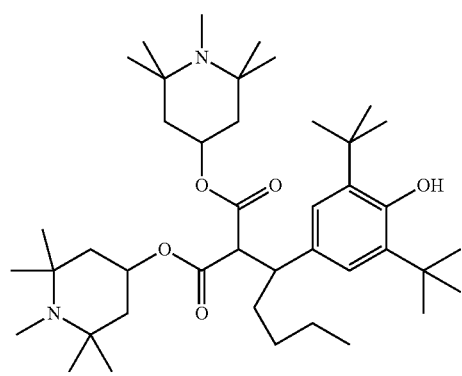 [SMILES: CCCCC(c1cc(C(C)(C)C)c(O)c(C(C)(C)C)c1)C(C(=O)OC1CC(C)(C)N(C)C(C)(C)C1)C(=O)OC1CC(C)(C)N(C)C(C)(C)C1]

TABLE D-continued
Table D indicates possible stabilisers which can be added to the LC media according to the invention.
(n here denotes an integer from 1 to 12)
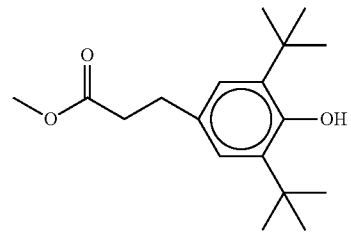
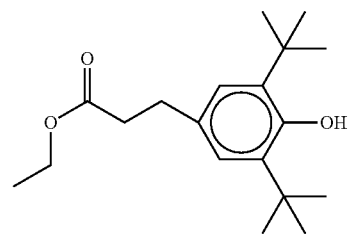
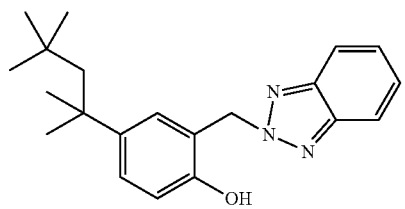 [SMILES: CC(C)(C)CC(C)(C)c1ccc(O)c(Cn2nc3ccccc3n2)c1]
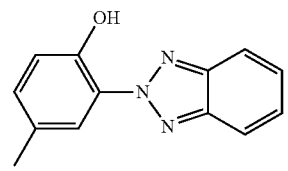 [SMILES: Cc1ccc(O)c(-n2nc3ccccc3n2)c1]
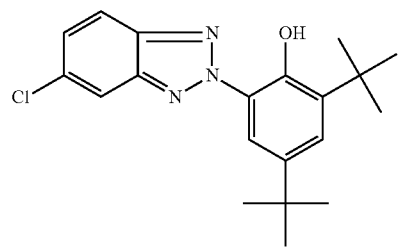 [SMILES: CC(C)(C)c1cc(-n2nc3ccc(Cl)cc3n2)c(O)c(C(C)(C)C)c1]
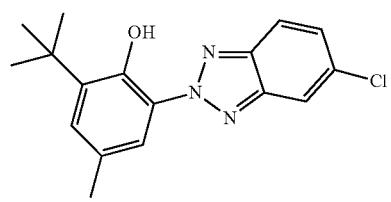 [SMILES: Cc1cc(-n2nc3ccc(Cl)cc3n2)c(O)c(C(C)(C)C)c1]

TABLE D-continued
Table D indicates possible stabilisers which can be added to the LC media according to the invention.
(n here denotes an integer from 1 to 12)
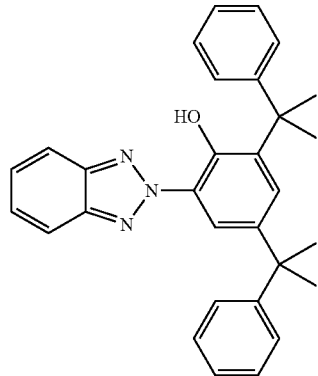 [SMILES: CC(C)(c1ccccc1)c1cc(-n2nc3ccccc3n2)c(O)c(C(C)(C)c2ccccc2)c1]
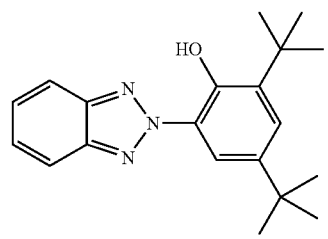 [SMILES: CC(C)(C)c1cc(-n2nc3ccccc3n2)c(O)c(C(C)(C)C)c1]
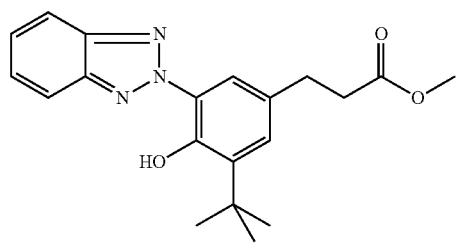 [SMILES: COC(=O)CCc1cc(-n2nc3ccccc3n2)c(O)c(C(C)(C)C)c1]
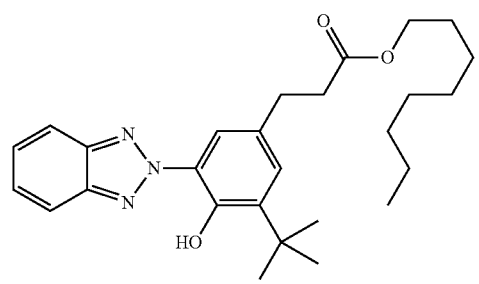 [SMILES: CCCCCCCCOC(=O)CCc1cc(-n2nc3ccccc3n2)c(O)c(C(C)(C)C)c1]

TABLE D-continued
Table D indicates possible stabilisers which can be added to the LC media according to the invention.
(n here denotes an integer from 1 to 12)
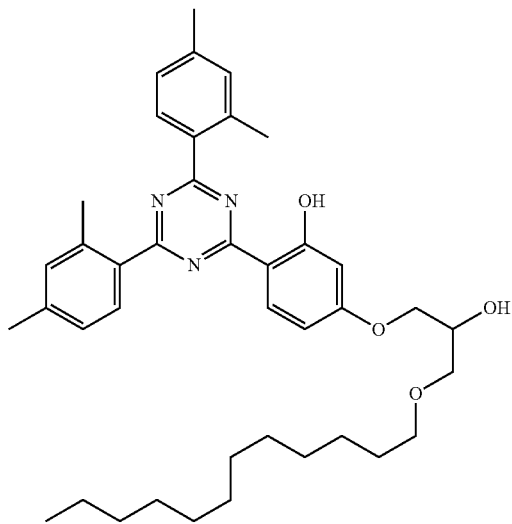 [SMILES: CCCCCCCCCCCCOCC(O)COc1ccc(-c2nc(-c3ccc(C)cc3C)nc(-c3ccc(C)cc3C)n2)c(O)c1]
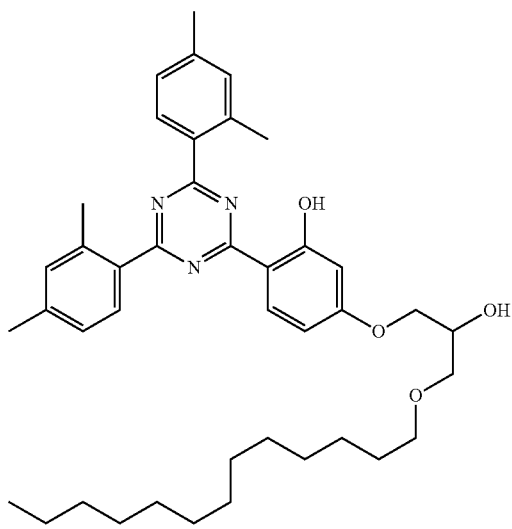 [SMILES: CCCCCCCCCCCCCOCC(O)COc1ccc(-c2nc(-c3ccc(C)cc3C)nc(-c3ccc(C)cc3C)n2)c(O)c1]
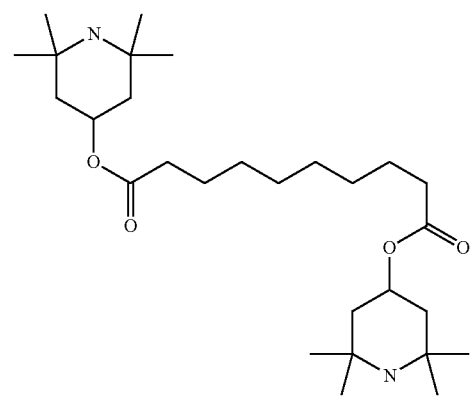

TABLE D-continued

Table D indicates possible stabilisers which can be added to the LC media according to the invention.
(n here denotes an integer from 1 to 12)

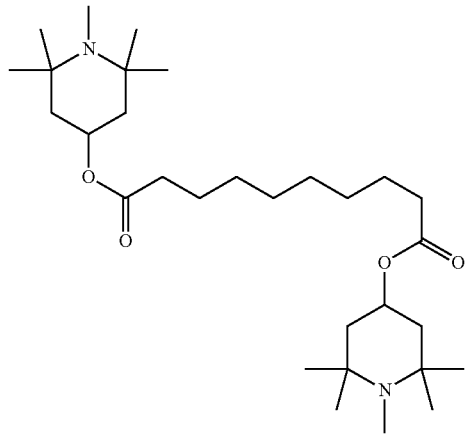

The LC media preferably comprise 0 to 10% by weight, in particular 0.01 to 5% by weight and particularly preferably 0.1 to 3% by weight, of stabilisers. The LC media preferably comprise one or more stabilisers selected from the group consisting of compounds from Table D.

In addition, the following abbreviations and symbols are used:

| | |
|---|---|
| $V_0$ | threshold voltage, capacitive [V] at 20° C., |
| $V_{10}$ | optical threshold for 10% relative contrast [V] at 20° C., |
| $n_e$ | extraordinary refractive index at 20° C. and 589 nm, |
| $n_o$ | ordinary refractive index at 20° C. and 589 nm, |
| $\Delta n$ | optical anisotropy at 20° C. and 589 nm, |
| $\epsilon_\perp$ | dielectric susceptibility perpendicular to the director at 20° C. and 1 kHz, |
| $\epsilon_\parallel$ | dielectric susceptibility parallel to the director at 20° C. and 1 kHz, |
| $\Delta\epsilon$ | dielectric anisotropy at 20° C. and 1 kHz, |
| cl.p., T(N,I) | clearing point [° C.], |
| $\gamma_1$ | rotational viscosity at 20° C. [mPa · s], |
| $K_1$ | elastic constant, "splay" deformation at 20° C. [pN], |
| $K_2$ | elastic constant, "twist" deformation at 20° C. [pN], |
| $K_3$ | elastic constant, "bend" deformation at 20° C. [pN], |
| LTS | low-temperature stability (phase), determined in test cells, |
| $HR_{20}$ | voltage holding ratio at 20° C. [%] and |
| $HR_{100}$ | voltage holding ratio at 100° C. [%]. |

Unless explicitly noted otherwise, all concentrations in the present application are indicated in per cent by weight and relate to the corresponding mixture as a whole without solvents.

Unless explicitly noted otherwise, all temperature values indicated in the present application, such as, for example, the melting point T(C,N), the transition from the smectic (S) to the nematic (N) phase T(S,N) and the clearing point T(N,I), are indicated in degrees Celsius (° C.). M.p. denotes melting point, cl.p.=clearing point. Furthermore, C=crystalline state, N=nematic phase, S=smectic phase and I=isotropic phase. The data between these symbols represent the transition temperatures.

All physical properties are and have been determined in accordance with "Merck Liquid Crystals, Physical Properties of Liquid Crystals", Status November 1997, Merck KGaA, Darmstadt, Germany, and apply to a temperature of 20° C., and $\Delta n$ is determined at 589 nm and $\Delta\epsilon$ at 1 kHz, unless explicitly indicated otherwise in each case.

The liquid-crystalline properties of the individual compounds are, unless indicated otherwise, determined in the nematic host mixture ZLI-4792 (commercially available from Merck KGaA, Darmstadt) at a concentration of 10%.

"Room temperature" means 20° C., unless indicated otherwise.

The term "threshold voltage" for the present invention relates to the capacitive threshold ($V_0$), also called the Freedericks threshold, unless explicitly indicated otherwise. In the examples, as generally usual, the optical threshold for 10% relative contrast ($V_{10}$) may also be indicated.

The test cells used for measurement of the capacitive threshold voltage $V_0$ and for $V_{10}$ are constructed from substrates consisting of soda-lime glass coated with polyimide alignment layers (Durimid 32 with diluent (70% of NMP+ 30% of xylene) in the ratio 1:4) from Arch Chemicals, which are rubbed antiparallel to one another and have a surface tilt of quasi 0 degrees. The area of the transparent, virtually square ITO electrodes is 1 cm². The capacitive threshold voltage is determined using a standard commercial high-resolution LCR meter (for example Hewlett Packard 4284A LCR meter).

EXAMPLE 1

2-(4'-Ethyl-3-fluorobiphenyl-4-yl)-5-methylthiophene ("PGT-2-1")

The compound 2-(4'-ethyl-3-fluorobiphenyl-4-yl)-5-methylthiophene ("PGT-2-1") according to the invention is prepared as described below:

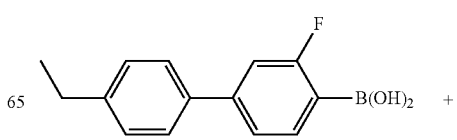

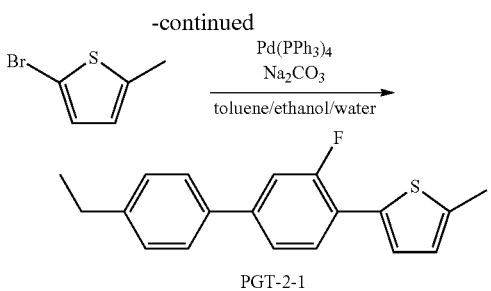

A mixture of 5.0 g (28.2 mmol) of 2-bromo-5-methylthiophene, 7.70 g (28.3 mmol) of 4'-ethyl-3-fluoro-4-biphenylboronic acid, 1.70 g (1.47 mmol) of tetrakis(triphenylphosphine)palladium(0) and 30 ml of 2 N sodium carbonate solution in 90 ml of toluene/ethanol (1:2) is refluxed for 3 h. After cooling, the organic phase is separated off, and the aqueous phase is extracted a number of times with toluene. The combined organic phases are washed with water and sat. sodium chloride solution. The solution is dried using sodium sulfate and evaporated to dryness. The residue is purified by column chromatography (SiO$_2$, n-heptane:toluene=97:3). The further purification is carried out by recrystallisation from ethanol and n-heptane, giving 2-(4'-ethyl-3-fluorobiphenyl-4-yl)-5-methylthiophene as a colourless solid (m.p. 102° C.).

$^1$H-NMR (300 MHz, CHCl$_3$): δ=7.61-7.56 (m, 1H, H$_{arom.}$), 7.50 (d, 2H, J=8.0 Hz, H$_{arom.}$), 7.37-7.24 (m, 5H, H$_{arom.}$), 6.77-6.75 (m, 1H, H$_{arom.}$), 2.69 (q, 2H, J=7.7 Hz, H$_3$CCH$_2$—), 2.52 (s, 3H, CH$_3$), 1.27 (t, 3H, J=7.7 Hz, H$_3$CCH$_2$—).
$^{19}$F-NMR (282 MHz, CHCl$_3$): δ=−114.1 (dd, 1F, J=12.4 Hz, J=8.2 Hz). MS (EI): m/e (%)=296 (100, M$^+$), 281 (49, [M-CH$_3$]$^+$)

Δε=+4.3
Δn=0.3279
γ$_1$=115 mPa·s
C 102 N 116 I

EXAMPLE 2

2-(4'-Propyl-3-fluorobiphenyl-4-yl)thiophene ("PGT-3-H")

The compound 2-(4'-propyl-3-fluorobiphenyl-4-yl)thiophene ("PGT-3-H") according to the invention is prepared as described below:

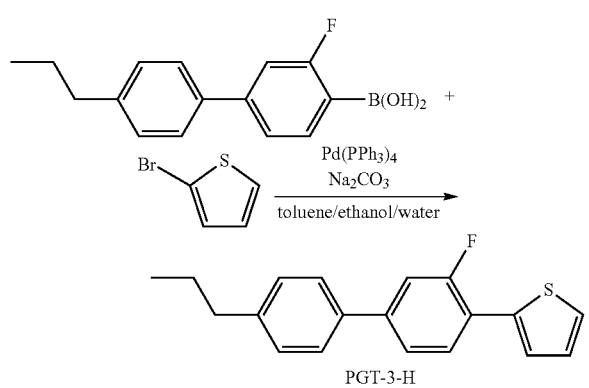

A mixture of 25.3 g (0.16 mol) of 2-bromothiophene, 40.0 g (0.16 mol) of 4'-propyl-3-fluoro-4-biphenylboronic acid, 8.5 g (7.4 mmol) of tetrakis(triphenylphosphine)palladium(0) and 170 ml of 2 N sodium carbonate solution in 420 ml of toluene/ethanol (1:2) is refluxed for 18 h. After cooling, the organic phase is separated off, and the aqueous phase is extracted a number of times with toluene. The combined organic phases are washed with water and sat. sodium chloride solution. The solution is dried using sodium sulfate and evaporated to dryness. The residue is purified by column chromatography (SiO$_2$, n-heptane:toluene=9:1). The further purification is carried out by recrystallisation from ethanol and n-heptane, giving 2-(4'-propyl-3-fluorobiphenyl-4-yl)thiophene as a colourless solid (m.p. 88° C.).

$^1$H-NMR (400 MHz, CHCl$_3$): δ=7.69-7.65 (m, 1H, H$_{arom.}$), 7.53-7.49 (m, 3H, H$_{arom.}$), 7.41-7.35 (m, 3H, H$_{arom.}$), 7.28-7.24 (m, 2H, H$_{arom.}$), 7.14-7.11 (m, 1H, H$_{arom.}$), 2.63 (t, 2H, J=7.6 Hz, H$_3$CCH$_2$CH$_2$—), 1.73-1.63 (m, 2H, H$_3$CCH$_2$CH$_2$—), 0.97 (t, 3H, J=7.6 Hz, H$_3$CCH$_2$CH$_2$—).
$^{19}$F-NMR (377 MHz, CHCl$_3$): δ=−113.8 (dd, 1F, J=12.8 Hz, J=7.9 Hz).
MS (EI): m/e (%)=296 (97, M$^+$), 267 (100, [M-Et]$^+$)
Δε=+3.9
Δn=0.2949
γ$_1$=145 mPa·s
C 88 I

EXAMPLE 3

2-(4'-Ethyl-3-fluorobiphenyl-4-yl)-5-propylthiophene ("PGT-2-3")

The compound 2-(4'-ethyl-3-fluorobiphenyl-4-yl)-5-propylthiophene ("PGT-2-3") according to the invention is prepared as described below:

Synthesis of 5-(4'-ethyl-3-fluorobiphenyl-4-yl)thiophene-2-carbaldehyde

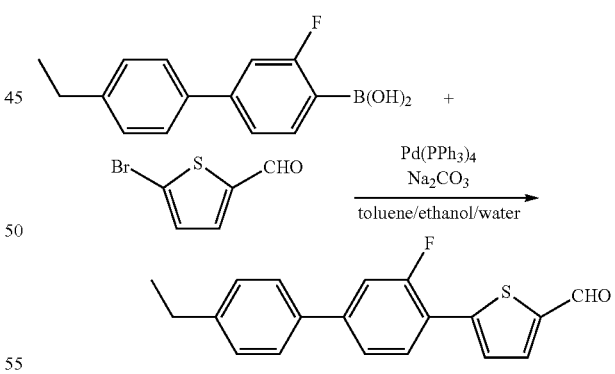

A mixture of 58.5 g (0.31 mol) of 5-bromothiophene-2-carbaldehyde, 75.5 g (0.31 mol) of 4'-ethyl-3-fluoro-4-biphenylboronic acid, 17.0 g (14.7 mmol) of tetrakis(triphenylphosphine)palladium(0) and 375 ml of 2 N sodium carbonate solution in 935 ml of toluene/ethanol (1:1.5) is heated at 80° C. for 1 h. After cooling, the precipitated product is firstly dissolved by addition of THF. The organic phase is separated off, and the aqueous phase is extracted with MTBE. The combined organic phases are washed with sat. sodium chloride solution, and the solution is dried using sodium sulfate. The residue remaining after removal of the solvents is digested in toluene, and the product is filtered off, giving 5-(4'-ethyl-3-fluorobiphenyl-4-yl)thiophene-2-carbaldehyde as a yellow solid.

Synthesis of 2-(4'-ethyl-3-fluorobiphenyl-4-yl)-5-propenylthiophene

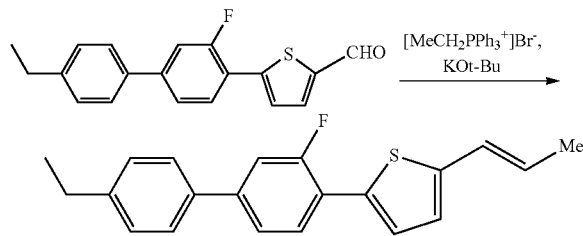

26.0 g (70.0 mmol) of ethyltriphenylphosphonium bromide are initially introduced in 400 ml of THF together with 20.0 g (62.6 mmol) of 5-(4'-ethyl-3-fluorobiphenyl-4-yl)thiophene-2-carbaldehyde, and a solution of 7.86 g (70.0 mmol) of potassium tert-butoxide in 100 ml of THF is added with ice-cooling. The mixture is stirred at room temperature for 20 h. Water and 2 N hydrochloric acid are added, and the batch is extracted with MTBE. The organic phase is washed with sat. sodium chloride solution and dried using sodium sulfate. The solution is evaporated to dryness, and the residue is purified by column chromatography (SiO$_2$, n-heptane:toluene 9:1→toluene).

Synthesis of 2-(4'-ethyl-3-fluorobiphenyl-4-yl)-5-propylthiophene

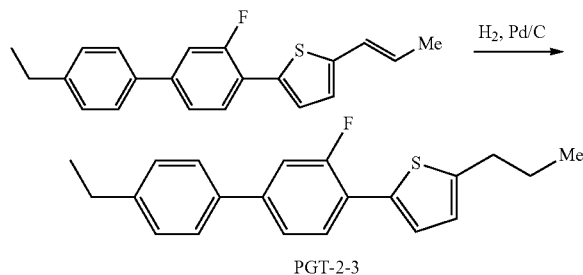

3.10 g (8.73 mmol) of 2-(4'-ethyl-3-fluorobiphenyl-4-yl)-5-propenylthiophene are hydrogenated in 100 ml of THF, in the presence of Pd/C (5% of Pd) at atmospheric pressure and room temperature. The reaction solution is evaporated to dryness, and the crude product is purified by column chromatography (SiO$_2$, n-heptane:toluene=9:1). The further purification is carried out by recrystallisation from ethanol and n-heptane, giving 2-(4'-ethyl-3-fluorobiphenyl-4-yl)-5-propylthiophene as a colourless solid (m.p. 41° C.).

$^1$H-NMR (400 MHz, CHCl$_3$): δ=7.61-7.56 (m, 1H, H$_{arom.}$), 7.49 (d, 2H, J=8.4 Hz, H$_{arom.}$), 7.34 (broad 5, 1H, H$_{arom.}$), 7.33-7.30 (m, 2H, H$_{arom.}$), 7.25 (d, 2H, J=8.4 Hz, H$_{arom.}$), 6.78-6.76 (m, 1H, H$_{arom.}$), 2.80 (t, 2H, J=7.6 Hz, —CH$_2$CH$_2$CH$_3$), 2.67 (q, 2H, J=7.6 Hz, CH$_3$CH$_2$—), 1.78-1.68 (m, 2H, —CH$_2$CH$_2$CH$_3$), 1.26 (t, 3H, J=7.6 Hz, CH$_3$CH$_2$—), 0.99 (t, 3H, J=7.4 Hz, —CH$_2$CH$_2$CH$_3$).

$^{19}$F-NMR (377 MHz, CHCl$_3$): δ=−114.0 (dd, 1F, J=12.7 Hz, J=7.9 Hz).

MS (EI): m/e (%)=324 (78, M$^+$), 295 (100, [M-Et]$^+$), 280 (21, [M-Et-Me]$^+$.
Δε=+4.4
Δn=0.2933
γ$_1$=77 mPa·s
C 41 N 99 I

EXAMPLE 4

2-(4'-Ethyl-3-fluorobiphenyl-4-yl)-5-pentylthiophene ("PGT-2-5")

The compound 2-(4'-ethyl-3-fluorobiphenyl-4-yl)-5-pentylthiophene ("PGT-2-5") according to the invention is prepared analogously to Example 3 by Wittig reaction of 5-(4'-ethyl-3-fluorobiphenyl-4-yl)thiophene-2-carbaldehyde and butyltriphenylphosphonium bromide and subsequent hydrogenation.

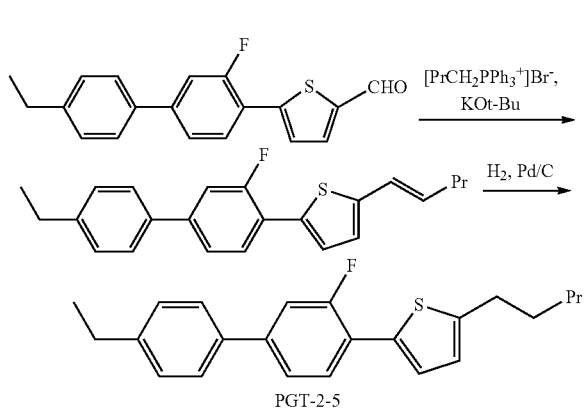

2-(4'-Ethyl-3-fluorobiphenyl-4-yl)-5-pentylthiophene ("PGT-2-5") is obtained as a colourless solid having an m.p. of 44° C.

$^1$H-NMR (400 MHz, CHCl$_3$): δ=7.62-7.58 (m, 1H, H$_{arom.}$), 7.50 (d, 2H, J=8.4 Hz, H$_{arom.}$), 7.36-7.35 (m, 1H, H$_{arom.}$), 7.34-7.30 (m, 2H, H$_{arom.}$), 7.26 (d, 2H, J=8.4 Hz, H$_{arom.}$), 6.78-6.76 (m, 1H, H$_{arom.}$), 2.83 (t, 2H, J=7.6 Hz, —CH$_2$(CH$_2$)$_3$CH$_3$), 2.68 (q, 2H, J=7.6 Hz, CH$_3$CH$_2$—), 1.75-1.68 (m, 2H, —CH$_2$(CH$_2$)$_3$CH$_3$), 1.40-1.33 (m, 4H, —CH$_2$(CH$_2$)$_3$CH$_3$), 1.27 (t, 3H, J=7.6 Hz, CH$_3$CH$_2$—), 0.93-0.89 (m, 3H, —CH$_2$(CH$_2$)$_3$CH$_3$).

$^{19}$F-NMR (377 MHz, CHCl$_3$): δ=113.9 (dd, 1F, J=12.8 Hz, J=8.0 Hz).

MS (EI): m/e (%)=352 (78, M$^+$), 295 (100, [M-Bu]$^+$), 280 (21, [M-Bu-Me]$^+$).
Δε=+3.8
Δn=0.2579
γ$_1$=82 mPa·s
C 44 N 99 I

EXAMPLE 5

2-Butyl-5-(4'-ethyl-3-fluorobiphenyl-4-yl)thiophene ("PGT-2-4")

The compound 2-butyl-5-(4'-ethyl-3-fluorobiphenyl-4-yl)thiophene ("PGT-2-4") according to the invention is prepared analogously to Example 3 by Wittig reaction of 5-(4'-ethyl-3-fluorobiphenyl-4-yl)thiophene-2-carbaldehyde and propyltriphenylphosphonium bromide and subsequent hydrogenation.

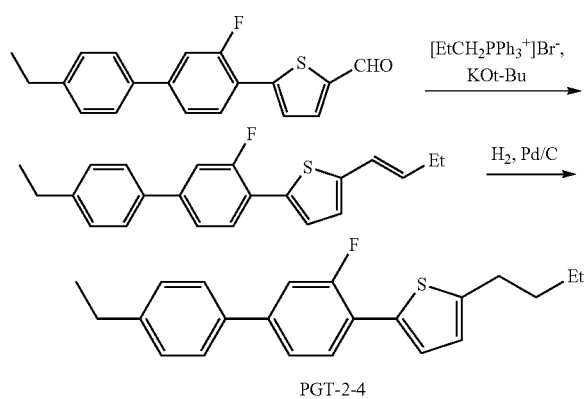
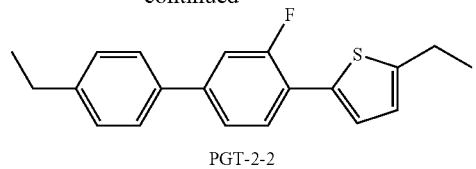

2-Butyl-5-(4'-ethyl-3-fluorobiphenyl-4-yl)thiophene ("PGT-2-4") is obtained as a colourless solid having an m.p. of 37° C.

$^1$H-NMR (400 MHz, CHCl$_3$): δ=7.62-7.58 (m, 1H, H$_{arom.}$), 7.52 (d, 2H, J=8.0 Hz, H$_{arom.}$), 7.38-7.35 (m, 1H, H$_{arom.}$), 7.34-7.30 (m, 2H, H$_{arom.}$), 7.28 (d, 2H, J=8.0 Hz, H$_{arom.}$), 6.80-6.78 (m, 1H, H$_{arom.}$), 2.85 (t, 2H, J=7.6 Hz, —CH$_2$(CH$_2$)$_2$CH$_3$), 2.70 (q, 2H, J=7.6 Hz, CH$_3$CH$_2$—), 1.74-1.67 (m, 2H, —CH$_2$(CH$_2$)$_2$CH$_3$), 1.48-1.38 (m, 2H, —CH$_2$(CH$_2$)$_2$CH$_3$), 1.28 (t, 3H, J=7.6 Hz, CH$_3$CH$_2$—), 0.96 (t, 3H, J=7.4 Hz, —CH$_2$(CH$_2$)$_3$CH$_3$).

$^{19}$F-NMR (377 MHz, CHCl$_3$): δ=−114.3 (dd, 1F, J=12.6 Hz, J=8.0 Hz).

MS (EI): m/e (%)=338 (79, M$^+$), 295 (100, [M-Pr]$^+$), 280 (29, [M-Pr-Me]$^+$).

Δ∈=+3.8

Δn=0.2733

γ$_1$=85 mPa·s

C 37 N 92 I

EXAMPLE 6

2-Ethyl-5-(4'-ethyl-3-fluorobiphenyl-4-yl)thiophene ("PGT-2-2")

The compound 2-ethyl-5-(4'-ethyl-3-fluorobiphenyl-4-yl)thiophene ("PGT-2-2") according to the invention is prepared analogously to Example 3 by Wittig reaction of 5-(4'-ethyl-3-fluorobiphenyl-4-yl)thiophene-2-carbaldehyde and methyltriphenylphosphonium bromide and subsequent hydrogenation.

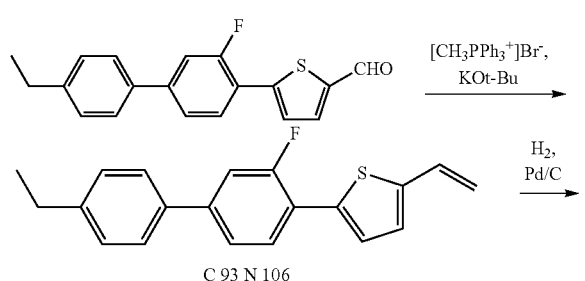

2-Ethyl-5-(4'-ethyl-3-fluorobiphenyl-4-yl)thiophene ("PGT-2-2") is obtained as a colourless solid having an m.p. of 67° C.

$^1$H-NMR (400 MHz, CHCl$_3$): δ=7.62-7.58 (m, 1H, H$_{arom.}$), 7.51 (d, 2H, J=8.4 Hz, H$_{arom.}$), 7.38-7.34 (m, 1H, H$_{arom.}$), 7.33-7.30 (m, 2H, H$_{arom.}$), 7.27 (d, 2H, J=8.4 Hz, H$_{arom.}$), 6.81-6.79 (m, 1H, H$_{arom.}$) 2.88 (dq, 2H, J=7.6 Hz, J=0.8 Hz, —CH$_2$CH$_3$), 2.69 (q, 2H, J=7.6 Hz, CH$_3$CH$_2$—), 1.35 (t, 3H, J=7.6 Hz, —CH$_2$CH$_3$), 1.27 (t, 3H, J=7.6 Hz, CH$_3$CH$_2$—).

$^{19}$F-NMR (377 MHz, CHCl$_3$): δ=−114.2 (dd, 1F, J=12.6 Hz, J=8.1 Hz).

MS (EI): m/e (%)=310 (100, M$^+$), 295 (100, [M-Me]$^+$), 280 (22, [M-Me-Me]$^+$).

Δ∈=+4.9

Δn=0.3026

γ$_1$=89 mPa·s

C 67 N 102 I

EXAMPLE 7

2-(3-Fluoro-4'-propylbiphenyl-4-yl)-5-methylthiophene ("PGT-3-1")

The compound 2-(3-fluoro-4'-propylbiphenyl-4-yl)-5-methylthiophene ("PGT-3-1") according to the invention is prepare analogously to Example 1 by Suzuki coupling of 4'-propyl-3-fluoro-4-biphenylboronic acid to 2-bromo-5-methylthiophene.

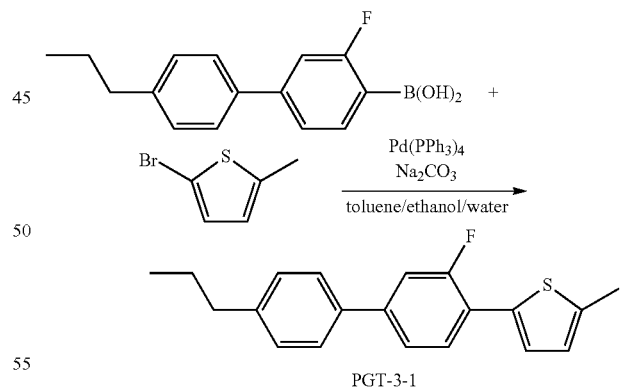

2-(3-Fluoro-4'-propylbiphenyl-4-yl)-5-methylthiophene ("PGT-3-1") is obtained as a colourless solid having an m.p. of 88° C. The $^1$H- and $^{19}$F-NMR spectroscopy data correspond to the structure.

MS (EI): m/e (%)=310 (100, M$^+$), 281 (78).

Δ∈=+2.3

Δn=0.3241

γ$_1$=147 mPa·s

C 88 N 137 I

EXAMPLE 8

2-Ethyl-5-(3-fluoro-4'-propylbiphenyl-4-yl)thiophene ("PGT-3-2")

5-(3-Fluoro-4'-propylbiphenyl-4-yl)thiophene-2-carbaldehyde is prepared analogously to Example 3 by Suzuki coupling of 4'-propyl-3-fluoro-4-biphenylboronic acid to 5-bromothiophene-2-carbaldehyde.

The compound 2-ethyl-5-(3-fluoro-4'-propylbiphenyl-4-yl)thiophene ("PGT-3-2") according to the is prepared analogously to Example 3 by Wittig reaction of 5-(3-fluoro-4'-propylbiphenyl-4-yl)thiophene-2-carbaldehyde and methyltriphenylphosphonium bromide and subsequent hydrogenation.

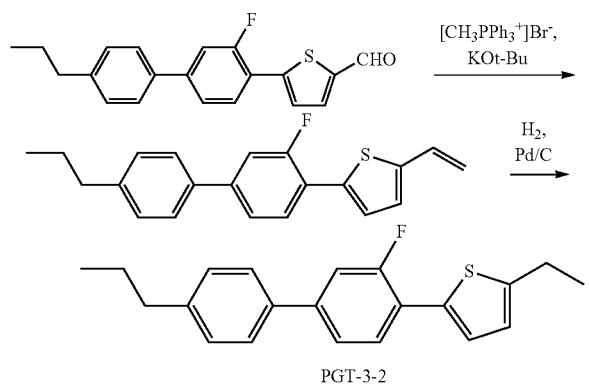

PGT-3-2

2-Ethyl-5-(3-fluoro-4'-propylbiphenyl-4-yl)thiophene ("PGT-3-2") is obtained as a colourless solid having an m.p. of 51° C. The $^1$H- and $^{19}$F-NMR spectroscopy data correspond to the structure.

MS (EI): m/e (%)=324 (100, M$^+$), 309 (64, [M-Me]$^+$), 295 (28, [M-Me-Me]$^+$), 280 (33, [M-Me-Et]$^+$).

Δ∈=+4.2
Δn=0.2993
$\gamma_1$=73 mPa·s
C 51 SmA 79 N 124 I

EXAMPLE 9

2-(3-Fluoro-4'-propylbiphenyl-4-yl)-5-propylthiophene ("PGT-3-3")

The compound 2-(3-fluoro-4'-propylbiphenyl-4-yl)-5-propylthiophene ("PGT-3-3") according to the invention is prepared analogously to Example 3 by Wittig reaction of 5-(3-fluoro-4'-propylbiphenyl-4-yl)thiophene-2-carbaldehyde and ethyltriphenylphosphonium bromide and subsequent hydrogenation.

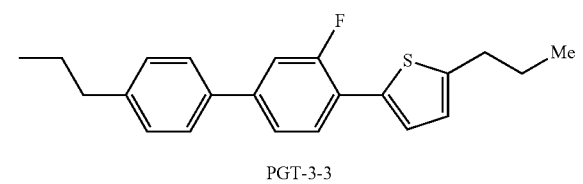 [SMILES: CCCc1ccc(-c2ccc(-c3ccc(CCC)s3)c(F)c2)cc1]

PGT-3-3

2-(3-Fluoro-4'-propylbiphenyl-4-yl)-5-propylthiophene ("PGT-3-3") is obtained as a colourless solid having an m.p. of 42° C. The $^1$H- and $^{19}$F-NMR spectroscopy data correspond to the structure.

MS (EI): m/e (%)=338 (72, M$^+$), 309 (100, [M-Et]$^+$), 280 (33, [M-Et-Et]$^+$).

Δ∈=+3.4
Δn=0.2873
$\gamma_1$=104 mPa·s
C 42 SmA 75 N 119 I

EXAMPLE 10

2-Butyl-5-(3-fluoro-4'-propylbiphenyl-4-yl)thiophene ("PGT-3-4")

The compound 2-butyl-5-(3-fluoro-4'-propylbiphenyl-4-yl)thiophene ("PGT-3-4") according to the invention is prepared analogously to Example 3 by Wittig reaction of 5-(3-fluoro-4'-propylbiphenyl-4-yl)thiophene-2-carbaldehyde and propyltriphenylphosphonium bromide and subsequent hydrogenation.

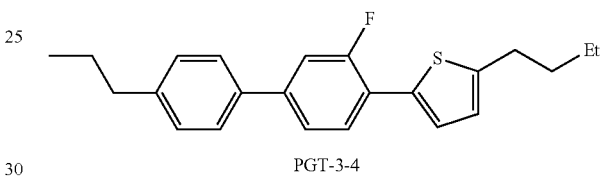

PGT-3-4

2-Butyl-5-(3-fluoro-4'-propylbiphenyl-4-yl)thiophene ("PGT-3-4") is obtained as a colourless wax-like solid. The $^1$H- and $^{19}$F-NMR spectroscopy data correspond to the structure.

MS (EI): m/e (%)=352 (78, M$^+$), 309 (100, [M-Pr]$^+$), 280 (33, [M-Pr-Et]$^+$).

Δ∈=+3.4
Δn=02789
$\gamma_1$=75 mPa·s
C 4 SmB 33 Sm 42 SmA 83 N 113 I

EXAMPLE 11

2-(3-Fluoro-4'-propylbiphenyl-4-yl)-5-pentylthiophene ("PGT-3-5")

The compound 2-(3-fluoro-4'-propylbiphenyl-4-yl)-5-pentylthiophene ("PGT-3-5") according to the invention is prepared analogously to Example 3 by Wittig reaction of 5-(3-fluoro-4'-propylbiphenyl-4-yl)thiophene-2-carbaldehyde and butyltriphenylphosphonium bromide and subsequent hydrogenation.

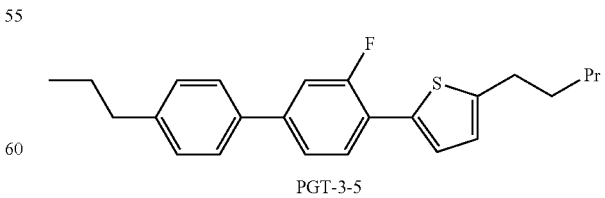

PGT-3-5

2-(3-Fluoro-4'-propylbiphenyl-4-yl)-5-pentylthiophene ("PGT-3-5") is obtained as a colourless solid having an m.p. of 35° C. The $^1$H- and $^{19}$F-NMR spectroscopy data correspond to the structure.

MS (EI): m/e (%)=366 (83, M$^+$), 309 (100, [M-Bu]$^+$), 280 (31, [M-Bu-Et]$^+$).
Δ∈=+3.0
Δn=0.2629
$\gamma_1$=115 mPa·s
C 35 SmB (28) SmC 54 SmA 81 N 116 I

EXAMPLE 12

2-(3-Fluoro-4'-pentylbiphenyl-4-yl)-5-methylthiophene ("PGT-5-1")

The compound 2-(3-fluoro-4'-pentylbiphenyl-4-yl)-5-methylthiophene ("PGT-5-1") according to the invention is prepared analogously to Example 1 by Suzuki coupling of 4'-pentyl-3-fluoro-4-biphenylboronic acid to 2-bromo-5-methylthiophene.

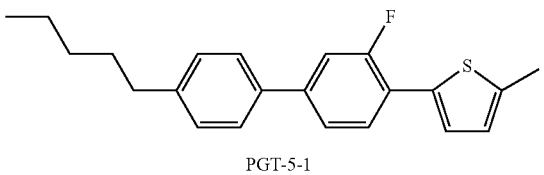 [SMILES: CCCCCc1ccc(-c2ccc(-c3ccc(C)s3)c(F)c2)cc1]

PGT-5-1

2-(3-Fluoro-4'-pentylbiphenyl-4-yl)-5-methylthiophene ("PGT-5-1") is obtained as a colourless solid having an m.p. of 65° C. The $^1$H- and $^{19}$F-NMR spectroscopy data correspond to the structure.
MS (EI): m/e (%)=338 (100, M$^+$), 281 (78).
Δ∈=+3.8
Δn=0.2977
$\gamma_1$=162 mPa·s
C 65 SmA 105 N 138 I

EXAMPLE 13

2-Fluoro-5-(3-fluoro-4'-propylbiphenyl-4-yl)thiophene ("PGT-3-F")

The compound 2-fluoro-5-(3-fluoro-4'-propylbiphenyl-4-yl)thiophene ("PGT-3-F") according to the invention is prepared as described below:

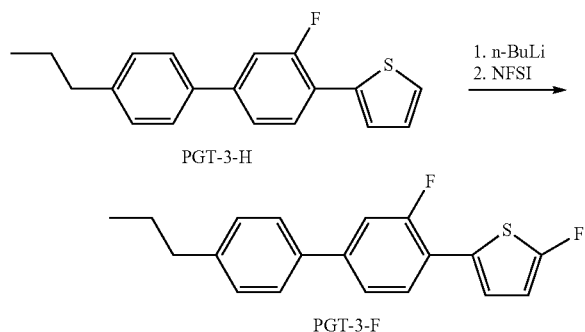

4.0 g (13.5 mmol) of 2-(4'-propyl-3-fluorobiphenyl-4-yl) thiophene ("PGT-3-H") are initially introduced at −20° C. in THF, and 9.3 ml (14.8 mmol) of n-BuLi (15% solution in hexane) are added dropwise. The mixture is warmed to 0° C. and stirred at this temperature for 30 min. The batch is cooled to −78° C., and a solution of 5.11 g (16.2 mmol) of N-fluorobenzenesulfonimide (NFSI) in THF is metered in. After 30 min at −78° C., the batch is warmed to room temperature. Water is added, and the mixture is extracted a number of times with MTBE. The combined organic phases are washed with water and sat. sodium chloride solution and dried using sodium sulfate. The solution is evaporated to dryness, and the residue is purified by chromatography (SiO$_2$, n-pentane). The further purification is carried out by recrystallisation from ethanol and n-heptane, giving 2-fluoro-5-(3-fluoro-4'-propylbiphenyl-4-yl)thiophene ("PGT-3-F") as a colourless solid having an m.p. of 64° C.
$^1$H-NMR (400 MHz, CHCl$_3$): δ=7.57-7.49 (m, 3H, H$_{arom.}$), 7.40-7.33 (m, 2H, H$_{arom.}$), 7.26 (d, 2H, J=8.4 Hz, H$_{arom.}$), 6.81-6.79 (m, 1H, H$_{arom.}$), 2.63 (t, 2H, J=7.5 Hz, CH$_3$CH$_2$CH$_2$—), 1.73-1.63 (m, 2H, CH$_3$CH$_2$CH$_2$—), 0.97 (t, 3H, J=7.4 Hz, CH$_3$CH$_2$CH$_2$—).
$^{19}$F-NMR (377 MHz, CHCl$_3$): δ=−115.2 (m, 1F), −131.0 (m, 1F).
MS (EI): m/e (%)=314 (93, M$^+$), 285 (100, [M-Et]$^+$).
Δ∈=+7.4
Δn=0.2917
$\gamma_1$=129 mPa·s
C 64 Sm 81 SmA 139 N 144 I

COMPARATIVE EXAMPLE 1

2-(2-Fluoro-4'-pentylbiphenyl-4-yl)-hexylthiophene (corresponding to example compound "(I-4)" on page 38 of EP 0 467 260 B1)

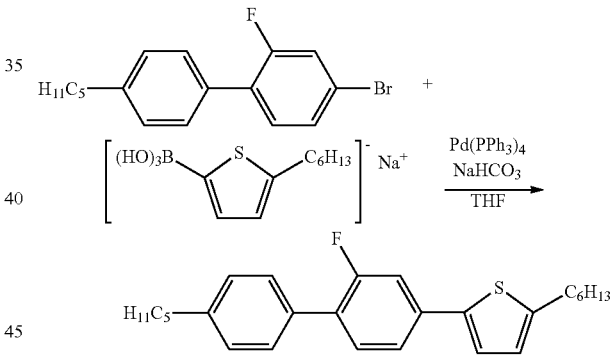

A mixture of 3.30 g (13.1 mmol) of 5-hexylthiophen-2-ylhydroxyboronic acid sodium salt, 4.20 g (13.1 mmol) of 4-bromo-2-fluoro-4'-pentylbiphenyl, 2.2 g (26.2 mmol) of sodium hydrogencarbonate and 0.70 g (0.61 mmol) of tetrakis(triphenylphosphine)palladium(0) in THF/water (1:1) is refluxed for 6 h. The mixture is diluted with MTBE, and the organic phase is separated off. The aqueous phase is extracted with MTBE. The combined organic phases are washed with sat. sodium chloride solution and dried using sodium sulfate. The solution is evaporated to dryness, and the residue is purified by column chromatography (SiO$_2$, n-heptane). The further purification is carried out by recrystallisation from methanol/-pentane (5:1). 2-(2-Fluoro-4'-pentylbiphenyl-4-yl)-5-hexylthiophene is obtained as a colourless solid having an m.p. of 44° C.
$^1$H-NMR (400 MHz, CHCl$_3$): δ=7.47 (dd, 2H, J=8.6 Hz, J=1.7 Hz, H$_{arom.}$), 7.42-7.35 (m, 2H, H$_{arom.}$), 7.31-7.30 (d, 1H, J=12.0 Hz, H$_{arom.}$), 7.26 (d, 2H, J=8.4 Hz, H$_{arom.}$), 7.17 (d, 1H, J=3.3 Hz, H$_{arom.}$), 6.76 (d, 1H, J=3.3 Hz, H$_{arom.}$), 2.82 (t, 2H, J=7.6 Hz, —CH$_2$(CH$_2$)$_4$CH$_3$), 2.68 (t, 2H, J=7.8 Hz, H₃C(CH₂)₃CH₂—), 1.75-1.60 (m, 4H, —(CH₂)—), 1.44-1.27 (m, 10H, —(CH₂)—), 0.94-0.86 (m, 6H, H₃C(CH₂)₃CH₂—, —CH₂(CH₂)₄CH₃).

$^{19}$F-NMR (282 MHz, CHCl₃): δ=−118.0 (dd, 1F, J=12.0 Hz, J=7.6 Hz).

MS (EI): m/e (%)=408 (100, M⁺), 337 (77, [M-Pent]⁺), 280 (21, [M-Pent-Bu]⁺).

Δε=+3.2
Δn=0.2311
γ₁=153 mPa·s
C 44 Sm (6) SmB (38) SmC 68 SmA 75 N 94 I

COMPARATIVE EXAMPLE 2

2-Butyl-5-(3-fluoro-4'-hexyloxybiphenyl-4-yl)thiophene (corresponding to example compound "(I-6)" on page 39 of EP 0 467 260 B1)

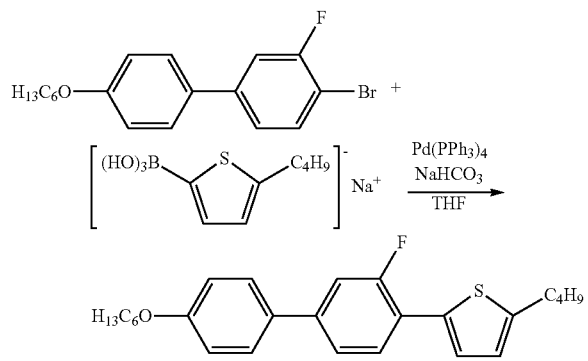

A mixture of 4.48 g (20.0 mmol) of 5-butylthiophen-2-ylhydroxyboronic acid sodium salt, 7.0 g (19.9 mmol) of 4-bromo-3-fluoro-4'-hexyloxybiphenyl, 3.36 g (40.0 mmol) of sodium hydrogencarbonate and 1.1 g (0.95 mmol) of tetrakis(triphenylphosphine)palladium(0) in 90 ml of THF/water (2:1) is refluxed for 19 h. The mixture is diluted with MTBE, and the organic phase is separated off. The aqueous phase is extracted with MTBE. The combined organic phases are washed with sat. sodium chloride solution and dried using sodium sulfate. The solution is evaporated to dryness, and the residue is purified by column chromatography (SiO₂, n-heptane:toluene=9:1). The further purification is carried out by recrystallisation from ethanol. 2-Butyl-5-(3-fluoro-4'-hexyloxybiphenyl-4-yl)-thiophene is obtained as a colourless wax having an m.p. of 66° C.

$^{1}$H-NMR (300 MHz, CHCl₃): δ=7.62-7.57 (m, 1H, H$_{arom.}$), 7.52 (d, 2H, J=8.2 Hz, H$_{arom.}$), 7.35-7.28 (m, 3H, H$_{arom.}$), 7.96 (d, 2H, J=8.2 Hz, H$_{arom.}$), 6.80-6.78 (m, 1H, H$_{arom.}$), 3.99 (t, 2H, J=6.1 Hz, OCH₂(CH₂)₄CH₃), 2.85 (t, 2H, J=7.2 Hz, CH₂(CH₂)₂CH₃), 1.85-1.65 (m, 4H, H$_{aliph.}$), 1.54-1.31 (8H, H$_{aliph.}$), 0.99-0.89 (m, 6H, 2×CH₃).

$^{19}$F-NMR (282 MHz, CHCl₃): δ=−114.2 (dd, 1F, J=12.7 Hz, J=8.2 Hz).

MS (EI): m/e (%)=410 (100, M⁺), 367 (31, [M-propyl]⁺), 283 (51, [M-propyl-hexyl]⁺).

Δε=+8.9
Δn=0.2749
γ₁=262 mPa·s
C 66 SmE 89 SmC 131 SmA 144 N 146 I

COMPARATIVE EXAMPLE 3

2-(3-Fluoro-4-pentylphenyl)-5-p-tolylthiophene (corresponding to example compound I-1 on page 12 of EP 0 467 260 B1)

Synthesis of 2-(3-fluoro-4-pentylphenyl)thiophene

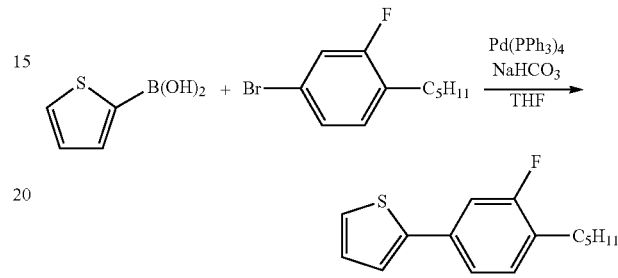

A mixture of 40.0 g (0.31 mol) of thiophen-2-ylboronic acid, 80.0 g (0.32 mol) of 4-bromo-2-fluoro-1-pentylbenzene, 18.0 g (15.6 mmol) of tetrakis(triphenylphosphine)palladium(0) and 400 ml of 2 M sodium hydrogencarbonate solution in 1000 ml of ethanol/toluene=3:2 is heated at 80° C. for 19 h. Toluene and water are added to the mixture, and the organic phase is separated off. The aqueous phase is extracted with toluene, and the combined organic phases are washed with sat. sodium chloride solution. The solution is dried using sodium sulfate and evaporated to dryness. The residue is purified by column chromatography (SiO₂, n-heptane). 2-(3-Fluoro-4-pentylphenyl)thiophene is obtained as a colourless liquid.

Synthesis of 2-bromo-5-(3-fluoro-4-pentylphenyl)thiophene

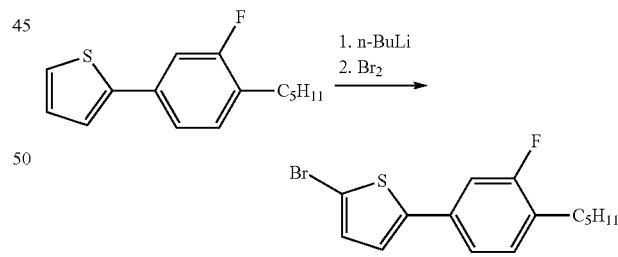

20.0 g (80.5 mmol) of 2-(3-fluoro-4-pentylphenyl)thiophene are initially introduced in 200 ml of THF, and 50.0 ml of n-BuLi (79.6 mmol, 15% solution in hexane) are added dropwise to the solution at a temperature in the range 0-5° C. After 1 h at 0° C., the batch is cooled to −70° C., and 4.1 ml (80.0 mmol) of bromine are metered in. When the addition is complete, the mixture is stirred at 0° C. for 1 h. The batch is diluted with MTBE and washed successively with 2 N HCl, 10% sodium hydrogensulfite solution, sat. sodium hydrogencarbonate solution and sat. sodium chloride solution. The solution is dried using sodium sulfate and evaporated to dryness. The crude product is purified by column chromatography (SiO$_2$, n-heptane). 2-Bromo-5-(3-fluoro-4-pentylphenyl)thiophene is obtained as a yellowish liquid.

Synthesis of
2-(3-fluoro-4-pentylphenyl)-5-p-tolylthiophene

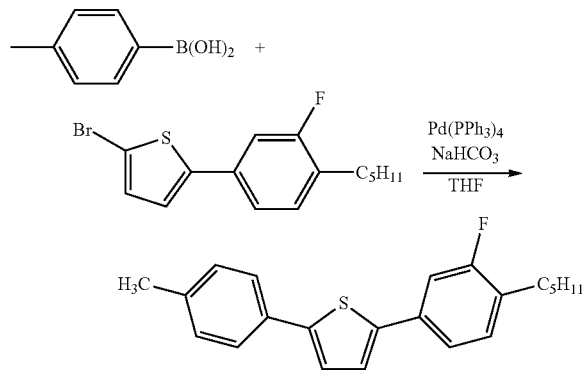

A mixture of 3.54 g (26.0 mmol) of p-tolylboronic acid, 8.50 g (26.0 mmol) of 2-bromo-5-(3-fluoro-4-pentylphenyl)thiophene, 1.50 g (1.30 mmol) of tetrakis(triphenylphosphine)palladium(0) and 33 ml of 2 M sodium hydrogencarbonate solution in 80 ml of ethanol/toluene=3:2 is heated at 80° C. for 20 h. Toluene and water are added to the mixture, and the organic phase is separated off. The aqueous phase is extracted with toluene, and the combined organic phases are washed with sat. sodium chloride solution. The solution is dried using sodium sulfate and evaporated to dryness. The residue is purified by column chromatography (SiO$_2$, toluene). The further purification is carried out by recrystallisation from ethanol and n-heptane. 2-(3-Fluoro-4-pentylphenyl)-5-p-tolylthiophene is obtained as a solid having an m.p. of 115° C.

$^1$H-NMR (300 MHz, CHCl$_3$): δ=7.53-7.49 (m, 2H, H$_{arom.}$), 7.32-7.37 (m, 2H, H$_{arom.}$), 7.24-7.13 (m, 5H, H$_{arom.}$), 2.63 (t, 2H, J=7.7 Hz, —CH$_2$(CH$_2$)$_3$CH$_3$), 2.36 (s, 3H, Me), 1.67-1.56 (m, 2H, H$_{aliph.}$), 1.39-1.29 (m, 4H, H$_{aliph.}$), 0.90 (t, 3H, J=6.9 Hz, —CH$_2$(CH$_2$)$_3$CH$_3$).

$^{19}$F-NMR (282 MHz, CHCl$_3$): δ=−118.6 (dd, 1F, J=11.0 Hz, J=8.2 Hz).

MS (EI): m/e (%)=338 (92, M$^+$), 281 (100, [M-butyl]$^+$).

Δε=+3.7
Δn=0.1877
γ$_1$=196 mPa·s
C 115 N 119 I

COMPARATIVE EXAMPLE A

A nematic LC mixture is formulated as follows:

| | | | |
|---|---|---|---|
| PGUQU-3-F | 6.00% | Cl.p. | +89.5 |
| PUQU-3-F | 8.00% | Δn | 0.1312 |
| GGP-3-Cl | 4.00% | Δε | +7.0 |
| PCH-3Cl | 3.00% | ε$_∥$ | 10.3 |
| CC-3-V | 31.00% | K$_3$/K$_1$ | 1.07 |
| CCP-V-1 | 16.00% | γ$_1$ | 79 |
| CCP-V2-1 | 8.00% | V$_0$ | 1.47 |
| PGP-2-3 | 7.00% | | |
| PGP-2-4 | 3.00% | | |
| APUQU-2-F | 5.00% | | |
| PGU-2-F | 4.00% | | |

-continued

| | |
|---|---|
| PGU-3-F | 2.00% |
| CPGP-4-3 | 3.00% |

MIXTURE EXAMPLE A

A nematic LC mixture according to the invention is formulated as follows:

| | | | |
|---|---|---|---|
| PGUQU-3-F | 6.00% | Cl.p. | 88.0 |
| PUQU-3-F | 9.00% | Δn | 0.1296 |
| GGP-3-Cl | 4.00% | Δε | 6.9 |
| PCH-3Cl | 3.00% | ε$_∥$ | 10.2 |
| CC-3-V | 31.00% | K$_3$/K$_1$ | 1.05 |
| CCP-V-1 | 16.00% | γ$_1$ | 77 |
| CCP-V2-1 | 8.00% | V$_0$ | 1.50 |
| PGP-2-3 | 7.00% | | |
| PGP-2-4 | 5.00% | | |
| APUQU-2-F | 8.00% | | |
| PGT-2-1 | 3.00% | | |

The mixture has a lower rotational viscosity compared with Comparative Mixture A, with virtually unchanged values of the clearing point, the dielectric anisotropy, the birefringence and the threshold voltage.

COMPARATIVE EXAMPLE B

A nematic LC mixture is formulated as follows:

| | | | |
|---|---|---|---|
| CC-3-V | 44.00% | Cl.p. | +74.5 |
| PGUQU-3-F | 13.00% | Δn | 0.1353 |
| CPGU-3-OT | 5.50% | Δε | +8.0 |
| APUQU-3-F | 7.50% | ε$_∥$ | 11.3 |
| PUQU-3-F | 4.00% | γ$_1$ | 66 |
| PP-1-2V1 | 8.00% | V$_{10}$ | 1.57 |
| PGP-2-3 | 5.00% | | |
| PGP-2-4 | 8.00% | | |
| PGP-2-5 | 5.00% | | |

MIXTURE EXAMPLE B

A nematic LC mixture according to the invention is formulated as follows:

| | | | |
|---|---|---|---|
| CC-3-V | 52.00% | Cl.p. | +78.5 |
| PGUQU-3-F | 13.00% | Δn | 0.1355 |
| CPGU-3-OT | 5.00% | Δε | +8.2 |
| APUQU-3-F | 6.00% | ε$_∥$ | 11.4 |
| PUQU-3-F | 6.00% | γ$_1$ | 57 |
| PGT-2-1 | 18.00% | V$_{10}$ | 1.56 |

The mixture has a significantly higher clearing point and a significantly lower rotational viscosity compared with Comparative Mixture B, with virtually unchanged values of the dielectric anisotropy, the birefringence and the threshold voltage.

COMPARATIVE EXAMPLE C

A nematic LC mixture is formulated as follows:

| | | | |
|---|---|---|---|
| PUQU-3-F | 8.00% | Cl.p. | +83.0 |
| PGUQU-3-F | 5.00% | $\Delta n$ | 0.1023 |
| CCP-V-1 | 13.00% | $\Delta \epsilon$ | +7.8 |
| CCP-V2-1 | 9.00% | $\epsilon_{\parallel}$ | 11.0 |
| CC-3-V | 44.00% | $\gamma_1$ | 66 |
| APUQU-2-F | 8.00% | $V_0$ | 1.36 |
| APUQU-3-F | 8.00% | | |
| PGP-2-4 | 5.00% | | |

MIXTURE EXAMPLE C

A nematic LC mixture according to the invention is formulated as follows:

| | | | |
|---|---|---|---|
| PUQU-3-F | 6.00% | Cl.p. | +83.5 |
| PGUQU-3-F | 6.00% | $\Delta n$ | 0.1025 |
| CCP-V-1 | 12.00% | $\Delta \epsilon$ | +7.7 |
| CCP-V2-1 | 8.00% | $\epsilon_{\parallel}$ | 10.9 |
| CC-3-V | 47.00% | $\gamma_1$ | 62 |
| APUQU-2-F | 8.00% | $V_o$ | 1.37 |
| APUQU-3-F | 9.00% | | |
| PGT-2-1 | 4.00% | | |

The mixture has a lower rotational viscosity compared with Comparative Mixture C, with virtually unchanged values of the clearing point, the dielectric anisotropy, the birefringence and the threshold voltage.

MIXTURE EXAMPLE D

A nematic LC mixture according to the invention is formulated as follows:

| | | | |
|---|---|---|---|
| PUQU-3-F | 7.00% | Cl.p. | +74.5 |
| PGUQU-3-F | 12.00% | $\Delta n$ | 0.1336 |
| CC-3-V | 49.50% | $\Delta \epsilon$ | +8.0 |
| PP-1-2V1 | 2.50% | $\epsilon_{\parallel}$ | 11.2 |
| CPGU-3-OT | 5.50% | $\gamma_1$ | 58 |
| APUQU-3-F | 5.50% | $V_o$ | 1.58 |
| PGT-2-1 | 6.00% | | |
| PGT-2-3 | 6.00% | | |
| PGT-2-5 | 6.00% | | |

MIXTURE EXAMPLE E

A nematic LC mixture according to the invention is formulated as follows:

| | | | |
|---|---|---|---|
| PUQU-3-F | 16.00% | Cl.p. | +74.0 |
| PGUQU-3-F | 8.00% | $\Delta n$ | 0.1323 |
| CC-3-V | 46.00% | $\Delta \epsilon$ | +7.5 |
| CCP-V-1 | 7.00% | $\epsilon_{\parallel}$ | 10.6 |
| PGP-2-2V | 2.00% | $\gamma_1$ | 56 |
| CPGU-3-OT | 5.00% | $V_o$ | 1.57 |
| PGT-2-1 | 16.00% | | |

MIXTURE EXAMPLE F

A nematic LC mixture according to the invention is formulated as follows:

| | | | |
|---|---|---|---|
| PUQU-3-F | 9.00% | Cl.p. | +75.0 |
| PGUQU-3-F | 9.00% | $\Delta n$ | 0.1321 |
| CC-3-V | 44.50% | $\Delta \epsilon$ | +7.6 |
| PP-1-2V1 | 2.00% | $\epsilon_{\parallel}$ | 10.9 |
| PGP-2-2V | 11.00% | $\gamma_1$ | 56 |
| CPGU-3-OT | 4.50% | $V_o$ | 1.54 |
| CPU-3-OXF | 15.00% | | |
| PGT-2-2 | 5.00% | | |

MIXTURE EXAMPLE G

A nematic LC mixture according to the invention is formulated as follows:

| | | | |
|---|---|---|---|
| PGUQU-3-F | 6.00% | Cl.p. | +76.0 |
| CC-3-V | 53.00% | $\Delta n$ | 0.1162 |
| CCP-V-1 | 9.00% | $\Delta \epsilon$ | +4.2 |
| PP-1-2V1 | 8.00% | $\epsilon_{\parallel}$ | 7.0 |
| CPGU-3-OT | 6.00% | $\gamma_1$ | 48 |
| APUQU-3-F | 6.50% | $V_o$ | 2.09 |
| PGT-2-2 | 11.00% | | |

MIXTURE EXAMPLE H

A nematic LC mixture according to the invention is formulated as follows:

| | | | |
|---|---|---|---|
| PGUQU-3-F | 7.00% | Cl.p. | +75.0 |
| CC-3-V | 56.00% | $\Delta n$ | 0.1168 |
| CCP-3-1 | 2.50% | $\Delta \epsilon$ | +4.1 |
| CPU-3-OXF | 20.00% | $\epsilon_{\parallel}$ | 7.0 |
| PGT-2-2 | 14.50% | $\gamma_1$ | 42 |

MIXTURE EXAMPLE I

A nematic LC mixture according to the invention is formulated as follows:

| | | | |
|---|---|---|---|
| PUQU-3-F | 5.50% | Cl.p. | +75.5 |
| PGUQU-3-F | 8.00% | $\Delta n$ | 0.1310 |
| CC-3-V | 42.00% | $\Delta \epsilon$ | +4.6 |
| PP-1-2V1 | 8.50% | $\epsilon_{\parallel}$ | 7.5 |
| CC-3-V1 | 8.00% | $\gamma_1$ | 50 |
| CCP-V2-1 | 6.00% | $V_o$ | 2.08 |
| CPGU-3-OT | 6.00% | | |
| PGT-2-2 | 16.00% | | |

The invention claimed is:

1. A LC medium which has a nematic phase at room temperature, comprising one or more compounds of formula I

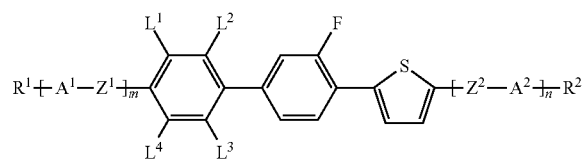

I in which
R[1] and R[2] denote H, F, Cl, Br, —CN, —SCN, SF$_5$ or straight-chain or branched alkyl having 1 to 12 C atoms, in which one or more non-adjacent CH$_2$ groups may each be replaced, independently of one another, by —CH=CH—, —CO—, —CO—O—, —O—CO—, or —O—CO—O— in such a way that O atoms are not linked directly to one another, and in which one or more H atoms may be replaced by F, Cl or Br, or P-Sp-, P denotes a polymerizable group, Sp denotes a spacer group or a single bond, A[1] and A[2] each, independently of one another, denote phenylene-1,4-diyl, in which one or two CH groups may be replaced by N and one or more H atoms may be replaced by halogen, CN, CH$_3$, CHF$_2$, CH$_2$F, OCH$_3$, OCHF$_2$ or OCF$_3$, cyclohexane-1,4-diyl, in which one or two non-adjacent CH$_2$ groups may be replaced, independently of one another, by O and/or S and one or more H atoms may be replaced by F, or denote cyclohexene-1,4-diyl, bicyclo[1.1.1]-pentane-1,3-diyl, bicyclo[2.2.2]octane-1,4-diyl, spiro[3.3]heptane-2,6-diyl, tetrahydropyran-2,5-diyl or 1,3-dioxane-2,5-diyl, Z[1] and Z[2] each, independently of one another, denote —CF$_2$O—, —OCF$_2$—, —CH$_2$O—, —OCH$_2$—, —CO—O—, —O—CO—, —C$_2$H$_4$—, —C$_2$F$_4$—, —CF$_2$CH$_2$—, —CH$_2$CF$_2$—, —CFHCFH—, —CFHCH$_2$—, —CH$_2$CFH—, —CF$_2$CFH—, —CFHCF$_2$—, —CH=CH—, —CF=CH—, —CH=CF—, —CF=CF—, —C≡C— or a single bond, L[1-4] each, independently of one another, denote H, halogen, CF$_3$ or CN, and m and n each, independently of one another, denote 0, 1 or 2.

2. A LC medium according to claim 1, wherein the compounds of formula I is one of the following formulae:

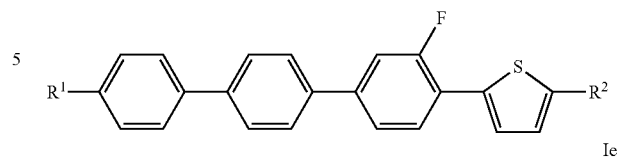

Ia

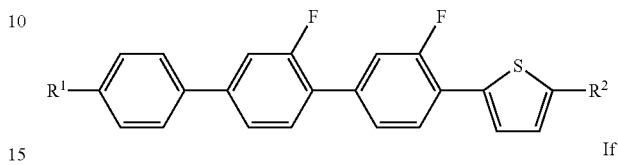

Ib

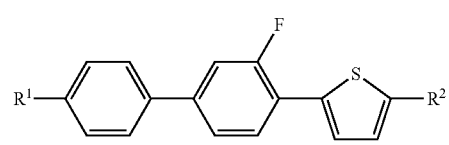

Ic

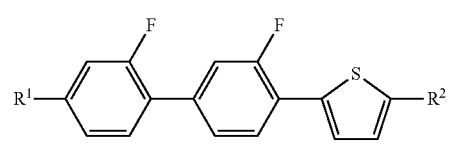

Id

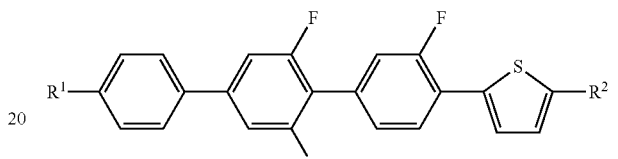

Ie

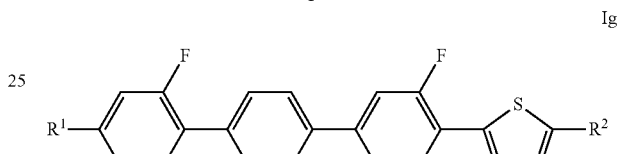

If

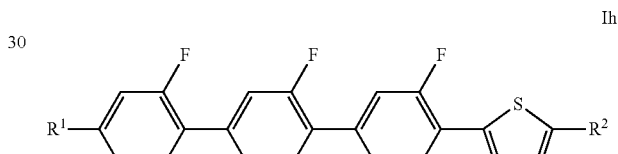

Ig

Ih

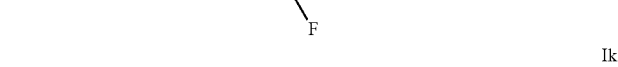

Ii

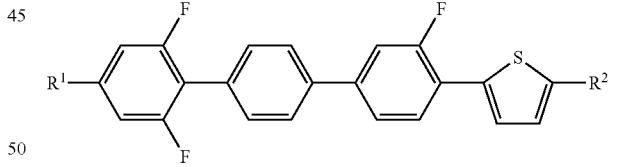

Ik

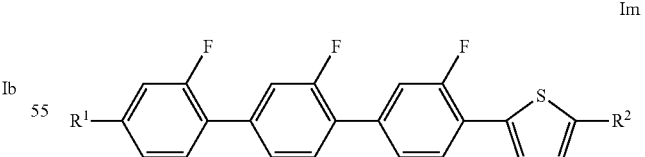

Im

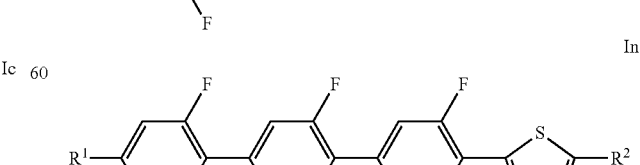

In

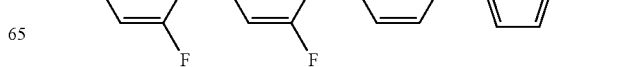

-continued

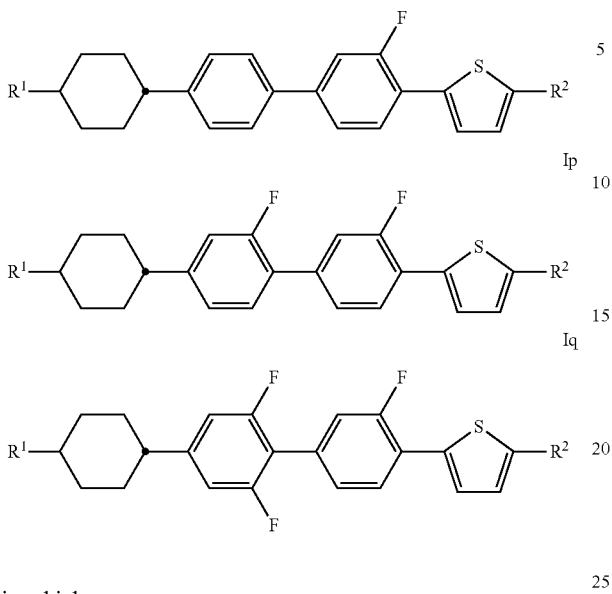

in which
R¹ and R² have the meanings indicated for the compound of formula I.

3. A LC medium according to claim 1, comprising one or more compounds of formulae II and/or III:

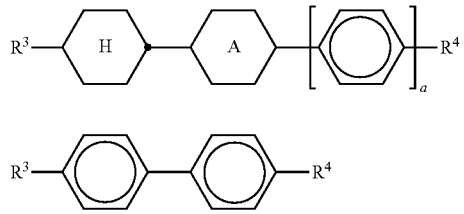

in which

A denotes 1,4-phenylene or trans-1,4-cyclohexylene, a is 0 or 1,

R³ denotes alkenyl having 2 to 9 C atoms, and

R⁴ denotes alkyl having 1 to 12 C atoms, in which one or two non-adjacent CH₂ groups may be replaced by —O—, —CH=CH—, —CO—, —OCO— or —COO— in such a way that O atoms are not linked directly to one another.

4. A LC medium according to claim 1, comprising one or more compounds of the following formulae:

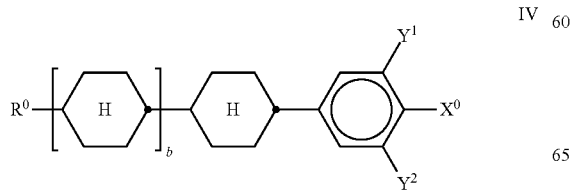

-continued

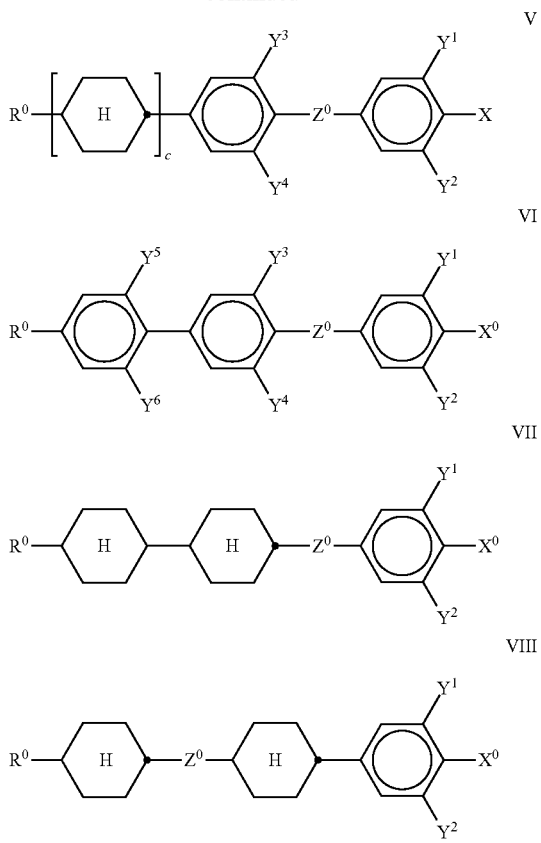

in which

R⁰ denotes an alkyl or alkoxy radical having 1 to 15 C atoms, in which one or more CH₂ groups in these radicals may each be replaced, independently of one another, by —C≡C—, —CF₂O—, —CH=CH—,

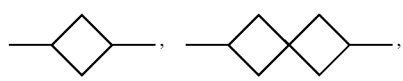

—O—, —CO—O— or —O—CO— in such a way that O atoms are not linked directly to one another, and in which one or more H atoms may be replaced by halogen, X⁰ denotes F, Cl, CN, SF₅, SCN, NCS, or a halogenated alkyl radical, halogenated alkenyl radical, halogenated alkoxy radical or halogenated alkenyloxy radical, each having up to 6 C atoms, Y¹⁻⁶ each, independently of one another, denote H or F, Z⁰ denotes —C₂H₄—, —(CH₂)₄—, —CH=CH—, —CF=CF—, —C₂F₄—, —CH₂CF₂—, —CF₂CH₂—, —CH₂O—, —OCH₂—, —COO—, —CF₂O— or —OCF₂—, and in formulae V and VI also a single bond, and b and c each, independently of one another, denote 0 or 1.

5. A LC medium according to claim 1, comprising one or more of the following formulae:

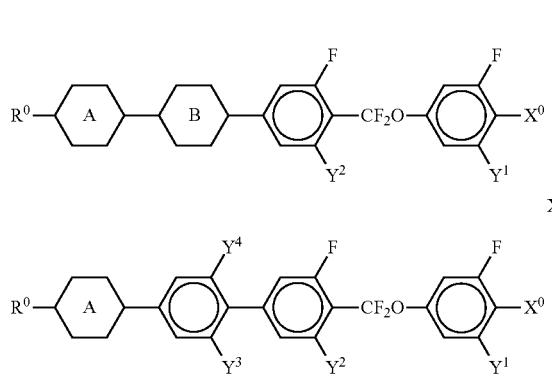

in which
R⁰ denotes an alkyl or alkoxy radical having 1 to 15 C atoms, in which one or more CH$_2$ groups in these radicals may each be replaced, independently of one another, by —C≡C—, —CF$_2$O—, —CH=CH—,

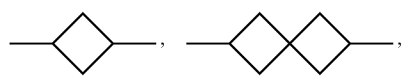

—O—, —CO—O— or —O—CO— in such a way that O atoms are not linked directly to one another, and in which one or more H atoms may be replaced by halogen, X⁰ denotes F, Cl, CN, SF$_5$, SCN, NCS, or a halogenated alkyl radical, halogenated alkenyl radical, halogenated alkoxy radical or halogenated alkenyloxy radical, each having up to 6 C atoms, and Y$^{1-4}$ each, independently of one another, denote H or F, and

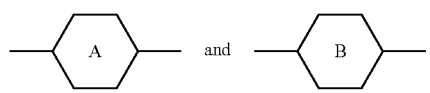

each, independently of one another, denote

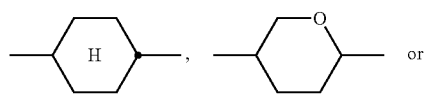

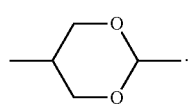

6. A LC medium according to claim 1, comprising one or more compounds of the following formula:

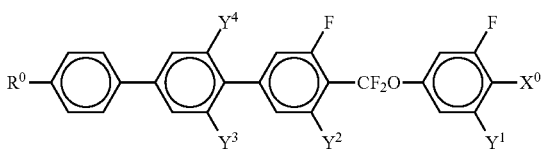

in which
R⁰ denotes an alkyl or alkoxy radical having 1 to 15 C atoms, in which one or more CH$_2$ groups in these radicals may each be replaced, independently of one another, by —C≡C—, —CF$_2$O—, —CH=CH—,

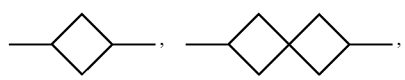

—O—, —CO—O— or —O—CO— in such a way that O atoms are not linked directly to one another, and in which one or more H atoms may be replaced by halogen, X⁰ denotes F, Cl, CN, SF$_5$, SCN, NCS, or a halogenated alkyl radical, halogenated alkenyl radical, halogenated alkoxy radical or halogenated alkenyloxy radical, each having up to 6 C atoms, and Y$^{1-4}$ each, independently of one another, denote H or F.

7. A compound of formula I

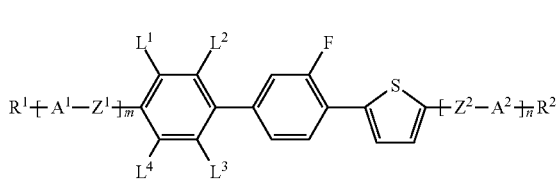

in which
R¹ and R² denote H, F, Cl, Br, —CN, —SCN, SF$_5$, P-Sp-, or straight-chain or branched, optionally fluorinated alkyl, alkenyl or alkynyl having 1 to 8 C atoms, P denotes a polymerizable group, Sp denotes a spacer group or a single bond, A¹ and A² each, independently of one another, denote phenylene-1,4-diyl, in which one or two CH groups may be replaced by N and one or more H atoms may be replaced by halogen, CN, CH$_3$, CHF$_2$, CH$_2$F, OCH$_3$, OCHF$_2$ or OCF$_3$, cyclohexane-1,4-diyl, in which one or two non-adjacent CH$_2$ groups may be replaced, independently of one another, by O and/or S and one or more H atoms may be replaced by F, or denote cyclohexene-1,4-diyl, bicyclo[1.1.1]-pentane-1,3-diyl, bicyclo[2.2.2]octane-1,4-diyl, spiro[3.3]heptane-2,6-diyl, tetrahydropyran-2,5-diyl or 1,3-dioxane-2,5-diyl, Z¹ and Z² each, independently of one another, denote —CF$_2$O—, —OCF$_2$—, —CH$_2$O—, —OCH$_2$—, —CO—O—, —O—CO—, —C$_2$H$_4$— —C$_2$F$_4$—, —CF$_2$CH$_2$—, —CH$_2$CF$_2$—, —CFHCFH—, —CFHCH$_2$—, —CH$_2$CFH—, —CF$_2$CFH—, —CFHCF$_2$—, —CH=CH—, —CF=CH—, —CH=CF—, —CF=CF—, —C≡C— or a single bond, L$^{1-4}$ each, independently of one another, denote H, halogen, CF$_3$ or CN, and m and n each, independently of one another, denote 0, 1 or 2.

8. A compound according to claim 7, n denotes 0, m denotes 0 or 1, $A^1$ denotes phenylene-1,4-diyl, which may also be mono- or polysubstituted by F, $Z^1$ denotes a single bond, and $L^1$-$L^4$ each, independently of one another, denote H or F.

9. A compound according to claim 7, which is a compound of one of the following formulae:

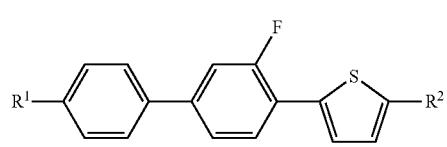
Ia

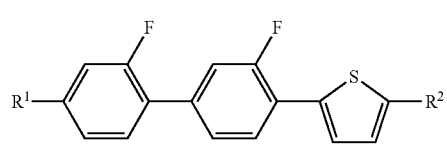
Ib

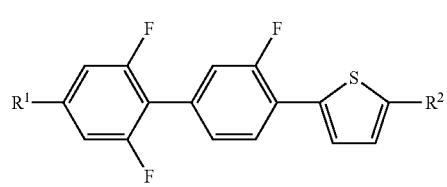
Ic

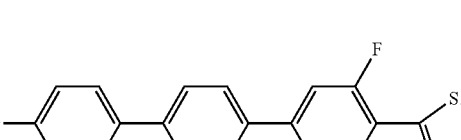
Id

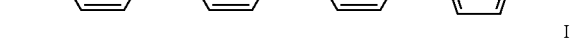
Ie

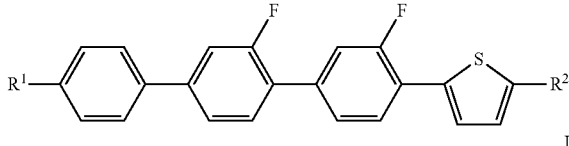
If

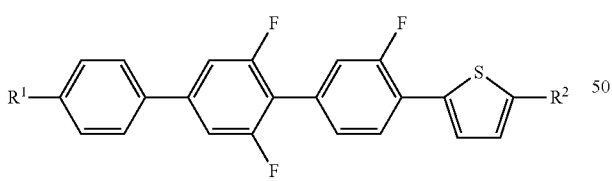
Ig

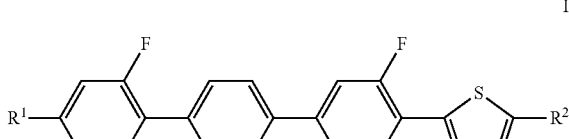
Ih

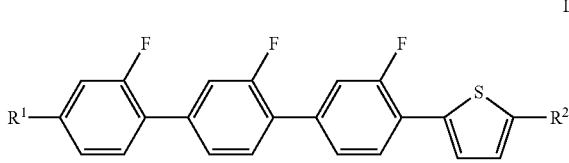

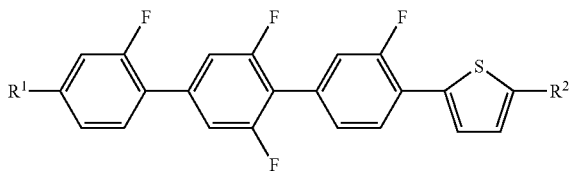
Ii

Ik

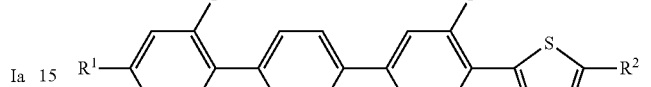
Im

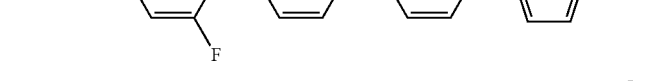
In

Io

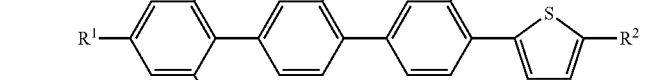
Ip

Iq in which $R^1$ and $R^2$ have the meanings indicated for the compound of formula I.

10. A process for preparing a compound of formula I according to claim 7, comprising reacting, in a palladium-promoted Suzuki cross-coupling, a substituted bromothiophene compound of formula 2

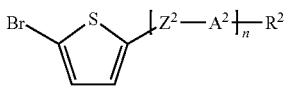

with a boronic acid compound of formula 1

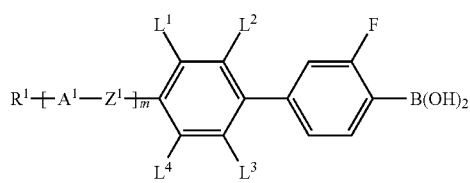

or a corresponding boronic acid ester,
or
reacting a bromobiphenyl compound of formula 10

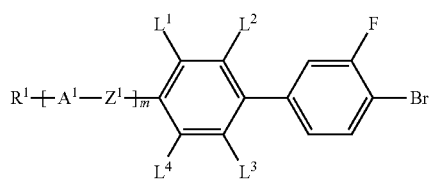

with a thiopheneboronic acid compound or a corresponding thiophenehydroxyboronic acid salt of formula 11

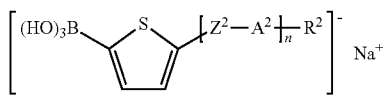

where
$R^{1,2}$, $A^{1,2}$, $Z^{1,2}$, m and n have the meaning indicated for the compound of formula I.

11. A LC display containing one or more compounds according to claim 7.

12. A LC display according to claim 11, which is an MLC, TN, STN or IPS display.

13. A LC medium according to claim 3, wherein $R^4$ denotes alkyl having 1 to 12 C atoms or alkenyl having 2 to 9 C atoms.

14. A LC display containing one or more compounds according to claim 8.

15. A LC medium according to claim 1, wherein $R^1$ and $R^2$ denote H, —SCN, $SF_5$ or straight-chain or branched alkyl having 1 to 12 C atoms, in which one or more non-adjacent $CH_2$ groups may each be replaced, independently of one another, by —C≡C—, —CO—, —CO—O—, —O—CO—, or —O—CO—O— in such a way that O atoms are not linked directly to one another, and in which one or more H atoms may be replaced by F, Cl or Br, or P-Sp-.

16. A LC medium according to claim 1, wherein $R^1$ and $R^2$ denote H, —SCN, $SF_5$ or straight-chain or branched alkyl having 1 to 12 C atoms, in which one or more non-adjacent $CH_2$ groups may each be replaced, independently of one another, by —CH=CH—, —C≡C—, —CO—, or —O—CO—O— in such a way that O atoms are not linked directly to one another, and in which one or more H atoms may be replaced by F, Cl or Br, or P-Sp-.

17. A LC medium according to claim 2, wherein $R^1$ and $R^2$ denote H, —SCN, $SF_5$ or straight-chain or branched alkyl having 1 to 12 C atoms, in which one or more non-adjacent $CH_2$ groups may each be replaced, independently of one another, by —C≡C—, —CO—, —CO—O—, —O—CO—, or —O—CO—O— in such a way that O atoms are not linked directly to one another, and in which one or more H atoms may be replaced by F, Cl or Br, or P-Sp-.

18. A LC medium according to claim 2, wherein $R^1$ and $R^2$ denote H, —SCN, $SF_5$ or straight-chain or branched alkyl having 1 to 12 C atoms, in which one or more non-adjacent $CH_2$ groups may each be replaced, independently of one another, by —CH=CH—, —C≡C—, —CO—, or —O—CO—O— in such a way that O atoms are not linked directly to one another, and in which one or more H atoms may be replaced by F, Cl or Br, or P-Sp-.

19. A LC medium according to claim 2, wherein the compound of formula I is a compound of one of formulae Id to Iq.

20. A LC medium according to claim 2, wherein the compound of formula I is a compound of one of formulae Io to Iq.

* * * * *

UNITED STATES PATENT AND TRADEMARK OFFICE
CERTIFICATE OF CORRECTION

PATENT NO.         : 8,394,293 B2
APPLICATION NO.    : 12/989220
DATED              : March 12, 2013
INVENTOR(S)        : Axel Jansen et al.

It is certified that error appears in the above-identified patent and that said Letters Patent is hereby corrected as shown below:

In The Claims:

Column 95, line 16 (Claim 1), reads: "-CH=CH-, -CO-, -CO-O-, -O-CO-, or"
Should read: -- -CH=CH-, -C≡C-, -CO-, -CO-O-, -O-CO-, or --.

Column 98, lines 2-9, Compound V, reads:

"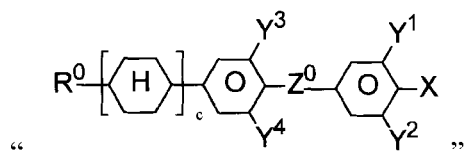"

Should read:

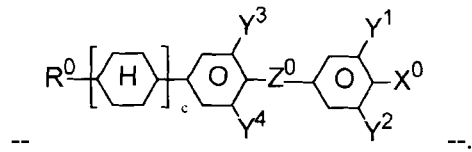
--         --.

Signed and Sealed this
Second Day of July, 2013

Teresa Stanek Rea
*Acting Director of the United States Patent and Trademark Office*